(12) United States Patent
Mewshaw et al.

(10) Patent No.: US 6,313,126 B1
(45) Date of Patent: Nov. 6, 2001

(54) ARYLPIPERAZINYL-CYCLOHEXYL INDOLE DERIVATIVES FOR THE TREATMENT OF DEPRESSION

(75) Inventors: Richard E. Mewshaw, King of Prussia, PA (US); Ping Zhou, Plainsboro, NJ (US); Dahui Zhou, East Brunswick, NJ (US); Kristin L. Meagher, Hightstown, NJ (US); Magda Asselin, Mahwah, NJ (US); Deborah A. Evrard, Hamilton Square, NJ (US); Adam M. Gilbert, Congers, NY (US)

(73) Assignee: American Home Products Corp, Madison, NJ (US)

( * ) Notice: Subject to any disclaimer, the term of this patent is extended or adjusted under 35 U.S.C. 154(b) by 0 days.

(21) Appl. No.: 09/476,254

(22) Filed: Dec. 30, 1999

Related U.S. Application Data

(60) Provisional application No. 60/155,199, filed on Jan. 7, 1999.

(51) Int. Cl.[7] .................. A61K 31/496; A61K 31/498; C07D 401/14; C07D 403/14; C07D 405/14
(52) U.S. Cl. ............ 514/249; 514/253.04; 514/253.06; 514/253.09; 514/254.09; 544/353; 544/362; 544/363; 544/364; 544/373
(58) Field of Search ..................... 544/362, 363, 544/373, 353, 364; 514/253.04, 253.06, 253.09, 254.09, 249

(56) References Cited

U.S. PATENT DOCUMENTS 5,468,767   11/1995   Cipollina et al. .................. 514/414

FOREIGN PATENT DOCUMENTS 345 808   * 12/1989   (EP).
WO9310092   5/1993   (WO).
WO9415928   7/1994   (WO).

OTHER PUBLICATIONS

Wustrow et al. *J. Med. Chem.*, 40, pp. 250–259, 1997.*
Willner, Medline Abstract for International Clinical Psychopharmacology 12 Suppl 3 pp. 7–14, 1997.*
Le Poul et al., *Arch. Pharmacol*, 352:141 (1995).
Artigas et al., Trends Neurosci., 19:378–383 (1996).

* cited by examiner

*Primary Examiner*—Emily Bernhardt
(74) *Attorney, Agent, or Firm*—Joseph M. Mazzarese

(57) ABSTRACT

Compounds are provided which are useful for the treatment of serotonin-affected neurological disorders which comprise

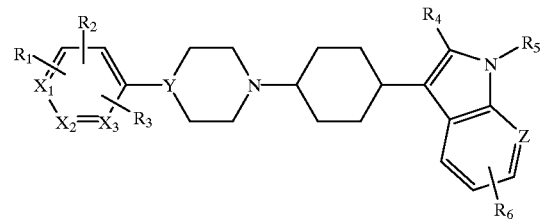

Wherein:
$R_1$, $R_2$ and $R_3$ are each, independently, hydrogen, halogen, $CF_3$, alkyl, alkoxy, $MeSO_2$, or together can form a 5–7 membered carbocyclic or heterocyclic ring;
$R_4$ is hydrogen, halogen, or alkyl;
$R_5$ is hydrogen, alkyl, alkylaryl, or aryl;
$R_6$ is hydrogen, halogen, $CF_3$, CN, carbamide, or alkoxy;
$X_1$, $X_2$ and $X_3$ are each carbon or one of $X_1$, $X_2$ or $X_3$ may be nitrogen;
Y is carbon or nitrogen; and
Z is carbon or nitrogen; or
pharmaceutically acceptable salts thereof.

68 Claims, No Drawings

ARYLPIPERAZINYL-CYCLOHEXYL INDOLE DERIVATIVES FOR THE TREATMENT OF DEPRESSION

CROSS REFERENCE TO RELATED APPLICATIONS

This application claims the benefit of U.S. Provisional Application No. 60/155,199, filed Jan. 7, 1999.

FIELD OF INVENTION

This invention relates to compounds useful for the treatment of diseases affected by disorders of the serotonin-affected neurological systems, such as depression and anxiety. More specifically the present invention is directed to arylpiperazinyl cyclohexyl derivatives useful for the treatment of such disorders.

BACKGROUND OF INVENTION

Pharmaceuticals which enhance neurotransmission of serotonin (5-HT) are useful for the treatment of many psychiatric disorders, including depression and anxiety. The first generation of non-selective serotonin-affecting drugs operated through a variety of physiological means which caused them to possess numerous undesired side-effects. The more recently prescribed drugs, the selective serotonin reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of 5-HT neurons, causing a dampening of the therapeutic effect. Studies suggest that after several weeks of SSRI administration, a desensitization of the 5-HT autoreceptors occurs allowing a full antidepressant effect in most patients. (See, e.g., Le Poul et al., *Arch. Pharmacol.*, 352:141 (1995)). Hence, it is believed that overriding this negative feedback by using 5HT1A antagonists would potentially increase and accelerate the clinical antidepressant response. Recent studies by Artigas et al., *Trends Neurosci.*, 19:378–383 (1996), suggest a combination of 5-HT1A activity and inhibition of 5-HT uptake within a single molecular entity can achieve a more robust and fast-acting antidepressant effect.

The present invention relates to a new class of molecules which have the ability to act at the 5-HT1A autoreceptors and concomitantly with the 5-HT transporter. Such compounds are therefore potentially useful for the treatment of depression as well as other serotonin disorders.

U.S. Pat. No. 5,468,767 reports a series of substituted indoles of the following formula for the treatment of disorders associated with dysfunction in serotonergic neurotransmission, including depression

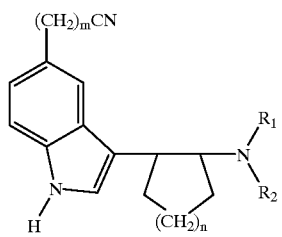

wherein:

$R_1$ is hydrogen or $C_{1-4}$ alkyl and $R_2$ is $C_{1-4}$ alkyl or $(CH_2)pAr$.

WO 9415928 discloses a series of piperazine derivatives of the following formula for the treatment of CNS disorders, including depression.

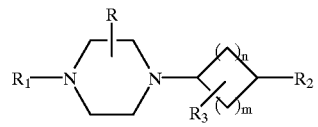

wherein:

R is hydrogen or alkyl;

$R_1$ and $R_2$ are each mono- or bicyclic aryl or heteroaryl radicals;

$R_3$ is hydrogen, alkyl, or a spirocycloalkyl group; and n is 1 or 2 and m is 1 to 3.

WO 93/10092 discloses a series of cyclohexenes of the following formula for the treatment of dopaminergic disorders.

SUMMARY OF THE INVENTION

The compounds of this invention are arylpiperazinyl-cyclohexyl indole derivatives represented by Formula I:

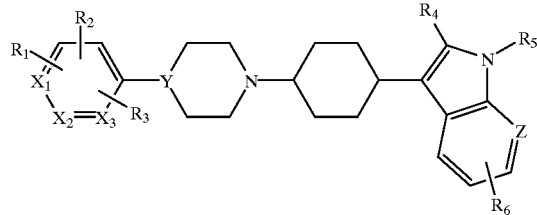

Wherein:

R$_1$, R$_2$ and R$_3$ are each, independently, hydrogen, halogen, CF$_3$, alkyl, alkoxy, MeSO$_2$, or together can form a 5–7 membered carbocyclic or heterocyclic ring;

R$_4$ is hydrogen, halogen, or alkyl;

R$_5$ is hydrogen, alkyl, alkylaryl, or aryl;

R$_6$ is hydrogen, halogen, CF$_3$, CN, carbamide, or alkoxy;

X$_1$, X$_2$ and X$_3$ are each carbon or one of X$_1$, X$_2$ or X$_3$ may be nitrogen;

Y is carbon or nitrogen; and

Z is carbon or nitrogen; or
pharmaceutically acceptable salts thereof.

Preferably, the compounds of the present invention are those represented by Formula I, wherein R$_1$, R$_2$ and R$_3$ are each, independently, hydrogen, halogen, alkyl, alkoxy or together form a 5–7 membered carbocyclic or heterocyclic ring;

R$_4$ is hydrogen or halogen;

R$_5$ is hydrogen, alkyl or alkylaryl; and

R$_6$ is hydrogen, halogen, CN or alkoxy;

X$_1$, X$_2$, X$_3$, Y and Z are each carbon; or
pharmaceutically acceptable salts thereof.

More preferably, the compounds of the present invention are selected from the following:

3-[cis-4-[4-(1H-Indol-4-yl)-1-piperazinyl]cyclohexyl]-1H-indole;

3-[trans-4-[4-(1H-indol-4-yl)-1-piperazinyl]cyclohexyl]-1H-indole;

4-Fluoro-3-[cis-4-[4-(1H-indol-4-yl)-1-piperazinyl]cyclohexyl]-1H-indole;

4-Fluoro-3-[trans-4-[4-(1H-indol-4-yl)-1-piperazinyl]cyclohexyl]-1H-indole;

5-Fluoro-3-[cis-4-[4-(1H-indol-4-yl)-1-piperazinyl]cyclohexyl]-1H-indole;

5-Fluoro-3-[trans-4-[4-(1H-indol-4-yl)-1-piperazinyl]cyclohexyl]-1H-indole;

6-Fluoro-3-[cis-4-[4-(1H-indol-4-yl)-1-piperazinyl]cyclohexyl]-1H-indole;

6-Fluoro-3-[trans-4-[4-(1H-indol-4-yl)-1-piperazinyl]cyclohexyl]-1H-indole;

5-Bromo-3-[cis-4-[4-(1H-indol-4-yl)-1-piperazinyl]cyclohexyl]-1H-indole;

5-Bromo-3-[trans-4-[4-(1 H-indol-4-yl)-1-piperazinyl]cyclohexyl]-1 H-indole;

5-Chloro-3-[cis-4-[4-(1H-indol-4-yl)-1-piperazinyl]cyclohexyl]-1H-indole;

5-Chloro-3-[trans-4-[4-(1H-indol-4-yl)-1-piperazinyl]cyclohexyl]-1H-indole;

3-{4-[(1,4-cis)-4-(1H-indol-4-yl)-piperazinyl-1-yl]cyclohexyl}-1H-indole-5-carbonitrile;

3-{4-[(1,4-trans)-4-(1H-indol-4-yl)-piperazinyl-1-yl]cyclohexyl}-1H-indole-5-carbonitrile;

5-Methoxy-3-[cis-4-[4-(1H-indol-4-yl)-1-piperazinyl]cyclohexyl]-1H-indole;

5-Methoxy-3-[trans-4-[4-(1H-indol-4-yl)-1-piperazinyl]cyclohexyl]-1H-indole;

3-[cis-4-[4-(1H-Indol-4-yl)-1-piperazinyl]cyclohexyl]-2-methyl-1H-indole;

3-[trans-4-[4-(1H-Indol-4-yl)-1-piperazinyl]cyclohexyl]-2-methyl-1H-indole;

3-{(1,4-cis)-4-[4-1H-Indole-4-yl)-piperazin-1-yl]-cyclohexyl}-1H-pyrrolo[2,3-b]pyridine;

3-{(1,4-trans)-4-[4-(1H-Indol-4-yl)-piperazin-1-yl]-cyclohexyl}-1H-pyrrolo[2,3-b]pyridine;

6-Fluoro-1-methyl-3-{cis-4-[4-(1-methyl-1H-indol-4-yl)-1-piperazinyl]cyclohexyl}-1H-indole;

3-{(1,4-cis)-4-[4-(1H-indol-4-yl)-piperazin-1-yl]cyclohexyl}-1-methyl-1H-indole-5-carbonitrile;

3-{(1,4-trans)-4-[4-(1H-indol-4-yl)-piperazin-1-yl]cyclohexyl}-1-methyl-1H-5-carbonitrile;

1-Ethyl-3-{(1,4-cis)-4-[4-(1H-indole-4-yl)-piperazin-1-yl]-cyclohexyl}-1H-indole-5-carbonitrile;

3-{(1,4-cis)-4-[4-(1H-indol-4-yl)-piperazin-1-yl]-cyclohexyl}-1-propyl-1H-indole-5-carbonitrile;

3-{(1,4-trans)-4-[4-(1H-indol-4-yl)-piperazin-1-yl]-cyclohexyl;}-1-propyl-1H-indole-5-carbonitrile;

3-{(1,4-cis)-4-[4-(1H-indol-4-yl)-piperazin-1-yl]-cyclohexyl}-1-isopropyl-1H-indole-5-carbonitrile;

3-{(1,4-trans)-4-[4-(1 H-indol-4-yl)-piperazin-1-yl]-cyclohexyl}-1-isopropyl-1H-indole-5-carbonitrile;

1-Benzyl-3-{(1,4-cis)-4-[4-(1H-indol-4-yl)-piperazin-1-yl]-cyclohexyl}-1H-indole-5-carbonitrile;

1-Benzyl-3-{(1,4-trans)-4-[4-(1H-indole-4-yl)-piperazin-1-yl]cyclohexyl}-1H-indole-5-carbonitrile;

1-Methyl-3-{(1,4-cis)-4-[4-(1-methyl-1H-indol-4-yl)-piperazine-1-yl]-cyclohexl}-1H-indole-5-carbonitrile;

5-Fluoro-3-{(cis)-4-[4-(2-methoxy-phenyl)-piperazin-1-yl]-cyclohexyl}-1H-indole;

5-Fluoro-3-{(1,4-cis)-4-[4-(2-methoxy-phenyl)-piperidin-1-yl]-cyclohexyl}-1H-indole;

5-Fluoro-3-{(1,4-trans)-4-[4-(2-methoxy-phenyl)-piperidin-1-yl]-cyclohexyl}-1H-indole;

5-methoxy-3-{(1,4-cis)-4-[4-(2-methoxy-phenyl)-piperazinyl-1-yl]-cyclohexyl}-1H-indole;

5-Methoxy-3-{(1,4-trans)-4-[4-(2-methoxy-phenyl)-piperidin-1-yl]-cyclohexyl}-1H-indole;

3-{(1,4-cis)-4-[4-(2-methoxy-phenyl)-piperazin-1-yl]-cyclohexyl}-1H-pyrrolo[2,3-b]piperidine;

5-Fluoro-3-{(cis)-4-[4-(5-fluoro-2-methoxy-phenyl)-piperazin-1-yl]-cyclohexyl}-1H-indole;

5-Fluoro-3-{(trans)-4-[4-(5-fluoro-2-methoxy-phenyl)-piperazin-1-yl]-cyclohexyl}-1H-indole;

3-{(1,4-cis)-4-[4[(2,3-Dihydro-benzo[1,4]dioxin-5-yl)-piperazin-1-yl]-cyclohexyl}-4-fluoro-1H-indole;

3-{(1,4-trans)-4-[4-(2,3-Dihydro-benzo[1,4]dioxin-5-yl)-piperazin-1-yl]-cyclohexyl}-4-fluoro-1H-indole;

3-{(1,4-cis)-4-[4-(2,3-Dihydro-benzo[1,4]dioxin-5-yl)-piperazin-1-yl]-cyclohexyl}-5-fluoro-1H-indole;

3-{(1,4-trans)-4-[4-(2,3-Dihydro-benzo[1,4]dioxin-5-yl)-piperazin-1-yl]-cyclohexyl}-5-fluoro-1H-indole;

3-{(1,4-cis)-4-[4-(2,3-Dihydro-benzo[1,4]dioxin-5-yl)-piperazin-1-yl]-cyclohexyl}-6-fluoro-1H-indole;

3-{(1,4-trans)-4-[4-(2,3-Dihydro-benzo[1,4]dioxin-5-yl)-piperazin-1-yl]-cyclohexyl}-6-fluoro-1H-indole;

3-{(1,4-trans)-4-[4-(2,3-Dihydro-benzo[1,4]dioxin-5-yl)-piperazin-1-yl]-cyclohexyl}-6-fluoro-1H-indole;

3-{(1,4-cis)-4-[4-(2,3-Dihydro-benzo[1,4]dioxin-5-yl)-piperazin-1-yl]-cyclohexyl}-1H-indole-5-carbonitrile;

3-{(1,4-trans)-4-(4-(2,3-Dihydro-benzo[1,4]dioxin-5-yl)-piperazin-1-yl]-cyclohexyl}-1H-indole-5-carbonitrile;

8-{4-[(1,4-cis)-4-(5-Fluoro-1H-indol-3-yl)-cyclohexyl]-piperazin-1-yl}quinoline;

8-{4-[(1,4-trans)-4-(5-Fluoro-1H-indol-3-yl)-cyclohexyl]-piperazin-1-yl}-quinoline;

8-{4-(1,4-cis)-4-[4-(5-Fluoro-1-methyl-1H-indol-3-yl)-cyclohexyl]-piperazin-1-quinoline;

3-[(1,4-cis)-4-(4-Quinolin-8-yl-piperazin-1-yl)-cyclohexyl]-1H-indole-5-carbonitrile;

3-[(1,4-trans)-4-(4-Quinolin-8-yl-piperazin-1-yl)-cyclohexyl]-1H-indole-5-carbonitrile;

1-Methyl-3-[(1,4-cis)-4-(4-quinolin-8-yl-piperazin-1-yl)-cyclohexyl]-1H-indole-5-carbonitrile;

5-Fluoro-3-{(1,4-cis)-4-[4-(6-fluoro-chroman-8-yl)-piperazin-1-yl]-cyclohexyl}-1H-indole;

5-Fluoro-3-{(1,4-trans)-4-[4-(6-fluoro-chroman-8-yl)-piperazin-1-yl]-cyclohexyl}-1H-indole;

5-Fluoro-3-{(1,4-cis)-4-[4-(5-fluoro-2,3-dihydro-benzofuran-7-yl)-piperazin-1-yl]-cyclohexyl}-1H-indole;

5-Fluoro-3-{(1,4-trans)-4-[4-(5-fluoro-2,3-dihydro-benzofuran-7-yl)-piperazin-1-yl]-cyclohexyl}-1H-indole;

3-{(1,4-cis)-4-[4-(5-Fluoro-2,3-dihydro-benzofuran-7-yl)-piperazin-1-yl]-cyclohexyl}-1H-indole-5-carbonitrile;

3-{(1,4-trans)-4-[4-(5-Fluoro-2,3-dihydro-benzofuran-7-yl)-piperazin-1-yl]-cyclohexyl}-1H-indole-5-carbonitrile;

3-{(1,4-cis)-4-[4-(5-Fluoro-2,3-dihydro-benzofuran-7-yl)-piperazin-1-yl]-cyclohexyl}-1-methyl-1H-indole-5-carbonitrile;

3-[(1,4-cis)-4-[4-(Benzofuran-7-yl-piperazin-1-yl)-cyclohexyl]-1H-indole-5-carbonitrile;

3-[(1,4-trans)-4-[4-(Benzofuran-7-yl-piperazin-1-yl)-cyclohexyl]-1H-indole-5-carbonitrile;

5-Fluoro-3-{4-[4-(2-methoxy-phenyl)-piperazin-1-yl]cyclohex-1-enyl}-1H-indole;

3-{4-[4-(1H-Indol-4-yl)-piperazin-1-yl]-cyclohex-1-enyl}-1H-indole-5-carbonitrile;

5-Fluoro-3-{(1,4-cis)-4-[4-(2-methoxy-phenyl)-piperazin-1-yl]-cyclohexyl}-1,3-dihydro-indol-2-one;

5-Fluoro-3-{cis-4-[4-(1H-indol-4-yl)piperazinyl]-cyclohexyl}-1-methyl-1H-indole;

8{(1,4-cis)-4-[4-(5-Fluoro-1H-indol-3-yl)-cyclohexyl]-piperazin-1-yl}-6-methoxy-quinoline;

8-{(1,4-trans)-4-[4-(5-Fluoro-1H-indol-3-yl)-cyclohexyl]piperazin-1-yl}-6-methoxy-quinoline;

3-{(1,4-cis)-4-[4-6-Methoxy-quinoline-8-yl)-piperazin-1-yl]-cyclohexyl}-1H-indole-5-carbonitrile;

3-{(1,4-trans)-4-[4-(6-Methoxy-quinolin-8-yl)-piperazin-1-yl]-cyclohexyl}-1H-indole-5-carbonitrile;

6-Chloro-8-{4-[1,4-cis)-4-(5-fluoro-1H-indol-3-yl)-cyclohexyl]-piperazin-1-yl}quinoline;

6-Chloro-8-{4-[(1,4-trans)-4-(5-fluoro-1H-indol-3-yl)-cyclohexyl]-piperazin-1-yl}quinoline;

3-{(1,4-cis)-4-[(4-(6-Chloro-quinolin-8-yl)-piperazin-1-yl]-cyclohexyl}-1H-indole-5-carbonitrile;

3-{(1,4-trans)-4-[4-(6-Chloro-quinolin-8-yl)-piperazin-1-yl]-cyclohexyl}-1H-indole-5-carbonitrile;

5-Chloro-8-{4-[(1,4-cis)-4-(5-fluoro-1H-indol-3-yl)-cyclohexyl]-piperazin-quinoline;

3-{(1,4-cis)-4-[4-(5-Chloro-quinolin-8-yl)-piperazin-1-yl]-cyclohexyl}-1H-indole-5-carbonitrile;

5-Fluoro-8-{4-[(1,4-cis)-4-(6-fluoro-1H-indole-3-yl)-cyclohexyl]-piperazin-1-yl}-quinoline;

5-Fluoro-8-{4-[(1,4-trans)-4-(6-fluoro-1H-indol-3-yl)-cyclohexyl]-piperazin-1-yl}-quinoline;

3-{(1,4-cis)-4-[4-(2-Methyl-quinolin-8-yl)-piperazin-1-yl]-cyclohexyl}-1H-indole-5-carbonitrile;

3-{(1,4-trans)-4-[4-(2-Methyl-quinolin-8-yl)-piperazin-1-yl]-cyclohexyl}-1H-indole-5-carbonitrile;

4-{4-[(1,4-cis)-4-(5-Fluoro-1H-indol-3-yl)-cyclohexyl]-piperazin-1-yl}-2-trifluoromethyl-quinoline;

4-{4-[(1,4-trans)-4-(5-Fluoro-1H-indol-3-yl)-cyclohexyl]-piperazin-1-yl}-2-trifluoromethyl-quinoline;

3-{(1,4-cis)-4-[4-(2-Trifluoromethyl-quinolin-4-yl)-piperazin-1-yl]-cyclohexyl }-1H-indole-5-carbonitrile 3-{(1,4-trans)-4-[4-(2-Trifluoromethyl-quinolin-4-yl)-piperazin-1-yl]-cyclohexyl}-1H-indole-5-carbonitrile;

4-{4-[(1,4-cis)-4-(5-Fluoro-1H-indol-3-yl)-cyclohexyl]-piperazin-1-yl}-6-methoxy-quinoline;

4-{4[(1,4-trans)-4-(5-Fluoro-1H-indol-3-yl)-cyclohexyl]-piperazin-1-yl}-6-methoxy-quinoline;

3-{(1,4-cis)-4-[4-(6-Methoxy-quinolin-4-yl)-piperazin-1-yl]-cyclohexyl}-1H-indole-5-carbonitrile; and 3-{(1,4-trans)-4-[4-(6-Methoxy-quinolin-4-yl)-piperazin-1-yl]-cyclohexyl}-1H-indole-5-carbonitrile.

As used herein, the terms "alkyl" and "alkoxy" are meant to include both straight and branched carbon chains containing 1–6 carbon atoms. The term "aryl" is meant to include aromatic radicals of 6–12 carbon atoms. The term "halogen" is meant to include fluorine, chlorine, bromine and iodine.

The compounds of Formula I also may be used in the form of a pharmaceutically acceptable acid addition salt having the utility of the free base. Such salts, prepared by methods well known to those skilled in the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

The compounds of the present invention may be prepared by any suitable method which will be recognized by those skilled in the art. However, the present compounds may be advantageously prepared according to any one of Schemes 1–6 set forth below. In the Schemes, the intermediate compounds exemplified hereinafter are identified in parenthesis. The compound produced in each of Schemes 1–6 is identified with reference to the appropriate Example set forth below.

The preparation of such compounds is depicted in Schemes 1–6 below.

Scheme 1
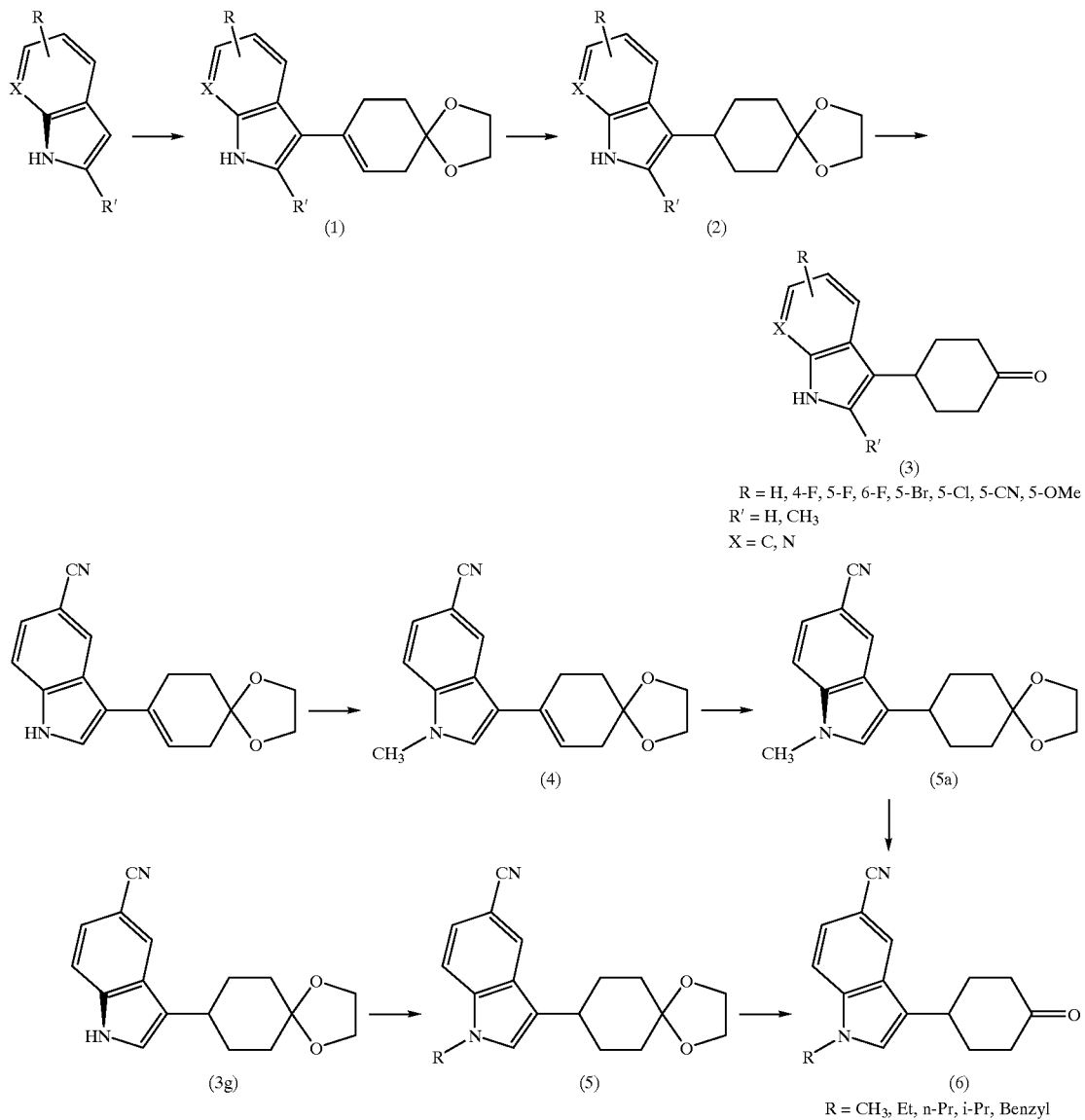
Scheme 2
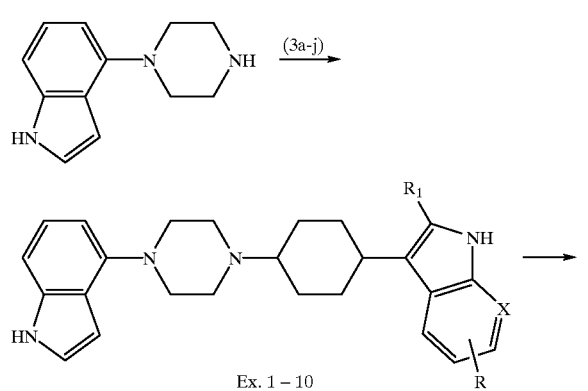
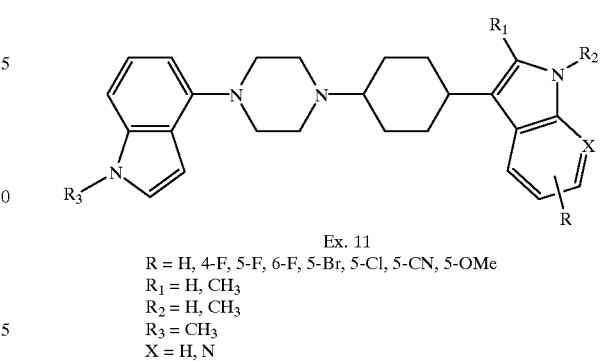

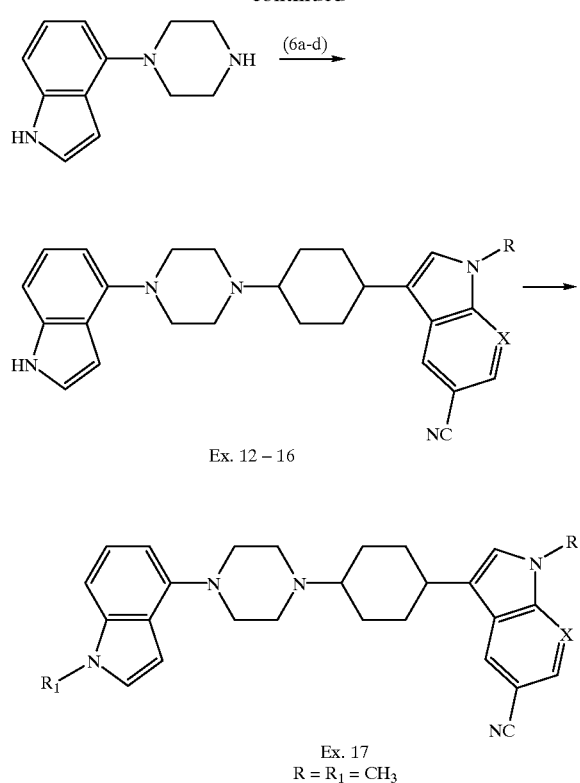
Ex. 12 – 16
Ex. 17
R = R$_1$ = CH$_3$
Ex. 18 – 22
R = 5-F, 5-OCH$_3$
R' = H, F
R = N, C
Ex. 23 – 26
R = 4=F, 5-F, 6-F, 5-CN
Scheme 3
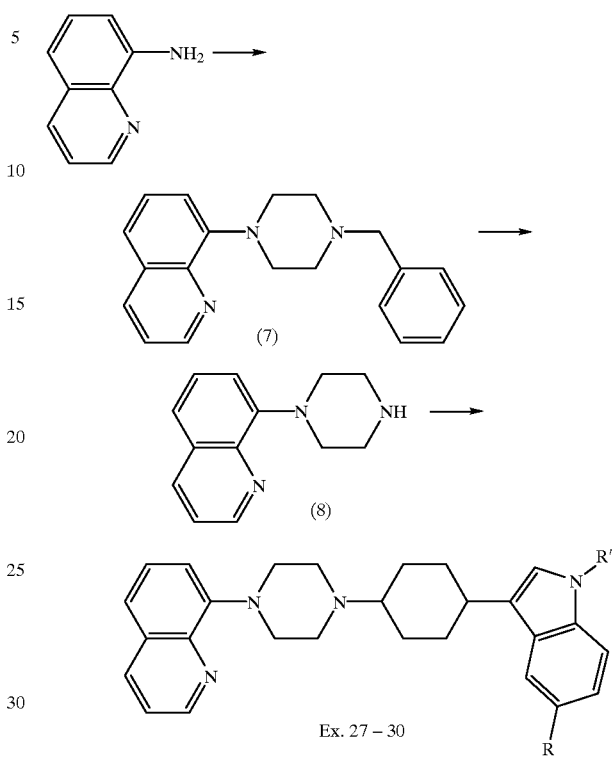
Ex. 27 – 30
Scheme 4
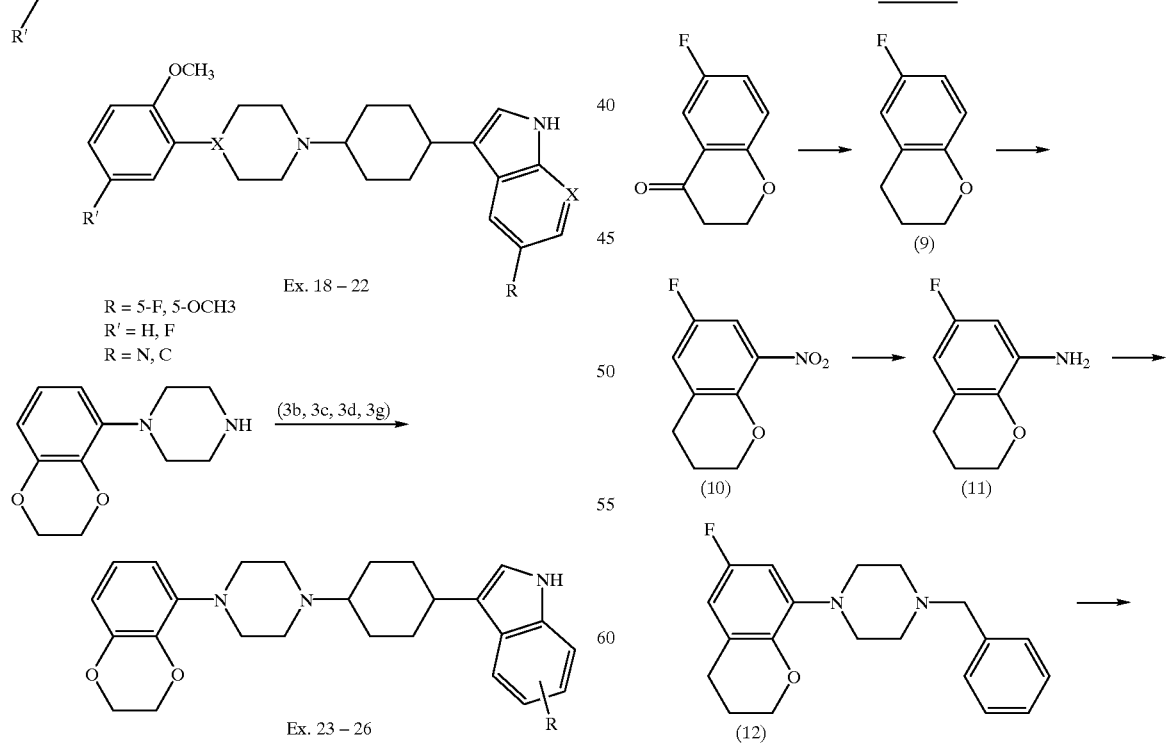

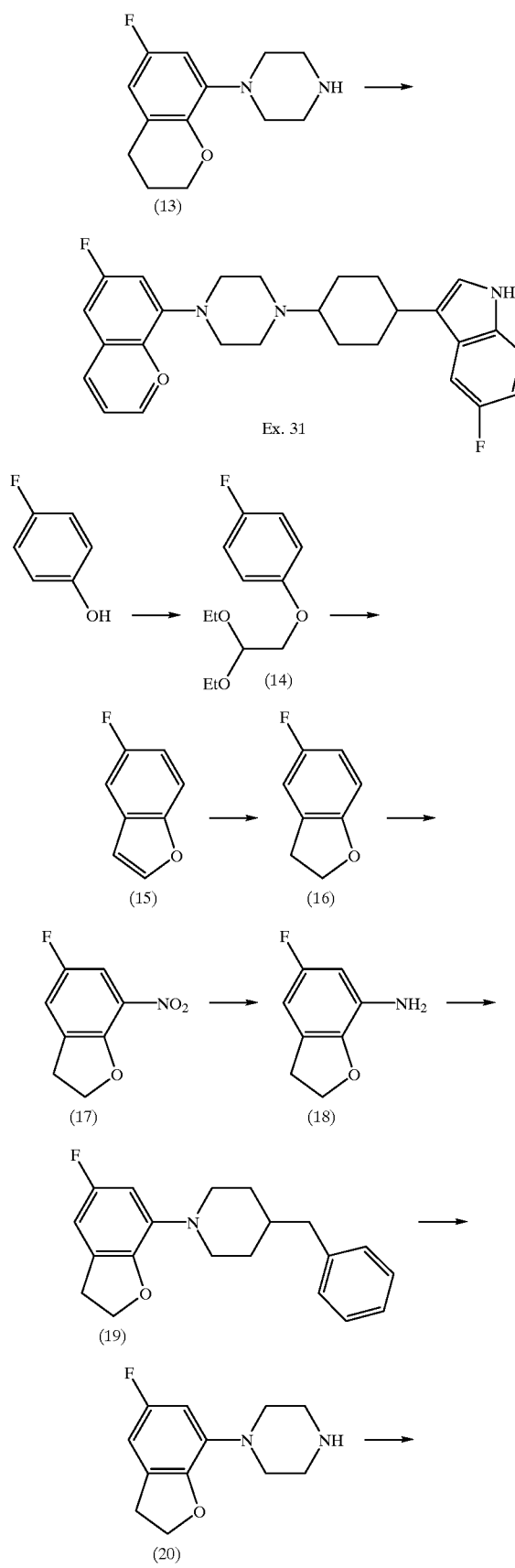
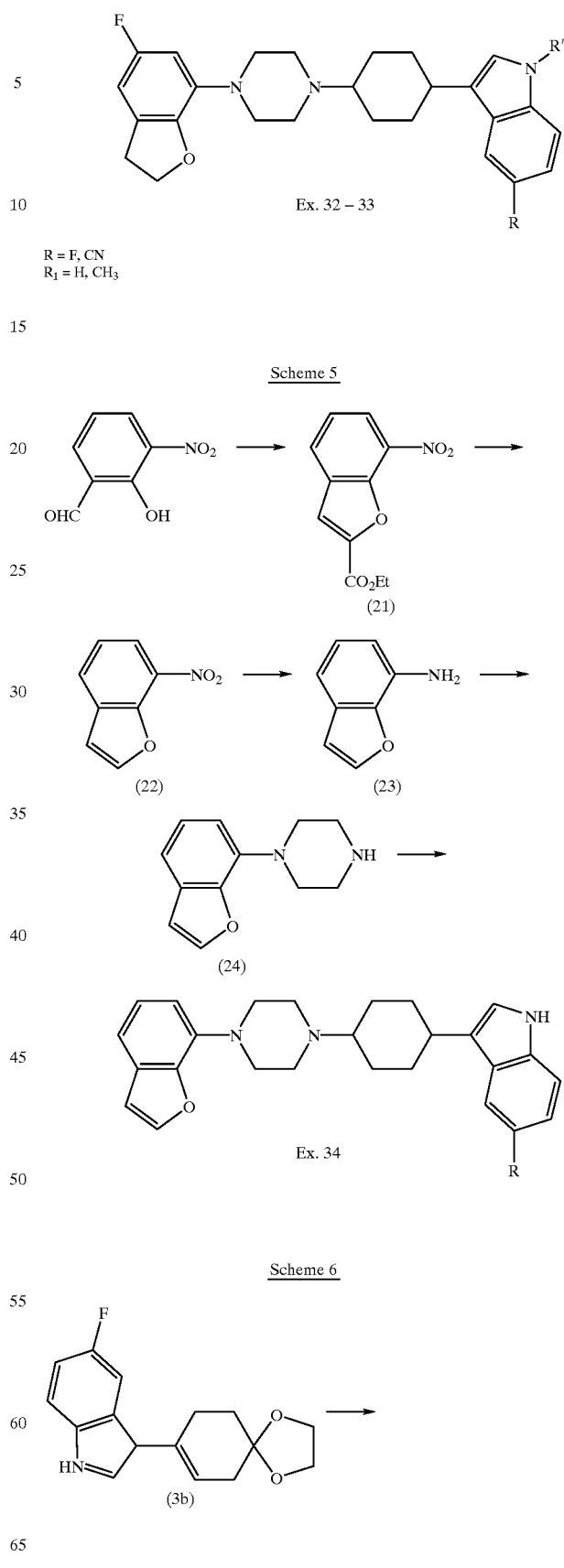
R = F, CN
R₁ = H, CH₃
Scheme 5
Scheme 6

-continued (25)

Ex. 35

(25)

Ex. 36

(26)

(27)

(28)

-continued (29)

(30)

Ex. 38

Scheme 7

(31)

(32)

(33)

-continued

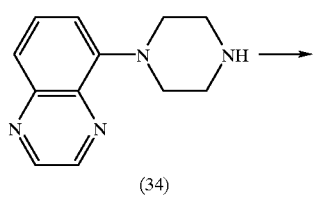

(34)

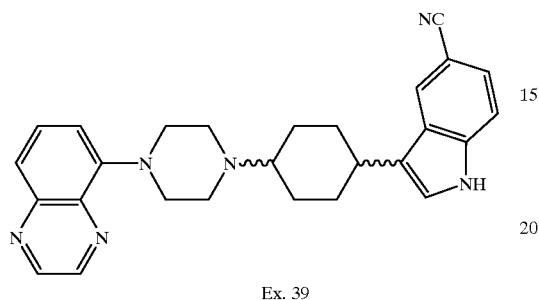

Ex. 39

Scheme 8

Ar—OH → Ar—OTf →
                (35)

Ar—N(piperazine)N—Boc → Ar—N(piperazine)NH →
      (36)                    (37)

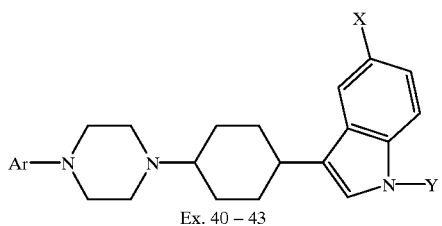

Ex. 40 – 43

X = F, CN
Y = H, Me
Ar = 5-quinolinyl, 5-isoquinolinyl, 1-naphthyl

Scheme 9

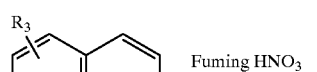

Quinoline

Fuming HNO₃ →

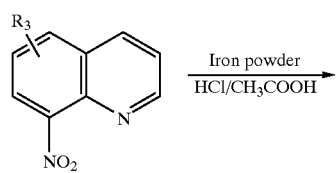

Intermediate 40

Iron powder
HCl/CH₃COOH →

-continued

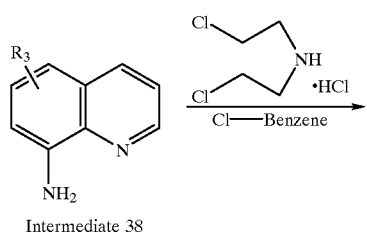

Intermediate 38

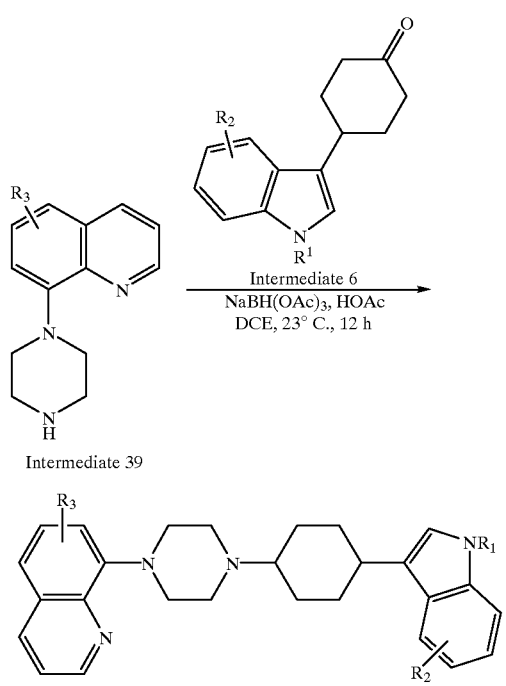

Intermediate 39

Intermediate 6
NaBH(OAc)₃, HOAc
DCE, 23° C., 12 h →

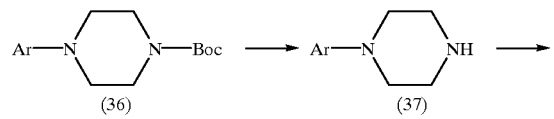

Ex. 44 when R₃ is 6-MeO
Ex. 45 when R₃ is 6-Cl

R₁ is H
R₂ is 5-F, 5-CN

Scheme 10

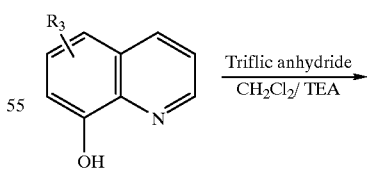

Triflic anhydride
CH₂Cl₂/ TEA →

Intermediate 4 piperazine →

-continued
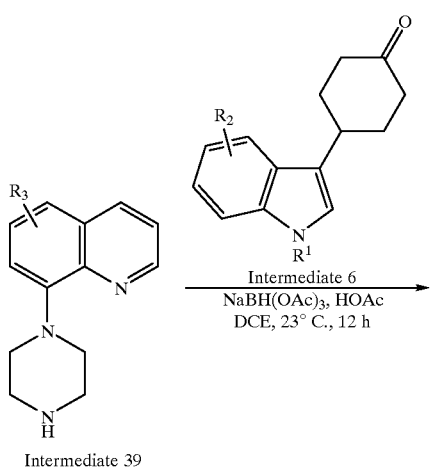
Intermediate 39
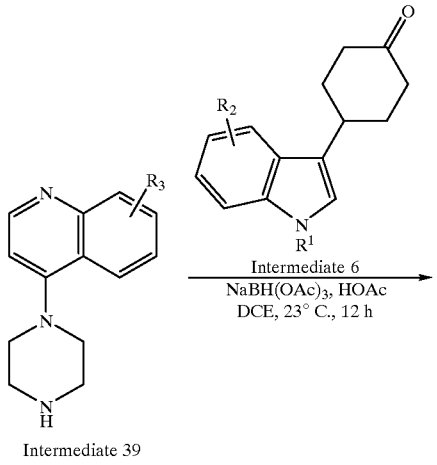
Intermediate 39
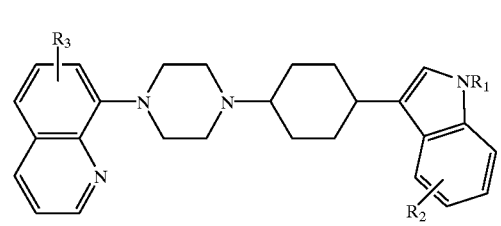
Ex. 46 when $R_3$ is 5-Cl
Ex. 47 when $R_3$ is 5-F
Ex. 48 when $R_3$ is 2-CH$_3$
$R_1$ is H
$R_2$ is 5-F, 6-F, 5-CN
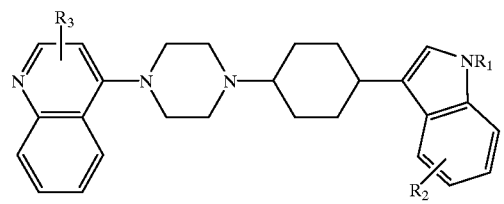
Ex. 49 when $R_3$ is 2-CF$_3$
Ex. 50 when $R_3$ is 6-MeO
$R_1$ is H
$R_2$ is 5-F, 6-F, 5-CN
Scheme 11
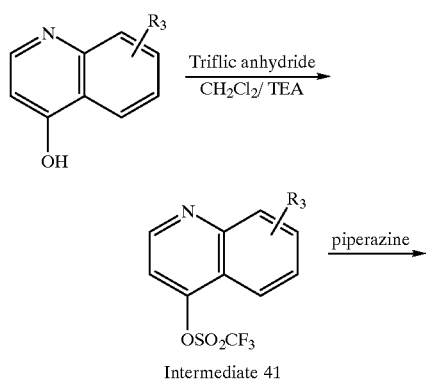
Intermediate 41
Scheme 12
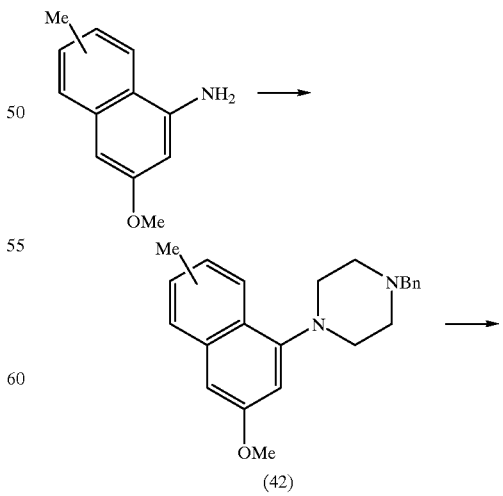
(42)

-continued
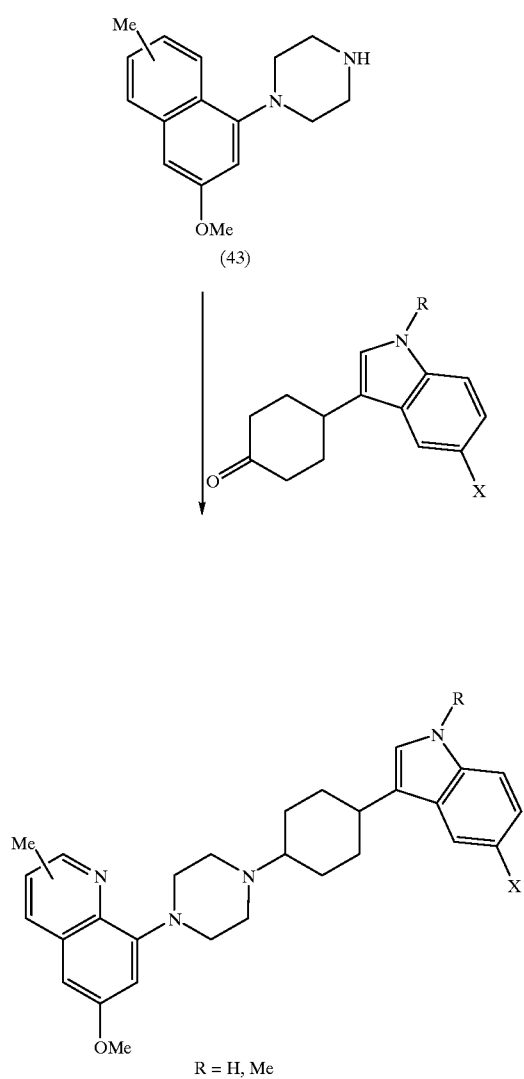
R = H, Me
X = F, CN
Example 51
-continued
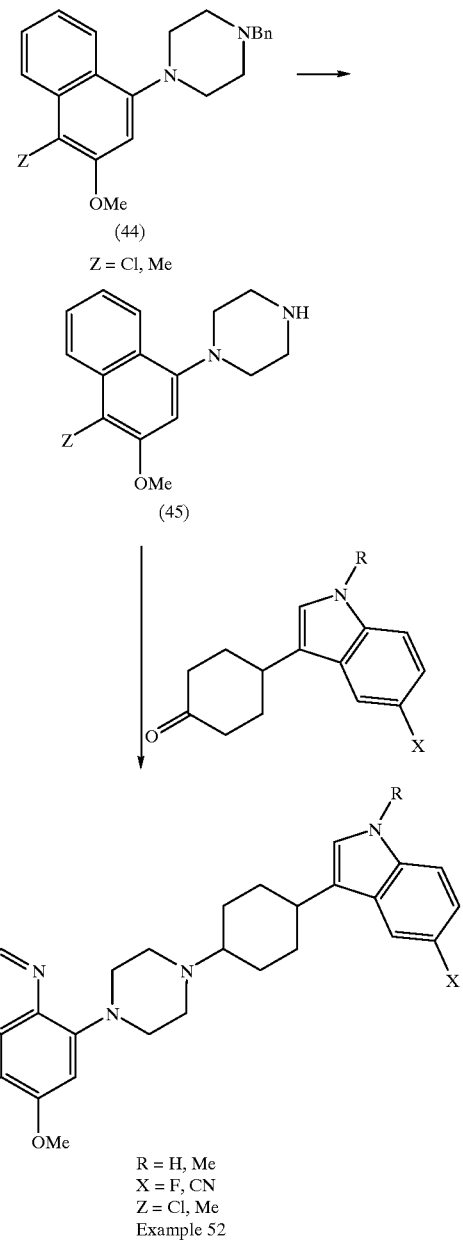
R = H, Me
X = F, CN
Z = Cl, Me
Example 52
Scheme 13
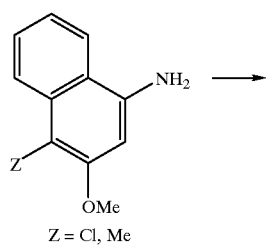
Z = Cl, Me
Scheme 14
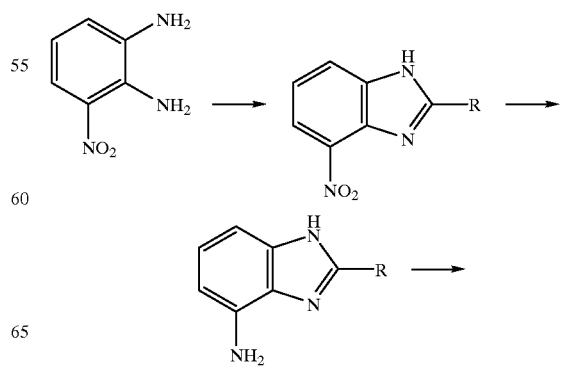

21
-continued
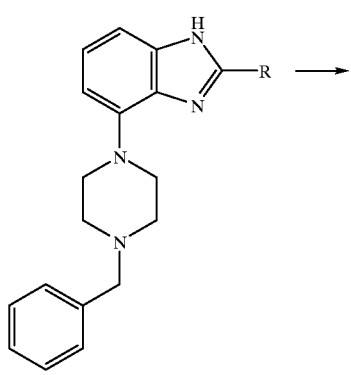
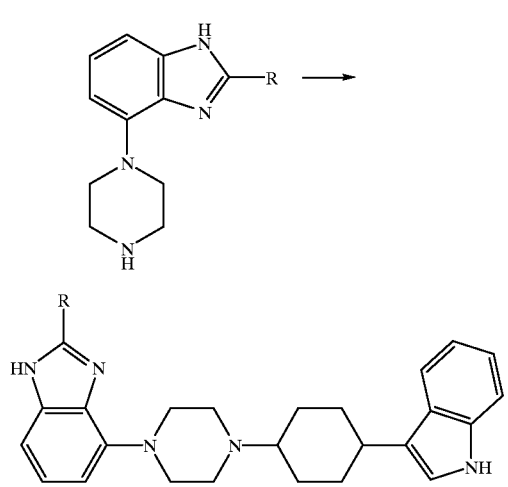
Example 53 R = H
Example 54 R = CH3
Example 55 R = CF3
Scheme 15
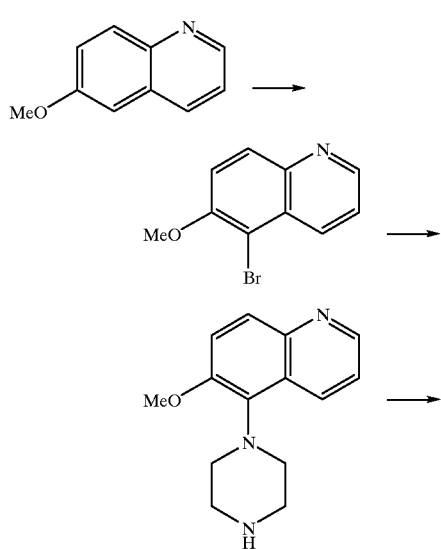
22
-continued
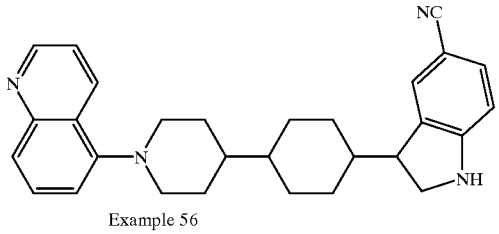
Example 56
Scheme 16
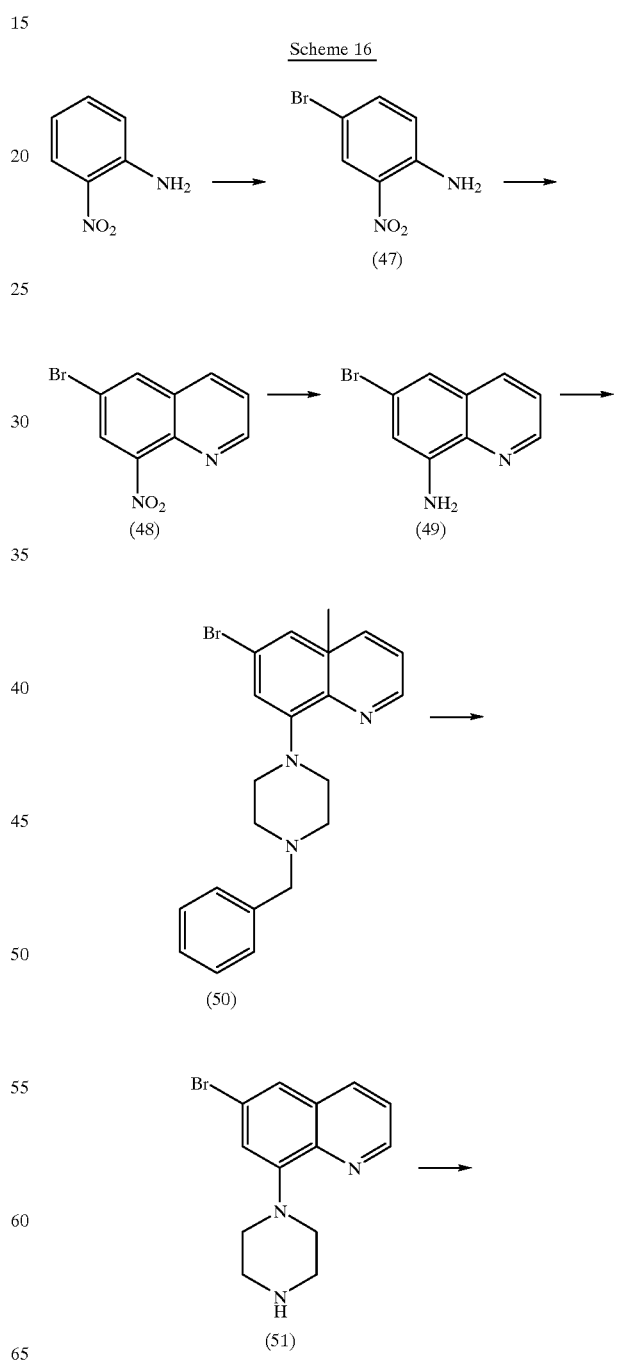
(47)
(48)
(49)
(50)
(51)

23
-continued
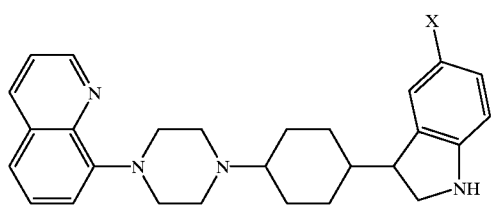
Example 57 X = CN
Example 58 X = F
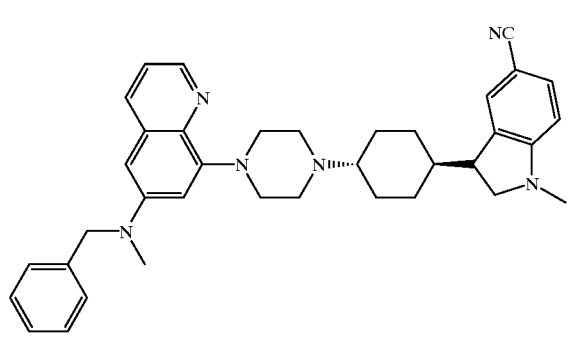
Example 60
Scheme 17
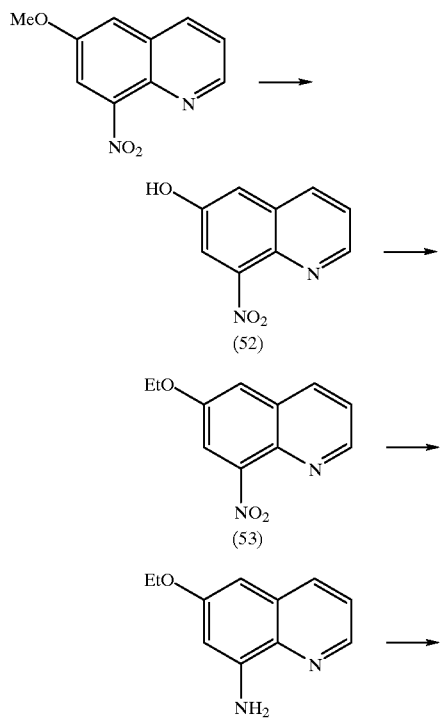
24
-continued
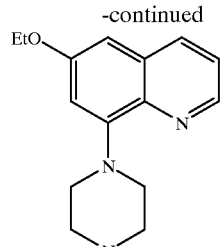
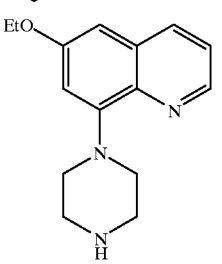
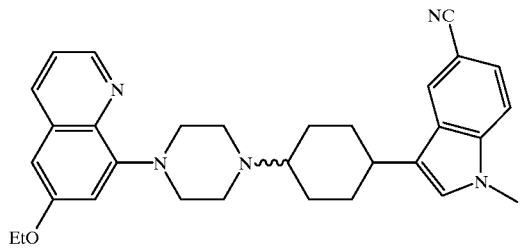
Example 59
Scheme 18
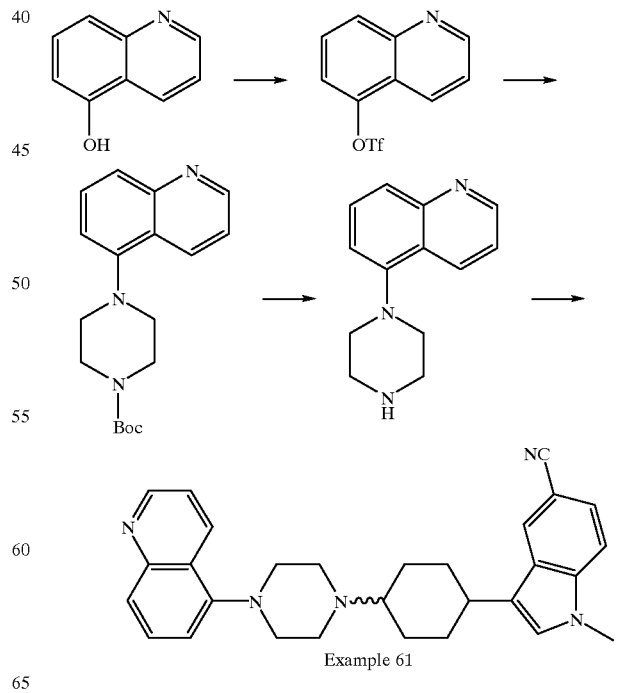
Example 61

Scheme 19
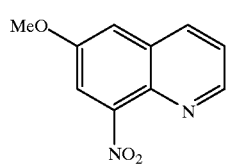
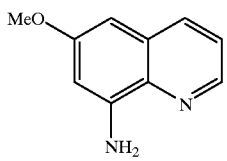
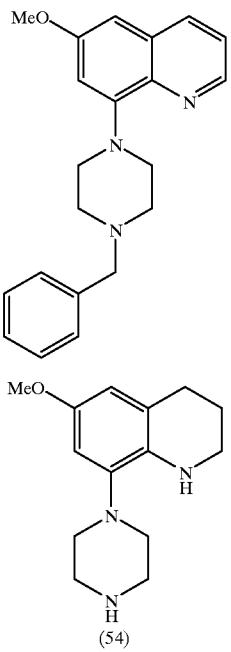
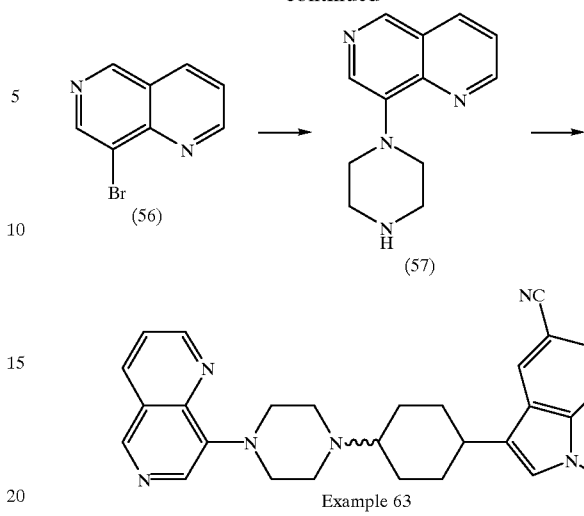
Scheme 20
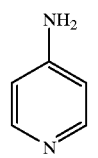 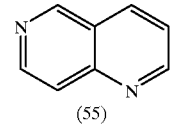 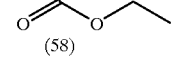

-continued
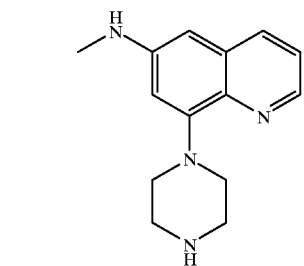
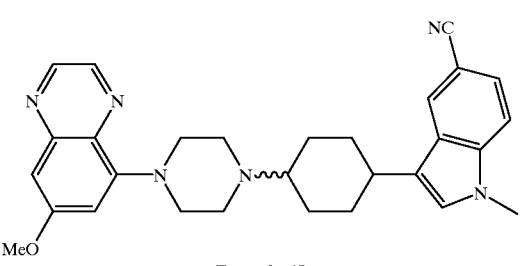
Example 65
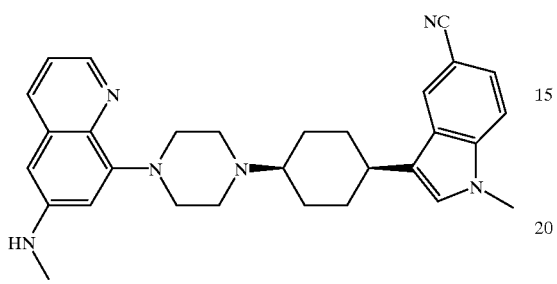
Example 64
Scheme 22
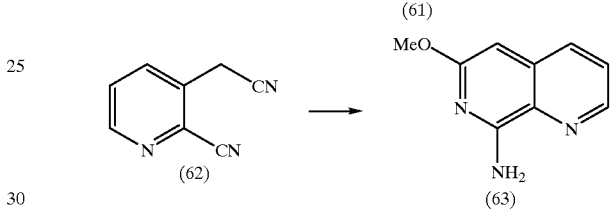
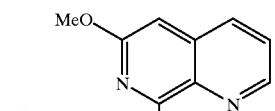
(62)
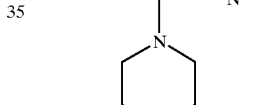
(63)
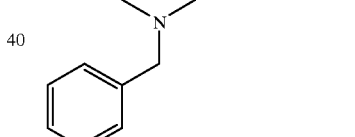
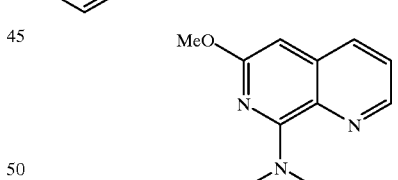
Scheme 21
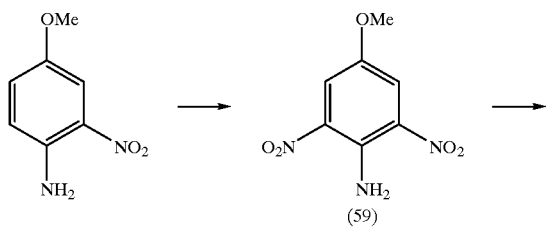
(59)
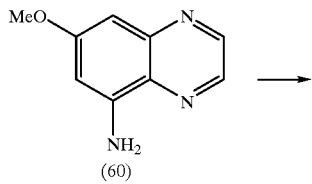
(60)
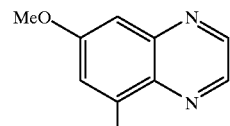
(64)
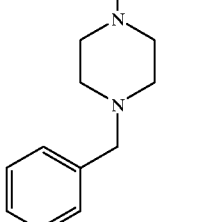
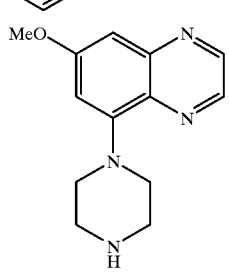
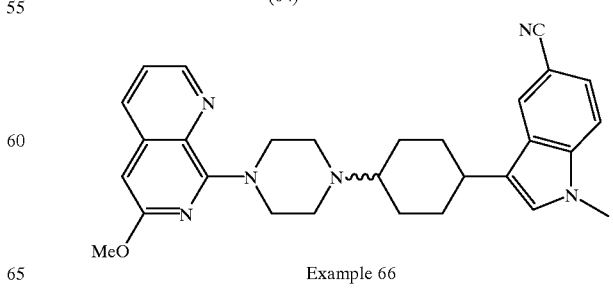
Example 66

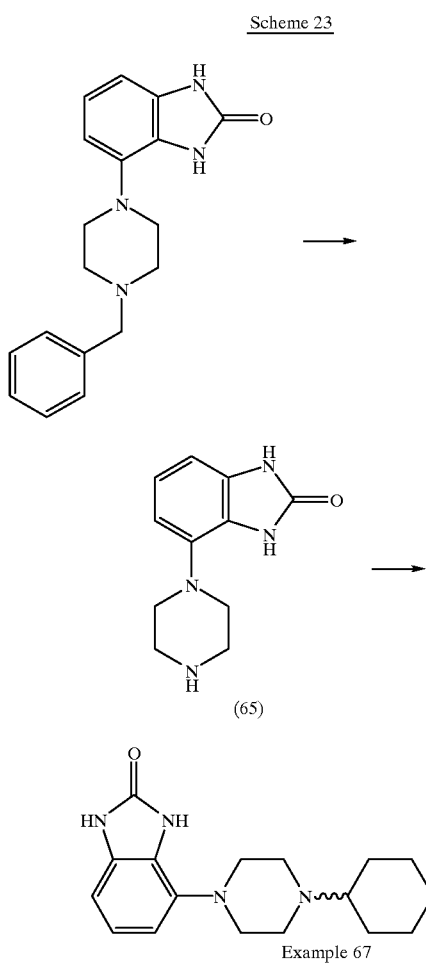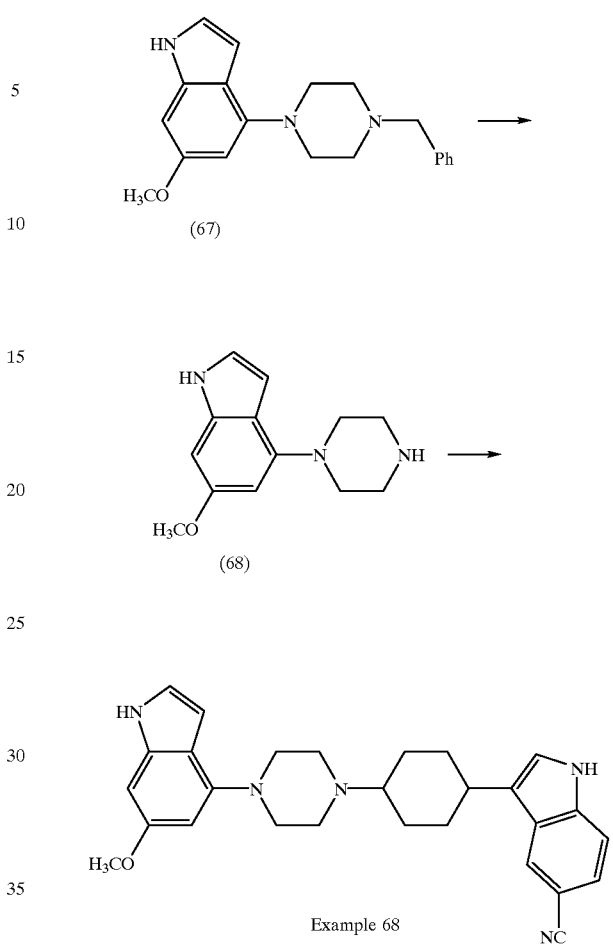

Scheme 26
(Examples 70–75)
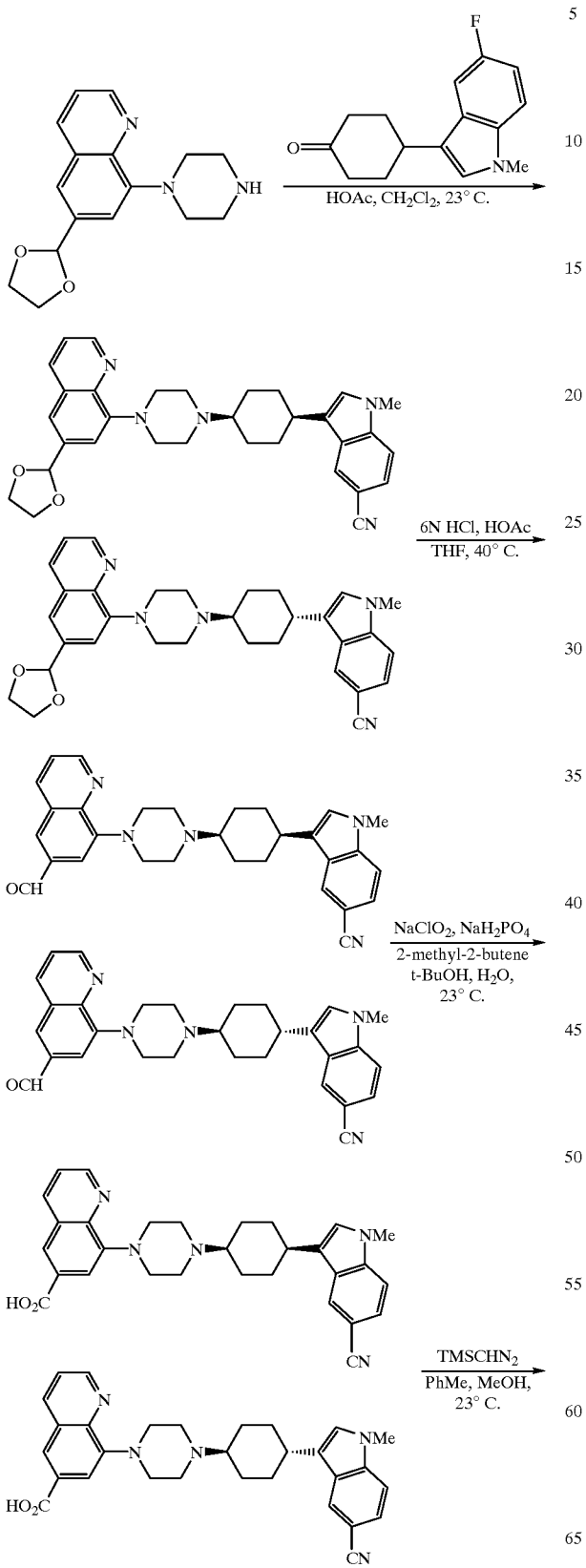
Scheme 27
(Example 76)
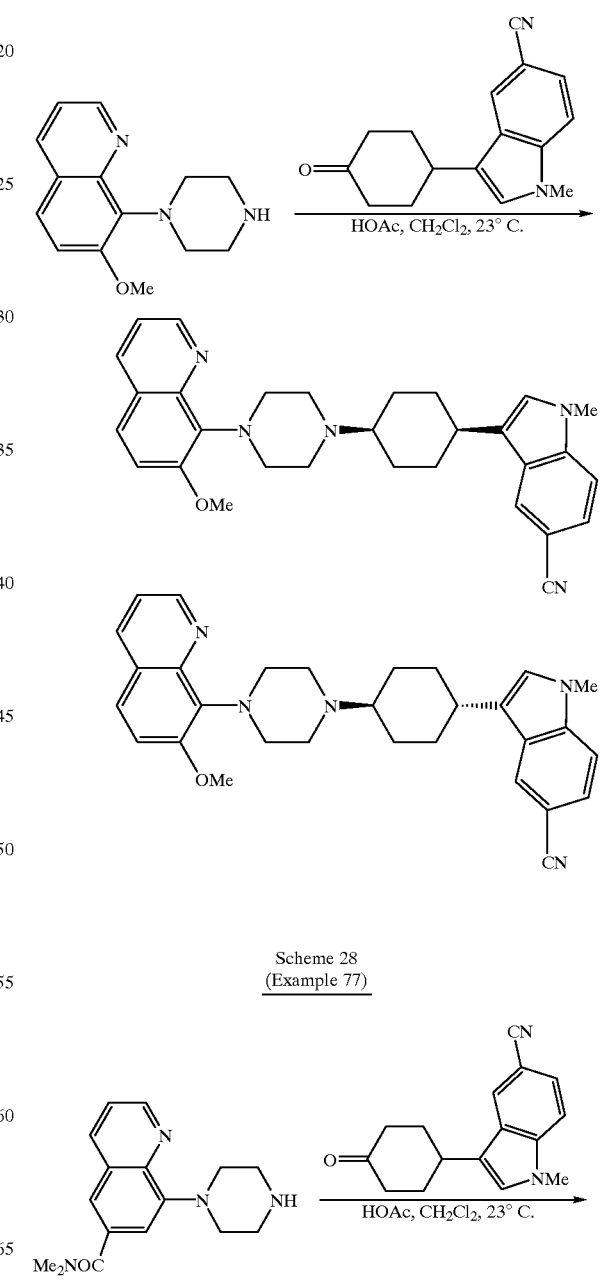
Scheme 28
(Example 77)

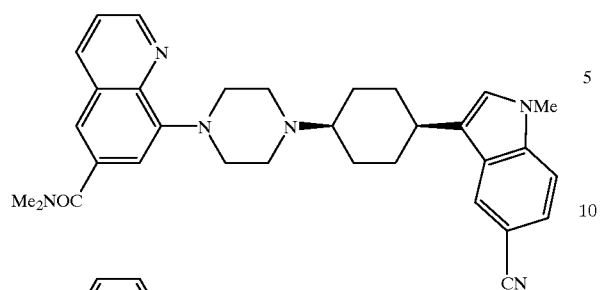
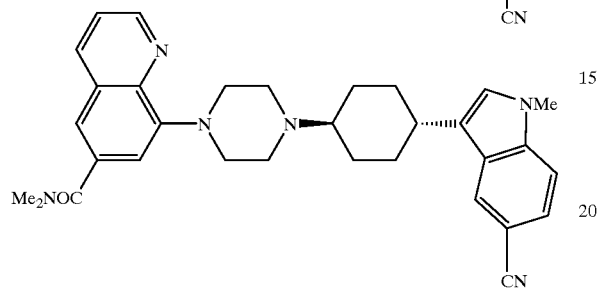
Scheme 29
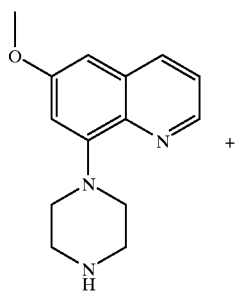
Example 78
Scheme 30
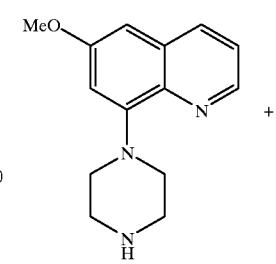
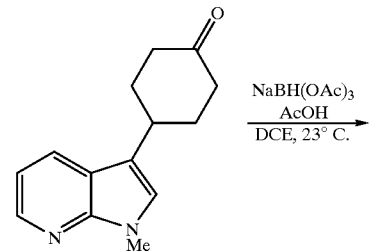
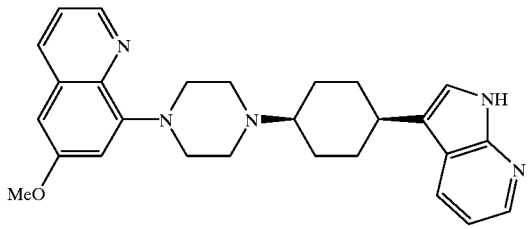
Example 79
Scheme 31
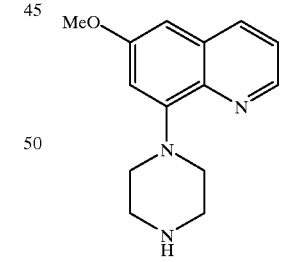
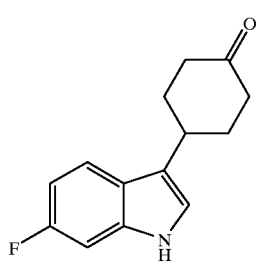 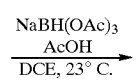
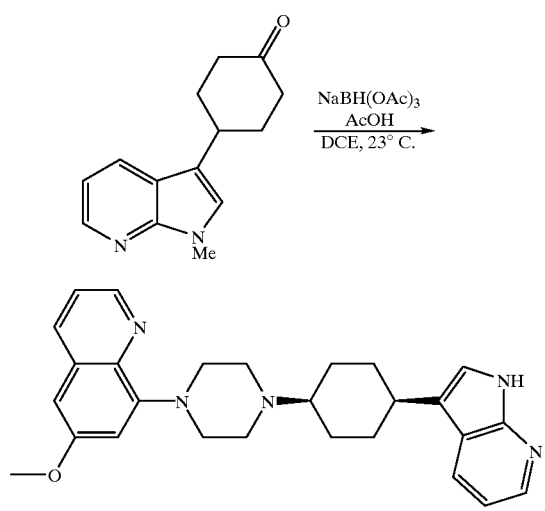

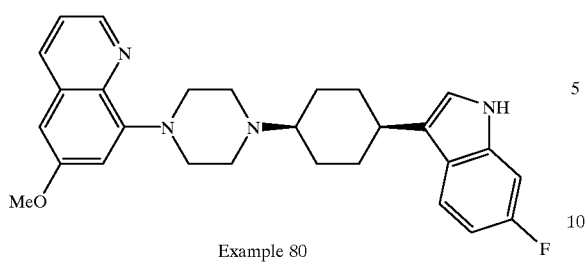
Example 80
Scheme 32
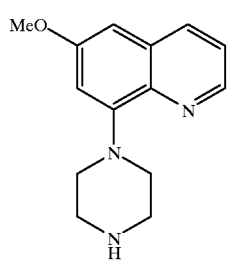
+
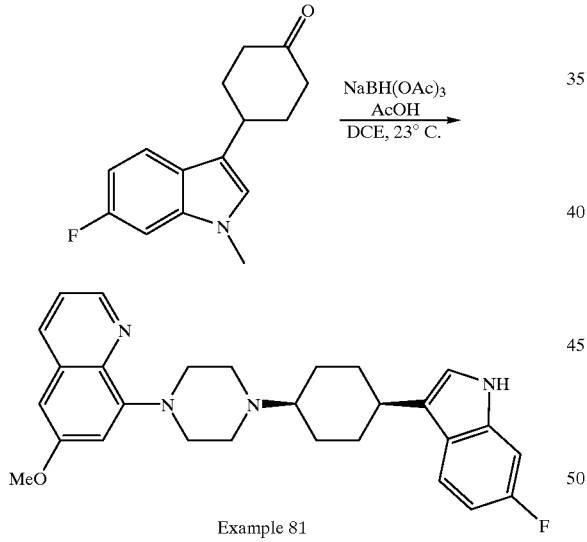
Example 81
Scheme 33
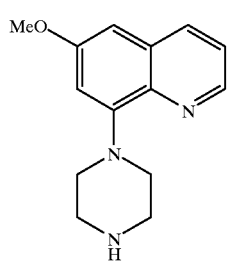
+
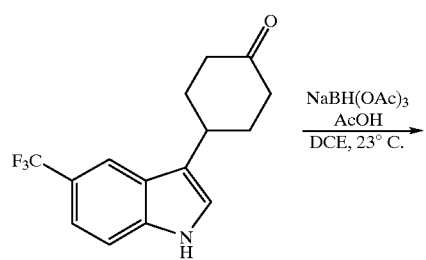
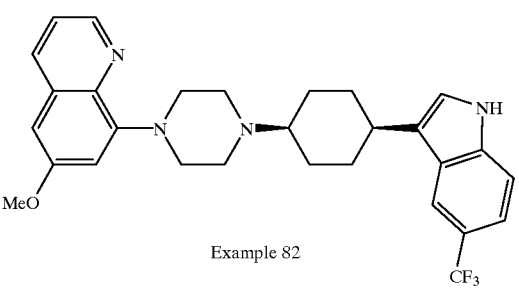
Example 82
Scheme 34
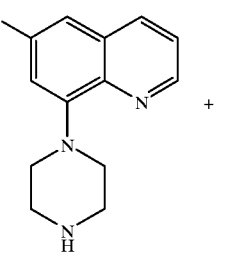
+
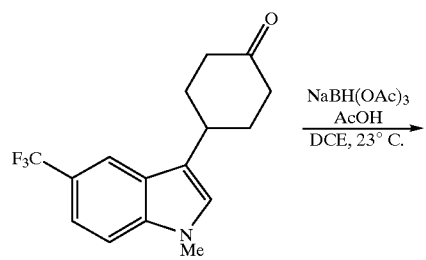

Scheme 36
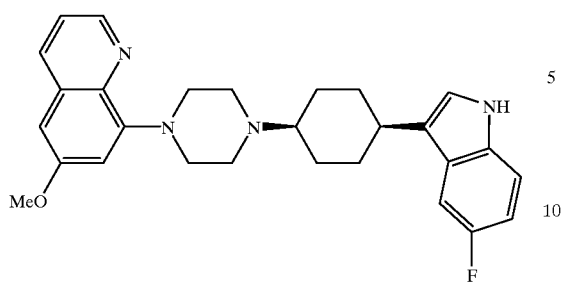
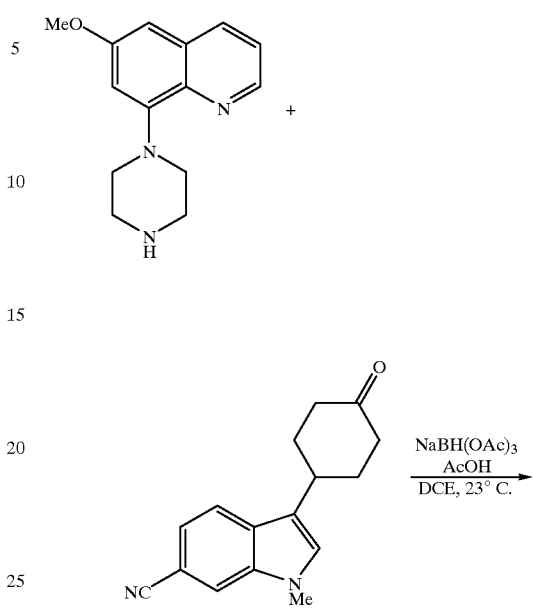
Example 83
Scheme 35
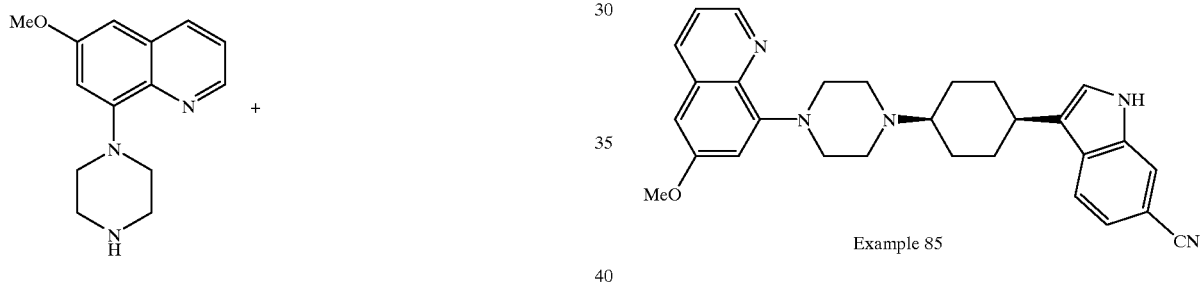
Example 85
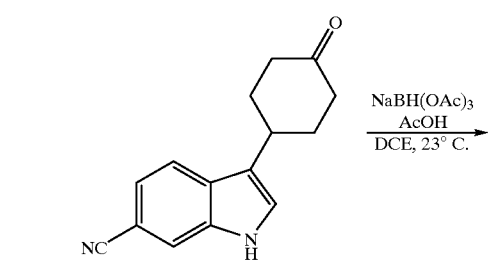
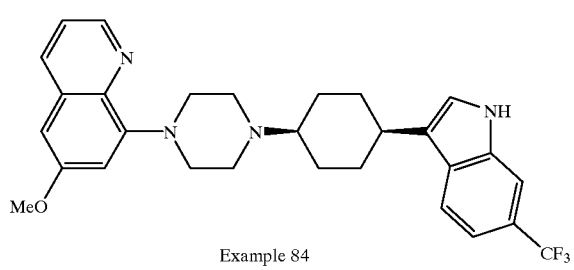
Example 84
The following Schemes 37–39 were utilized to obtain the compounds of Examples 86–114.
Scheme 37
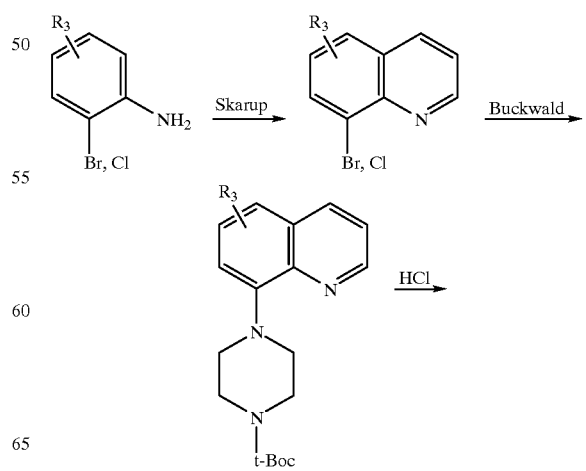

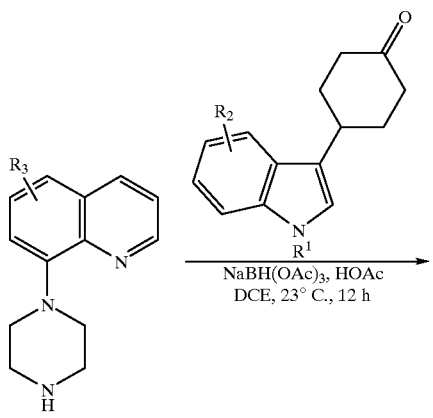
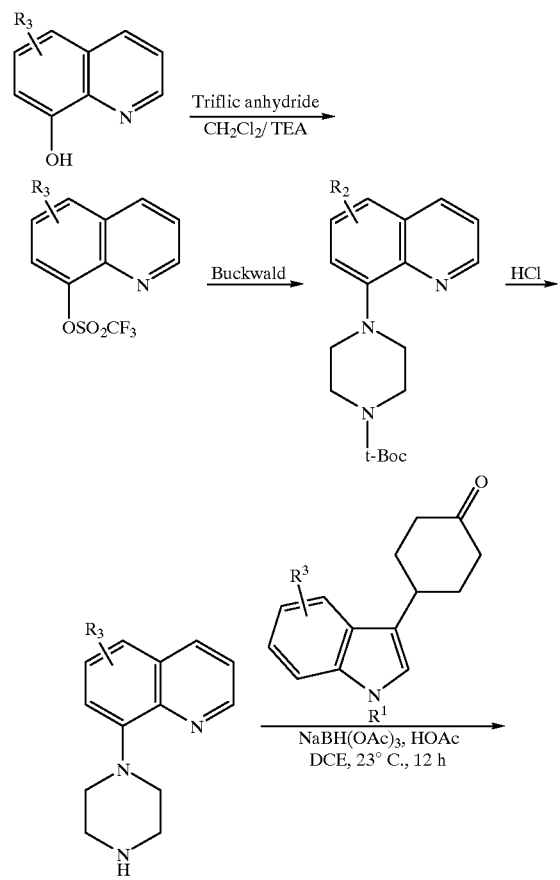
Scheme 38
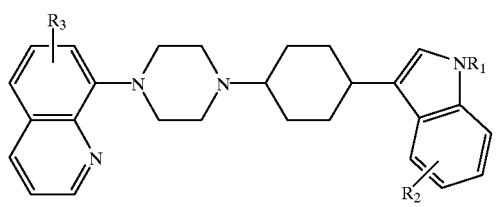
when $R_3$ is 5-Cl
when $R_3$ is 5-F
$R_1$ is H, CH3
$R_2$ is 5-F, 6-F, 5-CN
Scheme 39
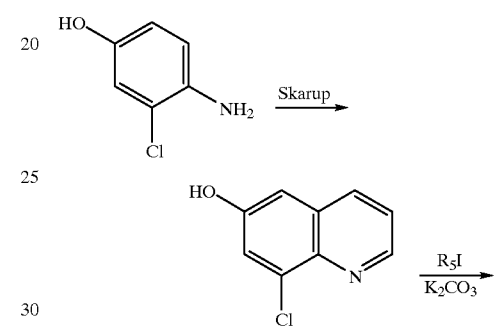
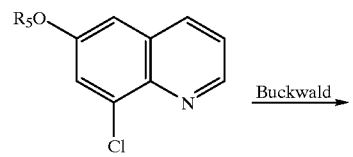
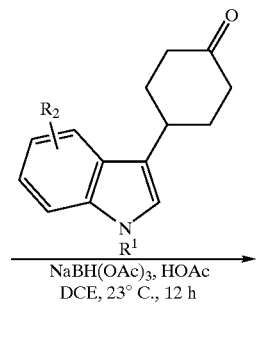

-continued

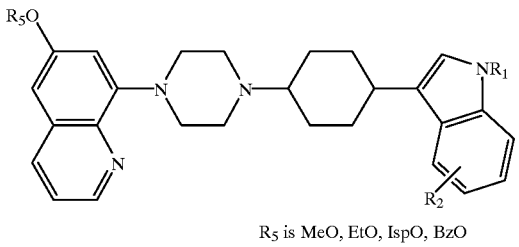

R₁ is H, CH3
R₂ is 5-F, 6-F, 5-CN, 5-CH₃O-, 5-OBz

R₅ is MeO, EtO, IspO, BzO

INTERMEDIATE 1

3-(1,4-Dioxa-spiro[4,5]dec-7-en-8-yl)-1H-indole (1a)

Indole (4.69, 40 mmol), 1,4-cyclohexanedione monoethylene ketal (6.3 g, 40 mmol) and potassium hydroxide (13.2 g, 200 mmol) were heated to reflux in 70 ml methanol for 6 hours. The reaction was cooled and the product was isolated by filtration and washed with water to give 9.1 g (89%) of product.

3-(1,4-Dioxa-spiro[4,5]dec-7-en-8-yl)-4-fluoro-1H-indole (1b)

This compound was prepared in a similar fashion described above by replacing indole with 4-fluoroindole (3 g, 22 mmol) to afford the title compound in quantitative yield as a white solid: mp at 140° C. (sublimated).

3-(1,4-Dioxa-spiro[4,5]dec-7-en-8-yl)-5-fluoro-1H-indole (1c)

5-Fluoroindole (4.96 g, 0.036 mol), 1,4-cyclohexanedione monoethylene ketal (7.17 g, 0.046 mol) and potassium hydroxide (6 g, 91 mmol) were heated to reflux in 70 ml methanol for 6 hours. The reaction was cooled and the product was isolated by filtration and washed with water to give 8.59 g (86%) of product as a white solid: mp 153–155° C.

3-(1,4-Dioxa-spiro[4,5]dec-7-en-8-yl)-6-fluoro-1H-indole (1d)

This compound was prepared in the manner described for intermediate 1a by replacing indole with 6-fluoroindole (5.14 g, 38 mmol) ) to afford 10 g (96.3%) of the title compound as a white solid: mp 196–197° C.

Elemental analysis for $C_{16}H_{16}FNO2$; Calc'd: C, 70.32; H, 5.90; N, 5.13; Found: C, 70.62; H, 5.91; N, 5.08.

3-(1,4-Dioxa-spiro[4,5]dec-7-en-8-yl)-5-bromo-1H-indole (1e)

This compound was prepared in the manner described above for intermediate 1a by replacing indole with 5-bromoindole (7.84 g, 40 mmol) ) to afford 10.5 g (78%) of the title compound as a white solid; MS EI m/e 333 (M⁺).

3-(1,4-Dioxa-spiro[4,5]dec-7-en-8-yl)-5-chloro-1H-indole (1f)

This compound was prepared in the manner described above for intermediate 1a by replacing indole with 5-chloroindole (5 g, 33 mmol) ) to afford 9.14 g (96%) of the title compound as a white solid: mp 178–181° C.; MS EI m/e 273 (M⁺).

3-(1,4-Dioxa-spiro[4,5]dec-7-en-8-yl)-5-cyano-1H-indole (1g)

This compound was prepared in the manner described above for intermediate 1a by replacing indole with 5-cyanoindole (29.98 g, 0.21 mol) to afford 29.32 g (50%) of the title compound as a white solid: mp 158–160° C.

3-(1,4-Dioxa-spiro[4,5]dec-7-en-8-yl)-5-methoxy-1H-indole (1h)

This compound was prepared in the manner described above for intermediate 1a by replacing indole with 5 methoxy indole (5 g, 34 mmol) in 82% yield (7.95 g) as a white solid: mp 161–162° C.

3-(1,4-Dioxa-spiro[4,5]dec-7-en-8-yl)-2-methyl-1H-indole (1i)

A solution of 2-methyl-indole (2.0 g, 15.2 mmol), 1,4-cyclohexanedione monoethylene ketal (4.76 g, 30.4 mmol) and potassium hydroxide (10 g, 0.18 mol) were heated to reflux in 50 ml methanol for 48 hours. The mixture was poured into water (150 ml) and extracted with methylene chloride (2×200 ml). The organic layer was dried over anhydrous magnesium sulfate, filtered, and solvent was removed under vacuum. Chromatography (25% ethyl acetate-hexanes) afforded a light tan solid which was washed with ethyl ether (20 ml) to afford 2.35 g (62%) of product as a white solid: mp 136–137° C.

Elemental analysis for $C_{17}H_{19}NO_2$; Calc'd: C, 75.81; H, 7.11; N, 5.70; Found: C, 75.47; H, 7.26; N, 5.13.

3-(1,4-Dioxa-spiro[4,5]dec-7-en-8-yl)-1H-azaindole (1j)

This compound was prepared in the manner described above for intermediate 1a by replacing indole with 7-azaindole (3.65 g, 31 mmol) in 68% yield (5.42 g) as a white solid: mp 162–165° C.; MS EI m/e 256 (M⁺).

INTERMEDIATE 2

3-(1,4-Dioxa-spiro[4,5]dec-8-yl)-1H-indole (2a)

A mixture of 3-(1,4-dioxa-spiro[4,5]dec-7-en-8-yl)-1H-indole (8.0 g, 31.3 mmol) and 10% palladium on carbon (1.3 g) in ethanol (700 ml) was hydrogenated for 18 hours. The catalyst was filtered off and the solvent removed under vacuum to afford 8.01 g (99%) of product as a white solid.

3-(1,4-Dioxa-spiro[4,5]dec-8-yl)-4-fluoro-1H-indole (2b)

This compound was prepared in the manner described above for intermediate 2a by replacing 3-(1,4-dioxa-spiro [4,5]dec-7-en-8-yl)-1H-indole with 3-(1,4-dioxa-spiro[4,5] dec-7-en-8-yl)-4-fluoro-1H-indole (6.3 g) ) to afford 4.44 g (70%) of the title compound as a white solid: mp 161–162° C.

Elemental analysis for $C_{16}H_{18}FNO_2$; Calc'd: C, 69.08; H, 6.59; N, 5.09; Found: C, 69.05; H, 6.56; N, 4.87.

3-(1,4-Dioxa-spiro[4,5]dec-8-yl)-5-fluoro-1H-indole (2c)

A mixture of of 3-(1,4-dioxa-spiro[4,5]dec-7-en-8-yl)-5-fluoro-2H-indole (8.5 g) and 10% palladium on carbon (2.72 g) in ethanol (200 ml) was hydrogenated for 5 hours. The catalyst was filtered off and the solvent removed under vacuum. Chromatography (methanol-methylene chloride) afforded 7.55 g (82%) of product as a white solid: mp 183–185° C.

3-(1,4-Dioxa-spiro[4,5]dec-8-yl)-6-fluoro-1H-indole (2d)

This compound was prepared in the manner described above for intermediate 2a by replacing 3-(1,4-dioxa-spiro[4,5]dec-7-en-8-yl)-1H-indole with 3-(1,4-dioxa-spiro[4,5]dec-7-en-8-yl)-6-fluoro-1H-indole (9.54 g) to afford 5.83 g (60%) of the title compound as a white solid: mp 158–159° C.

Elemental analysis for $C_{16}H18FNO_2$; Calc'd: C, 69.80; H, 6.59; N, 5.09; Found: C, 69.74; H, 6.48; N, 5.13.

3-(1,4-Dioxa-spiro[4,5]dec-8-yl)-5-bromo-1H-indole (2e)

A mixture of 3-(1,4-dioxa-spiro[4,5]dec-7-en-8-yl)-5-bromo-1H-indole (6.8 g, 20.34 mmol) and 5% platinum on carbon (5.0 g) in ethanol (500 ml) was hydrogenated overnight. The catalyst was filtered off and the solvent removed under vacuum. Chromatography (30% ethyl acetate-hexanes) afforded 5.0 g (73%) of product as a solid; MS EI m/e 336 (M⁺).

3-(1,4-Dioxa-spiro[4,5]dec-8-yl)-5-chloro-1H-indole (2f)

A mixture of 3-(1,4-dioxa-spiro[4,5]dec-7-en-8-yl)-5-chloro-1H-indole (0.18 g) and platinum oxide (0.02 g) in ethanol (20 ml) with ten drops of acetic acid was hydrogenated overnight. The catalyst was filtered off and the solvent removed under vacuum. Chromatography (25% ethyl acetate-hexanes) afforded 0.16 g (88%) of product as a white solid: mp 205–206.5° C.

3-(1,4-Dioxa-spiro[4,5]dec-8-yl)-5-cyano-1H-indole (2g)

This compound was prepared in the manner described above for intermediate 2a by replacing 3-(1,4-dioxa-spiro[4,5]dec-7-en-8-yl)-1H-indole with 3-(1,4-dioxa-spiro[4,5]dec-7-en-8-yl)-5-cyano-1H-indole (54.6 g) ) to afford 52.12 g (95%) of the title compound as a white solid in 95% (52.12 g) yield as a white solid: mp 153–155° C.

3-(1,4-Dioxa-spiro[4,5]dec-8-yl)-5-methoxy-1H-indole (2h)

This compound was prepared in the manner described above for intermediate 2a by replacing 3-(1,4-dioxa-spiro[4,5]dec-7-en-8-yl)-1H-indole with 3-(1,4-dioxa-spiro[4,5]dec-7-en-8-yl)-5-methoxy-1H-indole to afford 7.18 g (96%) of the title compound as a white solid: mp 153–155° C.

3-(1,4-Dioxa-spiro[4,5]dec-8-yl)-2-methyl-1H-indole (2i)

A mixture of 3-(1,4-dioxa-spiro[4,5]dec-7-en-8-yl)-2-methyl-1H-indole (2.39 g, 8.9 mmol) and 10% palladium on carbon (0.35 g) in ethanol (80 ml) was hydrogenated for 3 hours. The catalyst was filtered off and then a solution of methylene-methanol (80 ml) was used to dissolve any solids within the celite. The solvent removed under vacuum to afford 2.34 g (97%) of product as an off-white solid, which was triturated with ethyl ether (40 ml) to afford a white solid: mp 166–168° C. The mother liquor was concentrated to afford another 1.2 g of product as a yellow solid.

Elemental analysis for $C_{17}H_{21}NO_2$; Calc'd: C, 75.25; H, 7.80; N, 5.16; Found: C, 75.17; H, 7.99; N, 5.12.

3-(1,4-Dioxa-spiro[4,5]dec-8-yl)-1H-azaindole (2j)

This compound was prepared in the manner described above for intermediate 2a by replacing 3-(1,4-dioxa-spiro[4,5]dec-7-en-8-yl)-1H-indole (7.18 g) with 3-(1,4-dioxa-spiro[4,5]dec-7-en-8-yl)-1H-azaindole (4.02 g) to afford 2.7 g (67%) of the title compound as a white solid: mp 204–207° C.

Elemental analysis for $C_{13}H_{14}N_2O$; Calc'd: C, 72.87; H, 6.59; N, 13.07; Found: C, 72.44; H, 6.75; N, 12.81.

INTERMEDIATE 3

4-(1H-3-Indolyl)-cyclohexanone (3a)

A solution of 3-(1,4-dioxa-spiro[4,5]dec-8-yl)-1H-indole (2.57 g, 10 mmol) in 200 ml (1:1) tetrahydrofuran-hydrochloric acid (1N) was allowed to stir at room temperature for 16 hours. The solvent was evaporated under vacuum. The crude product was dissolved in ethyl acetate, washed with 1N sodium hydroxide (3×150 ml). The organic layer was dried over anhydrous sodium sulfate, and filtered. Chromatography (40% ethyl acetate-hexanes) afforded 1.9 g (89%) of product.

4-(4-Fluoro-1H-3-indolyl)-cyclohexanone (3b)

This compound was prepared in the manner described above for 3a by replacing 3-(1,4-dioxa-spiro[4,5]dec-8-yl)-1H-indole with 3-(1,4-dioxa-spiro[4,5]dec-8-yl)-4-fluoro-1H-indole (4.0 g) to afford 3.7 g (63%) of the title compound as a white solid: mp 104–106° C.

4-(5-Fluoro-1H-3-indolyl)-cyclohexanone (3c)

A solution of 3-(1,4-dioxa-spiro[4,5]dec-8-yl)-5-fluoro-1H-indole (2.8 g, 10 mmol) in 200 ml(1:1) tetrahydrofuran-hydrochloric acid (1N) was allowed to stir at room temperature for 16 hours. The solvent was evaporated under vacuum. The crude product was dissolved in ethyl acetate, washed with 1N sodium hydroxide (3×150 ml). The organic layer was dried over anhydrous sodium sulfate, and filtered. Chromatography (40% ethyl acetate-hexanes) afforded 2.1 g (91%) of product as yellow solid: mp 112–114° C.

4-(6-Fluoro-1H-3-indolyl)-cyclohexanone (3d)

This compound was prepared in the manner described above for intermediate 3a by replacing 3-(1,4-dioxa-spiro[4,5]dec-8-yl)-1H-indole with 3-(1,4-dioxa-spiro[4,5]dec-8-yl)-6-fluoro-1H-indole (5.4 g) to afford 19.29 g (99%) of the title compound as a white solid: mp 102–105° C.

Elemental analysis for $C_{14}H_{14}NOF$; Calc'd: C, 72.71; H, 6.10; N, 6.06; Found: C, 72.77; H, 5.98; N, 5.96.

4-(5-Bromo-1H-3-indolyl)-cyclohexanone (3e)

This compound was prepared in the manner described above for intermediate 3a by replacing 3-(1,4-dioxa-spiro[4,5]dec- 8-yl)-1H-indole with 3-(1,4-dioxa-spiro[4,5]dec-8-yl)-5-bromo-1H-indole (4.5 g) to afford 3.3 g (84%) of the title compound as a white solid: MS EI m/e 291 (M⁺).

Calc'd: C, 75.25; H, 7.80; N, 5.16; Found: C, 75.17; H, 7.99; N, 5.12.

4-(5-Chloro-1H-3-indolyl)-cyclohexanone (3f)

This compound was prepared in the manner described above for intermediate 3a by replacing 3-(1,4-dioxa-spiro[4,5]dec-8-yl)-1H-indole with 3-(1,4-dioxa-spiro[4,5]dec-8-yl)-5-chloro-1H-indole (2.12 g) to afford 1.13 g (60%) of the title compound as a clear oil: MS FAB m/e 248 (M+H)⁺.

4-(5-Cyano-1H-3-indolyl)-cyclohexanone (3g)

This compound was prepared in the manner described above for intermediate 3a by replacing 3-(1,4-dioxa-spiro

[4,5]dec-8-yl)-1H-indole with 3-(1,4-dioxa-spiro[4,5]dec-8-yl)-5-cyano-1H-indole (6 g) to afford 4.03 g (81%) of the title compound as a white solid: mp 162.5–164° C.

Elemental analysis for $C_{15}H_{14}N_2O$; Calc'd: C, 75.61; H, 5.92; N, 11.76; Found: C, 75.82; H, 6.06; N, 11.72.

4-(5-Methoxy-1H-3-indolyl)-cyclohexanone (3h)

This compound was prepared in the manner described above for intermediate 3a by replacing 3-(1,4-dioxa-spiro[4,5]dec-8-yl)-1H-indole with 3-(1,4-dioxa-spiro[4,5]dec-8-yl)-5-methoxy-1H-indole (5.85 g) to afford 4.2 g (85%) of the title compound as a white solid: mp 103–106° C.

4-(2-Methyl-1H-3-indolyl)-cyclohexanone (3i)

This compound was prepared in the manner described above for intermediate 3a by replacing 3-(1,4-dioxa-spiro[4,5]dec-8-yl)-1H-indole with 3-(1,4-dioxa-spiro[4,5]dec-8-yl)-2-methyl-1H-indole (2.2 g) to afford 1.62 g (88%) of the title compound as a yellow thick oil: MS EI m/e 227 (M$^+$).

4-(1H-3-pyrrolo[2,3-b]pyridyl)-cyclohexanone (3j)

This compound was prepared in the manner described above for intermediate 3a by replacing 3-(1,4-dioxa-spiro[4,5]dec-8-yl)-1H-indole with 3-(1,4-dioxa-spiro[4,5]dec-8-yl)-1H-azaindole (2.48 g) to afford 1.96 g (95%) of the title compound as a white solid: mp 162–164° C.

INTERMEDIATE 4

3-(1,4-Dioxa-spiro[4,5]dec-7-en-8-yl)-5-cyano-1-methyl-indole

To a suspension of sodium hydride (60%, 1.74 g, 0.073 mol) in anhydrous N,N-dimethylformamide (100 ml) was added 3-(1,4-dioxa-spiro[4,5]dec-7-en-8-yl)-5-cyano-1H-indole (9.9 g, 0.035 mol) at room temperature. The mixture was stirred for 30 minutes at room temperature, then methyl iodide (9 ml, 0.14 mol) was added at room temperature. The reaction was allowed to stir for 1 hour, then quenched with water (50 ml). The mixture was extracted with methylene chloride (3×150 ml) and water (3×150 ml). The organic layer was dried over anhydrous magnesium sulfate and filtered. The solvent was removed under vacuum. Chromatography (5% methanol-methylene chloride) afforded 2.54 g (24%) of product as a light yellow solid: mp 65–67° C.

Elemental analysis for $C_{18}H_{18}N_2O_2$; Calc'd: C, 73.45; H, 6.16; N, 9.52; Found: C, 73.17; H, 6.24; N, 9.43.

INTERMEDIATE 5

3-(1,4-Dioxa-spiro[4,5]dec-8-yl)-5-cyano-1-methyl-indole (5a)

A mixture of 3-(1,4-dioxa-spiro[4,5]dec-7-en-8-yl)-5-bromo-1H-indole (3.77 g) and 10% palladium on carbon (0.99 g) in ethanol-tetrahydrofuran (200:80 ml) was hydrogenated for 5 hours. The catalyst was filtered off and the solvent was removed under vacuum to afford a white powder which was washed with ethanol-hexanes (1:1) and dried under vacuum for 4 hours to afford 2.75 g (12%) of product: mp 170–172° C.

Elemental analysis for $C_{18}H_{20}N_2O_2$; Calc'd: C, 72.95; H, 6.80; N, 9.45; Found: C, 72.79; H, 6.82; N, 9.35.

3-(1,4-Dioxa-spiro[4,5]dec-8-yl)-5-cyano-1-ethyl-indole (5b)

To a suspension of sodium hydride (60%, 1.63 g, 0.068 mol) in anhydrous N,N-dimethylformamide (150 ml) was added 3-(1,4-dioxa-spiro[4,5]dec-8-yl)-5-cyano-1H-indole (9.0 g, 0.032 mol) at room temperature. The mixture was stirred for 30 minutes at room temperature then ethylbromide (14.6 g, 0.13 mol) was added at room temperature. The reaction was allowed to stir for overnight, then quenched with water (50 ml). The mixture was extracted with methylene chloride (3×150 ml) and water (3×150 ml). The organic layer was dried over anhydrous magnesium sulfate and filtered. The solvent was removed under vacuum. Chromatography (hexanes) afforded 5.5 g (69%) of product as a white solid: mp 124–126° C.

Elemental analysis for $C_{19}H_{20}N_2O_2$; Calc'd: C, 73.52; H, 7.14; N, 9.02; Found: C, 73.56; H, 6.93; N, 8.95.

3-(1,4-Dioxa-spiro[4,5]dec-8-yl)-5-cyano-1-n-propyl-indole (5c)

This compound was prepared in the manner described above for intermediate 5b by replacing ethylbromide with n-propylbromide (13.1 g, 11 mmol) to afford 4.33 g (75%) of the title compound as a oil: MS EI m/e 324 (M$^+$)

3-(1,4-dioxa-spiro[4,5]dec-8-yl)-5-cyano-1-iso-propyl-indole (5d)

This compound was prepared in the manner described above for intermediate 5b by replacing ethylbromide with isopropylbromide (10.2 g, 83 mmol) in 62% yield (6.44 g) as a white solid: mp 114.5–116° C.; MS EI m/e 324 (M$^+$)

3-(1,4-dioxa-spiro[4,5]dec-8-yl)-5-cyano-1-benzyl-indole (5e)

This compound was prepared in the manner described above for intermediate 5b by replacing ethylbromide with benzylbromide (14.3 g, 84 mmol) to afford 6.04 g (57%) of the title compound as a white solid: mp 129–130° C.

Elemental analysis for $C_{23}H_{24}N_2O_2$; Calc'd: C, 77.39; H, 6.50; N, 7.52; Found: C, 76.59; H, 6.28; N, 7.47.

INTERMEDIATE 6

4-(5-Cyano-1-methyl-3-indolyl)-cyclohexanone (6a)

A solution of 3-(1,4-dioxa-spiro[4,5]dec-8-yl)-5-cyano-1-methyl-indole (5.5 g) in 150 ml (1:1) tetrahydrofuran-hydrochloric acid (1N) was allowed to stir at room temperature for 16 hours, followed by the addition of 4.49 g sodium bicarbonate. The mixture was extracted with methylene chloride (3×100 ml), washed with brine (3×150 ml). The organic layer was dried over anhydrous magnesium sulfate and filtered. The solvent was removed to afford a light brown solid which was boiled in ethyl acetate-hexanes (1:1). The mixture was cooled to room temperature and solid was collected and dried under vacuum to afford 2.06 g of the title compound as a solid: mp 150–152° C.

Elemental analysis for $C_{15}H_{15}N_2O$; Calc'd: C, 76.16; H, 6.39; N, 11.10; Found: C, 75.84; H, 6.34; N, 10.92.

4-(5-Cyano-1-ethyl-3-indolyl)-cyclohexanone (6b)

This compound was prepared in the manner described above for intermediate 6a by replacing 3-(1,4-dioxa-spiro[4,5]dec-8-yl)-5-cyano-1-methyl-indole with 3-(1,4-dioxa-spiro[4,5]-dec-8-yl)-5-cyano-1-ethyl-indole (6.77 g, 22 mmol) to afford 4.33 g (75%) of the title compound as a white solid: mp 124° C.

Elemental analysis for $C_{17}H_{18}N_2O$; Calc'd: C, 76.66; H, 6.81; N, 10.52; Found: C, 76.30; H, 6.82; N, 10.25.

4-(5-Cyano-1-n-propyl-3-indolyl)-cyclohexanone (6c)

This compound was prepared in the manner described above for intermediate 6a by replacing 3-(1,4-dioxa-spiro[4,5]dec-8-yl)-5-cyano-1-methyl-indole with 3-(1,4-dioxa-spiro[4,5]-dec-8-yl)-5-cyano-1-n-propyl-indole (2.64 g, 8.2 mmol) to afford 1.67 g (73%) of the title compound as a white solid: mp 103–104° C.; MS EI m/e 280 (M$^+$).

4-(5-Cyano-1-benzyl-3-indolyl)-cyclohexanone (6d)

This compound was prepared in the manner described above for intermediate 6a by replacing 3-(1,4-dioxa-spiro[4,5]dec-8-yl)-5-cyano-1-methyl-indole with 3-(1,4-dioxa-spiro[4,5]-dec-8-yl)-5-cyano-1-benzyl-indole (6.43 g, 20 mmol) to afford 3.49 g (63%) of the title compound as a white solid: mp 115–126° C.

Elemental analysis for $C_{22}H_{20}N_2O$; Calc'd: C, 80.46; H, 6.14; N, 8.53; Found: C, 80.42; H, 6.07; N, 8.49.

4-(5-Cyano-1-isopropyl-3-indolyl)-cyclohexanone (6e)

This compound was prepared in the manner described above for intermediate 6a by replacing 3-(1,4-dioxa-spiro[4,5]dec-8-yl)-5-cyano-1-methyl-indole with 3-(1,4-dioxa-spiro[4,5]-dec-8-yl)-5-cyano-1-isopropyl-indole (5.86 g, 16 mmol) to afford 3.46 g (63%) of the title compound as a white solid: mp 106–107° C.

Elemental analysis for $C_{18}H_{20}N_2O$; Calc'd: C, 77.11; H, 7.19; N, 9. Found: C, 76.85; H, 7.16; N, 9.

INTERMEDIATE 7

8-(4-Benzyl-piperazin-1-yl)quinoline

A solution of 8-amino-quinoline (12.91 g, 89 mmol) and bis(2-chloroethyl)-benzylamine (25.95 g, 112 mmol) in n-butanol (65 ml) was allowed to heat at 85° C. for 11 hours. The mixture was poured into 50% sodium hydroxide, extracted with methylene chloride and water. The organic layer was dried over anhydrous magnesium sulfate, and filtered. The solvent was removed under vacuum. Chromatography (methanol-methylene chloride) afforded 12.34 g of product as a solid: mp 116.5–118° C.

The HCl salt was prepared in ethyl acetate: mp 209–210° C. Elemental analysis for $C_{20}H_{21}N_3 \cdot 2HCl \cdot 0.5HO_2$; Calc'd: C, 62.34; H, 6.28; N, 10.91; Found: C, 62.37; H, 6.55; N, 10.80.

INTERMEDIATE 8

8-(Piperazin-1-yl)-quinoline

To a solution of 8-(4-benzyl-piperazin-1-yl)quinoline (2.63 g, 8.7 mmol) in methylene chloride (30 ml) was added vinyl chloroformate (1.1 ml, 13 mmol) at room temperature slowly. The reaction mixture was refluxed for 2 hours, and then concentrated under vacuum. The residue was dissolved in 12 N hydrochloric acid (20 ml) and stirred at room temperature for 1 hour. The mixture was concentrated, the residue was taken up with 40 ml ethanol and heated up to 50° C. for 2 hours. The solvent was removed under vacuum, the residue was dissolved in 1 N sodium hydroxide-ethyl acetate and extracted with ethyl acetate and washed with water. The organic layer was dried over anhydrous sodium sulfate. The solvent was removed under vacuum. Chromatography (10–30% methanol -methylene chloride plus ammonium hydroxide) afforded 1.86 g (90%) yellow oil; MS EI m/e 213 (M)$^+$.

INTERMEDIATE 9

6-Fluorochroman

A mixture of 6-fluoro-4-oxo-chroman (2 g, 12 mmol) and 10% palladium on carbon (1 g) in concentrated hydrochloric acid (20 ml) and ethanol (30 ml) was hydrogenated for 20 hours. The catalyst was filtered and the solvent removed under vacuum. The residue was dissolved in ethyl acetate (100 ml), washed with IN NaOH (6×200 ml) and water (3×150 ml), dried over anhydrous sodium sulfate, filtered and the solvent was removed under vacuum. Chromatography (20% ethyl acetate-hexanes) afforded 1.41 g (77%) of product as a clear oil; MS EI m/e 152 (M$^+$).

INTERMEDIATE 10

6-Fluoro-8-nitrochroman

A mixture of nitric acid (100%, 7.8 ml, 0.16 mol) in acetic anhydride was maintained at room temperature for 0.5 hour. This mixture was added to a solution of 6-fluorochroman (11.9 g, 0.078 mol) in 40 ml acetic anhydride at 0C. The reaction mixture was stirred at room temperature for 2 hours then poured into ice-water. The mixture was extracted with methylene chloride (3×60 ml) and washed with saturated sodium carbonate (8×150 ml). The organic layer was dried over anhydrous sodium sulfate and filtered. The solvent was removed under vacuum to afford a yellow solid: mp 48–50° C.

Elemental analysis for $C_9H_8FNO_3$; Calc'd: C, 54.83; H, 4.09; N, 7.10. Found: C, 54.78; H, 3.93; N, 6.09.

INTERMEDIATE 11

6-Fluoro-8-aminochroman

A mixture of 6-fluoro-8-nitrochroman (14.4 g) and 10% palladium on carbon (2 g) in ethanol (160 ml) was hydrogenated for 2 hours. The catalyst was filtered off and the solvent removed under vacuum. Chromatography (30% ethyl acetate-hexanes) afforded 12.12 g (100%) of product as a clear oil; MS EI m/e 167 (M$^+$).

INTERMEDIATE 12

1-Benzyl-4-(6-fluoro-chroman-8-yl)-piperazine

A solution of 6-fluoro-8-aminochroman (1.24 g, 7.4 mmol) and bis(2-chloroethyl)-benzylamine (2.58 g, 11 mmol) in butanol (20 ml) was stirred at 100° C. for 10 hours. The mixture was poured into saturated sodium carbonate (950 ml) and extracted with ethyl acetate (3×60 ml). The organic layer was dried over anhydrous sodium sulfate and filtered. Chromatography (20% ethyl acetate-hexanes) afforded 1.64 g (68%) of product as an oil; MS EI m/e 326 (M)$^+$.

INTERMEDIATE 13

4-(6-Fluoro-chroman-8-yl)-piperazine

A mixture of 1-benzyl-4-(6-fluoro-chroman-8-yl)-piperazine (1.64 g, 5 mmol), 10% palladium on carbon (0.4 g) and ammonium formate (0.64 g, 10 mmol) in ethanol (20 ml) was allowed to refux for 2 hours. The catalyst was filtered off and the solvent removed under vacuum. Chromatography (10–20% methanol-methylene chloride plus ammonium hydroxide) afforded 1.0 g (84%) of product as a yellow oil; MS EI m/e 296 ($M^+$).

INTERMEDIATE 14

2-(4-Fluorophenoxy)-acetaldehyde diethyl acetal

To a suspension of sodium hydride (5.4 g, 0.134 mol) in anhydrous N,N-dimethylformamide (100 ml) was added 4-fluorophenol (10 g, 0.089 mol) at 0° C. After hydrogen evolution had ceased, bromo-acetaldehyde diethyl acetal (16 ml, 0.11 mol) was added. The reaction was heated at 160–170° C. for 18 hours. The mixture was poured into ice-water, extracted with ethyl acetate (3×150 ml), washed with 1N sodium hydroxide (3×100 ml), and brine (3×100 ml). The organic layer was dried over anhydrous sodium sulfate and filtered. The solvent was removed under vacuum. Chromatography (25% ethyl acetate-hexanes) afforded 16.36 g (80%) of product as a clear oil: MS EI m/e 228 ($M^+$).

INTERMEDIATE 15

5-Fluorobenzofuran

To a mixture of benzene (200 ml) containing polyphosphoric acid (7.9 g, 0.035 mol) was added 2-(4-fluorophenoxy)-acetaldehyde diethyl acetal (8 g, 0.035 mol). The mixture was stirred vigorously while being heated to reflux for 2.5 hours. The reaction mixture was cooled to room temperature and decanted from the polyphosphoric acid. The solvent was removed under vacuum. Chromatography (5% ethyl acetate-hexanes) afforded 3.4 g (45%) of product as a clear oil: $^1$H NMR (CDCl$_3$) δ 6.74 (dd, 1H, J=2.0, 0.6 Hz), 7.01 (td, 1H, J=9, 2.7 Hz), 7.25 (dd, 1H, J=8.4, 2.7 Hz), 7.43 (dd, 1H, J=9, 3.9 Hz), 7.65 (d, 1H, J=1.8 Hz).

INTERMEDIATE 16

5-Fluoro-2,3-dihydrobenzofuran

A solution of 5-fluorobenzofuran and 10% palladium on carbon in acetic acid (25 ml) was hydrogenated under 50 psi for 12 hours. The catalyst was filtered through celite and the celite was washed with methylene chloride (200 ml). The organic layer was washed sequentially with 1N NaOH (3×100 ml), brine (3×100 ml) and dried over anhydrous sodium sulfate and filtered. The solvent was removed under vacuum to afforded 2.59 g (85%) of product as a clear oil: $^1$H NMR (300 MHz, CDCl$_3$): δ 3.12 (t, 2H, J=8.7 Hz), 4.58 (t, 2H, J=8.7 Hz), 6.68 (dd, 1H, J=Hz), 6.79 (tm, 1H, J=8.7 Hz), 6.89 (dm, 1H, J=8.1 Hz).

INTERMEDIATE 17

5-Fluoro-7-nitro-2,3-dihydrobenzofuran

A mixture of nitric acid (100%, 1.5 ml, 36 mmol) in acetic anhydride (18 ml) was maintained at room temperature for 0.5 hour. The mixture was added to a solution of 5-fluoro-2,3-dihydrobenzofuran (2.5 g, 18 mmol) in 10 ml acetic anhydride at 10° C. The reaction mixture was stirred at room temperature for 2 hours then poured into ice-water. The mixture was extracted with methylene chloride (3×60 ml), washed with 1N sodium hydroxide (5×100 ml) and brine (200 ml). The organic layer was dried over anhydrous sodium sulfate and filtered. The solvent was removed under vacuum to afford a yellow solid: mp 113–114° C.

Elemental analysis for $C_8H_6NO_3$; Calc'd: C, 52.47; H, 3.30; N, 7.65; Found: C, 52.40; H, 3.21; N, 7.39.

INTERMEDIATE 18

5-Fluoro-7-amino-2,3-dihydrobenzofuran

A mixture of 5-fluoro-7-nitro-2,3-dihydrobenzofuran (2.65 g) and 10% palladium on carbon (0.5 g) in ethanol (100 ml) was hydrogenated for 3 hours. The catalyst was filtered off and the solvent removed under vacuum. Chromatography (30% ethyl acetate-hexanes) afforded 1.38 g (62%) of product as a white solid: mp 68–70° C.

Elemental analysis for $C_8H_6NO_3$; Calc'd: C, 62.74; H, 5.27; N, 9.15; Found: C, 62.76; H, 5.32; N, 9.13.

INTERMEDIATE 19

1-Benzyl-4-(5-fluoro-2,3-dihydro-benzofuran-7-yl)-piperazine

A solution of 5-fluoro-7-amino-2,3-dihydrobenzofuran (1.38 g, 9 mmol) and bis(2-chloroethyl)-benzylamine (3.14 g, 14 mmol) in butanol (20 ml) was stirred at 100° C. for 10 hours. The salt was filtered off, washed with ethyl ether (30 ml) and dried under vacuum: mp 232–233.5° C. The salt was converted to the free base to afford 2.06 g (73%) of the title compound.

Elemental analysis for $C_{19}H_{21}$ $_{FN2}$O.HCl.0.25H$_2$O; Calc'd: C, 64.58; H, 6.42; N, 7.93; Found: C, 64.43; H, 6.27; N, 7.86.

INTERMEDIATE 20

4-(5-Fluoro-2,3-dihydro-benzofuran-7-yl)-piperazine

A mixture of 1-benzyl-4-(5-fluoro-2,3-dihydrobenzofuran-7-yl)-piperazine (2.06 g, 6.6 mmol), 10% palladium on carbon (0.6 g) and ammonium formate (0.83 g, 13 mmol) in ethanol (20 ml) was allowed to refux for 2 hours. The catalyst was filtered off and the solvent removed under vacuum. Chromatography (10–30% methanol-methylene chloride plus ammonium hydroxide) afforded 1.10 g (75%) of product as a yellow oil; MS EI m/e 222 ($M$)$^+$.

INTERMEDIATE 21

Ethyl 7-nitrobenzofuran-2-carboxylate

A stirred mixture of 2-hydroxy-3-nitrobenzaldehyde (4.8 g, 59 mmol), diethyl bromomalonate (16.8g, 71 mmol), potassium carbonate (12.1 g, 88 mmol) and N,N'-terephthalylidenebis(4-butylaniline) (1.9g, 5.9 mmol) in toluene (100 ml) was refluxed with a Dean-Stark trap for 24 hours. Another 12.1 g potassium carbonate was added to the above reaction mixture, and the resulting mixture was allow to reflux for another 3 days. The reaction was quenched with water, extracted with (3×200 ml) and washed with 2.0 N sodium hydroxide (100 ml). The organic layer was dried over anhydrous sodium sulfate and filtered. Chromatography (30% ethyl acetate-hexanes) afforded a yellow solid: mp 86.5–87.5° C. (lit$^1$: mp 88–89° C.).

INTERMEDIATE 22

7-Nitrobenzofuran

To a suspension of ethyl 7-nitrobenzofuran-2-carboxylate in ethanol was added 2 N potassium hydroxide (60 ml). After being heated at reflux for 0.5 hour, the solution was cooled to room temperature and concentrated to half volume. Concentrated hydrochloric acid was added to the above mixture and filtered. The solid was washed with water and dried under vacuum with phosphorous pentoxide overnight. The dried solid was mixed with quinoline (75 ml) and copper oxide (CuO, 0.4 g). The mixture was heated up to 220° C. for 3 hours. The mixture was filtered and the filtrate was concentrated. Chromatography (20% ethyl acetate-hexanes) afforded 5.3 g (91%) of product as a yellow solid: mp 92–94° C. (lit[1]: mp 95.5–97° C.).

INTERMEDIATE 23

7-Aminobenzofuran hydrochloride

A stirred suspension of 7-nitrobenzofuran (5.3 g, 32 mmol) and Raney nickel (0.1 g) in methanol (70 ml) was heated up to 500C. Then hydrazine monohydrate (98%, 4.8 ml, 97 mmol) in methanol (10 ml) was slowly added to the above solution at temperature 50–60° C. When the addition was complete, the mixture was allowed to reflux for 2 hours. The Raney nickel was filtered off and the solution was concentrated. The residue was dissolved in ethyl acetate and converted to its HCl salt 3.68 g (66%) (lit[1]: mp 212–213° C.).

INTERMEDIATE 24

1-(7-Benzofuranyl)piperazine

A solution of 7-aminobenzofuran hydrochloride (3.66 g, 22 mmol) and bis(2-chloroethyl)amine hydrochloride (3.84 g, 22 mmol) in chlorobenzene (80 ml) was heated to reflux for 72 hours. The solvent was removed under vacuum, the residue was dissolved in 2.5 N sodium hydroxide-methylene chloride and extracted with methylene chloride (3×100 ml). The organic layer was dried over anhydrous sodium sulfate and filtered. Chromatography (10–20% methanol-methylene chloride plus ammonium hydroxide) afforded 0.66 g (15%) of product as a brown-yellow oil; (lit[1]: for HCl salt mp 194.5–195° C.).

INTERMEDIATE 25

4-(5-Fluoro-1H-3-indolyl)-cyclohex-3-enone

This compound was prepared in the manner described above for intermediate 3c by replacing 4-(5-fluoro-1H-3-indolyl)-cyclohexanone ethylene ketal with 4-(5-fluoro-1H-3-indolyl)-cyclohex-3-enone-ethylene ketal (1.37 g) to afford 1.01 g (88%) of the title compound.

INTERMEDIATE 26

1-(2-Methoxy-phenyl)-4-(1,4-dioxa-spiro[4,5]dec-8-yl)-piperazine

A solution of 1,4-cyclohexanedione monoethylene ketal (4.68 g, 30 mmol), 1-(2-methoxy-phenyl)piperazine (5.8 g, 30 mmol), sodium triacetoxyborohydride (9 g, 42 mmol) and acetic acid (1.8 ml, 30 mmol) in 1,2-dichloroethane (8 ml) was allowed to stir at room temperature for 12 hours. The reaction was quenched with 1N sodium hydroxide (pH>9), and extracted with methylene chloride (3×100 ml). The organic layer was dried over anhydrous sodium sulfate and filtered. Chromatography (10% methanol-ethyl acetate) afforded 9.0 g (90%) of product as a semi-solid.

INTERMEDIATE 27

4-[4-(2-Methoxy-phenyl)-piperazin-1-yl]-cyclohexanone

This compound was prepared in the manner described above for intermediate 3a by replacing 3-(1,4-dioxa-spiro[4,5]dec-8-yl)-1H-indole with 1-(2-methoxy-phenyl)-4-(1,4-dioxa-spiro[4,5]dec-8-yl)-piperazine (5.0 g, 15 mmol) to afford 4.0 g (93%) of the title compound.

INTERMEDIATE 28

5-Fluoro-3-{4-[4-(2-methoxy-phenyl)-piperazin-1-yl]cyclohex-1-enyl}-1H-indole

This compound was prepared in the manner described above for intermediate 1c by replacing 1,4-cyclohexanedione monoethylene ketal with 4-[4-(2-methoxy-phenyl)-piperazin-1-yl]-cyclohexanone (1.44 g, 5 mmol). The crude mixture was used in next step without further purification.

INTERMEDIATE 29

5-Fluoro-3-{4-[4-(2-methoxy-phenyl)-piperazin-1-yl]cyclohexyl}-1H-indole

This compound was prepared in the manner described above for intermediate 2c by replacing 4-(5-fluoro-1H-3-indolyl)-cyclohex-3-en-ethylene ketal with 5-fluoro-3-{4-[4-(2-methoxy-phenyl)-piperazin-1-yl]cyclohex-1-enyl}-1H-indole (2.0 g) to afford 1.77 g (84%) of product as a mixture of cis and trans isomer.

INTERMEDIATE 30

4-(5-Fluoro-1-methyl-3-indolyl)-cyclohexanone

To a suspension of sodium hydride (60%, 0.18 g, 4.5 mmol) in anhydrous N, N-dimethylformamide (10 ml) was added 4-(5-fluoro-1H-indol-3-yl)-cyclohexanone (0.7 g, 3.0 mmol) at room temperature. The mixture was stirred for 0.5 hour, then to the above solution was added iodomethane (0.21 ml, 3.3 mmol) at room temperature. The resulting mixture was stirred for another 0.5 hour and quenched with water. The mixture was extracted with methylene chloride (3×50 ml) and the organic layer was dried over anhydrous sodium sulfate and filtered. Chromatography (30% ethyl acetate-hexanes) afforded 0.35 g (46%) of product as a yellow oil: MS EI m/e 245 (M$^+$).

INTERMEDIATE 31

5-Nitro-quinoxaline

To a room temperature solution of 3-nitro-o-phenylenediamine (10 g, 65.3 mmol) in EtOH (50 mL) was added glyoxal (40% in $H_2O$, 22.47 mL). The reaction mixture was heated at reflux 1 hour, then diluted with $H_2O$ (100 mL). The cooled mixture was extracted with $CH_2Cl_2$ (2×300 mL) and the organic layers were combined and washed again with $H_2O$ (500 mL), dried over $Na_2SO_4$ and concentrated yielding a bright orange solid which was recrystallized from EtOAc/Hexanes to give 10.96 (96%) of a tan solid mp 90–92° C.

Elemental Analysis for $C_8H_5N_3O_2$; Calc'd C, 54.86; H, 2.88, N; 23.99; Found C, 55.12; H, 3.05; N, 24.05.

INTERMEDIATE 32

5-Amino-quinoxaline

To a three neck 250 mL round bottom flask equipped with a reflux condenser and nitrogen inlet was added 5-nitro-quinoxaline (4 g, 22.8 mmol) dissolved in HOAc (60 mL). The mixture was heated to boiling, removed from heat, and solid Fe powder (3.83 g, 68.6 mmol) was added. Vigorous boiling was observed. The reaction mixture was heated at reflux 10 minutes and then poured into $H_2O$ (100 mL) and ice. The aqueous solution was filtered and basified to pH>10 with 1 M NaOH, and extracted in EtOAc (3×200 mL). The organic layers were combined, dried over $Na_2SO_4$, and concentrated. The resulting oil was purified by column chromatography (40% EtOAc/Hexanes) yielding 2.03 g (61%) of an orange solid: mp 87–90° C.

Elemental Analysis for $C_8H_7N_3$; Calc'd C, 66.19; H, 4.86; N, 28.95; Found C, 66.25; H, 4.96; N, 29.26.

INTERMEDIATE 33

1-Benzyl-4-(quinoxalin-yl)-piperazine

To a solution of 5-amino-quinoxaline (2.8 g, 19.3 mmol) in BuOH (50 mL) was added bis(2-chloroethyl)-benzlyamine (8.42 g, 38.6 mmol) and $Et_3N$ (5.34 mL, 38.6 mmol). The reaction was stirred at 100° C. overnight. A second portion of $Et_3N$ (5.34 mL, 38.6 mmol) was added and the reaction stirred at 100° C. an additional 24 hours. The cooled solution was made alkaline with 2.5 N NaOH (500 mL) and extracted into EtOAc (3×200 mL). The organic fractions were combined, dried over $Na_2SO_4$, concentrated and chromatographed (40% EtOAc/Hex) yielding 1.0 g (17%) of a gold oil.

INTERMEDIATE 34

5-(1-Piperazinyl)-quinoxaline

To a room temperature solution of 1-benzyl-4-(quinoxalin-yl)-piperazine (1.0 g, 3.3 mmol) in anhydrous $CH_2C_2$ under nitrogen was added vinyl chloroformate (0.34 mL, 3.9 mmol) drop wise. The reaction mixture was heated at reflux 2 hours. The reaction was cooled, concentrated to dryness and concentrated HCl (25 mL) and 1,4-dioxane (25 mL) were added. The resulting solution was stirred at ambient temperature overnight. The solution was basified with 2.5 N NaOH (300 mL) and extracted into EtOAc (3×200 mL). The organic layers were combined, dried over $Na_2SO_4$, concentrated and chromatographed (10% MeOH/$CH_2Cl_2/NH_4OH$) to give 450 mg (64%) of an orange solid: mp 106–108° C.: MS (+) ESI m/e 215 [M+H]$^+$.

INTERMEDIATE 35a

5-(Trifluoromethylsulfonyloxy)-quinoline

A solution of 5-hydroxy-quinoline (8 g, 55 mmol) and $K_2CO_3$ (15.2 g, 110 mmol) in anhydrous pyridine (60 mL) under nitrogen was cooled to −20° C. $Tf_2O$ (13.97 mL, 83 mmol) was added drop-wise via syringe. The reaction mixture was stirred 1 hour at −20° C. then warmed to 0° C. for 1 hour then stirred at ambient temperature for 48 hours. The reaction mixture was then poured into $H_2O$ (200 mL) and extracted in $CH_2Cl_2$ (2×200 mL). The aqueous layer was acidified with 1 N HCl (100 mL) and back extracted with $CH_2Cl_2$ (2×200 mL). The organic fractions were dried over $Na_2SO_4$, concentrated and purified by column chromatography (40% EtOAc/Hexanes) affording 13.97 g (90%) of the product as a pink oil: MS EI m/e 277 (M$^+$).

INTERMEDIATE 35b

5-(Trifluoromethylsulfonyloxy)-isoquinoline

This compound was prepared in the manner described above for Intermediate 35a by replacing 5-hydroxy-quinoline with 5-hydroxy-isoquinoline (5 g) to afford 7.71 g (79%) of the title compound as a waxy beige solid: MS ESI m/e 278 (M$^+$).

INTERMEDIATE 35c

1-(Trifluoromethylsulfonyloxy)-isoquinoline

This compound was prepared in the manner described for Intermediate 35a by replacing 5-hydroxy-quinoline with isocarbastyril (8 g) to afford 9.74 g (64%) of the title compound as a clear oil: MS EI m/e 277 (M$^+$).

INTERMEDIATE 36a

1-t-butyl-4-(5-Quinolinyl)piperazine carboxylate

To an oven-dried 100 ml flask was added $Cs_2CO_3$ (19.87 g, 61 mmol), $Pd(OAc)_2$ (0.49 g, 2.2 mmol), and BINAP (1.183 g, 1.9 mmol). The solids were flushed with $N_2$ for 10 minutes. A solution of 5-(trifluoromethylsulfonyloxy)-quinoline (12 g, 43 mmol) and 1-t-butyl-4-piperazine carboxylate (9.67 g, 52 mmol) in THF was then added slowly to the reaction flask. The reaction mixture was stirred at room temperature for 0.5 hour then at 65° C. overnight. The resulting solution was diluted with ether, filtered through a bed of celite, washed with $Et_2O$ (50 mL) and EtOAc (50 mL). The organic fractions were combined, dried over Na2SO4, filtered, and chromatographed 3 times (10% MeOH/$CH_2Cl_2$) yielding 1.57 g (12%) of pure product as a beige solid: mp 116–118° C.

Elemental Analysis for $C_{18}H_{23}N_3O_2$: Calc'd C, 68.98; H, 7.40; N, 13.41; Found C, 69.09; H, 7.33; N, 13.08.

INTERMEDIATE 36c

1-t-butyl-4-(1-Isoquinolinyl)piperazine carboxylate

This compound was prepared in the manner described above for Intermediate 36a, replacing 5-(trifluoromethylsulfonyloxy)-quinoline with 1-(trifluoromethylsulfonyloxy)-isoquinoline (9 g, 32.5 mmol) yielding 2.33 g (25%) of a waxy beige solid: mp 69–71° C.

INTERMEDIATE 37a

5-(1-Piperazinyl)-quinoline

To a solution of 1-t-butyl-4-(5-quinolinyl)piperazine carboxylate (1.57 g, 5 mmol) in $CH_2Cl_2$ (2 mL) at 0° C. was added a pre-cooled, premixed, solution of TFA (10 mL), $CH_2Cl_2$ (20 mL) and MeOH (10 drops). The reaction was warmed slowly to room temperature and allowed to stir overnight. The resulting solution was concentrated, dissolved in $H_2O$ (5 mL) and $CH_2Cl_2$ (5 mL) and made alkaline with $NaHCO_3$ to pH 9. The aqueous portion was extracted 6×100 mL EtOAc and concentrated yielding 1.0 g (100%) of a yellow oil which solidified upon standing was not purified further.

INTERMEDIATE 37c

1-(1-piperazinyl)-isoquinoline

This compound was prepared in the same manner as intermediate 37a replacing 1-t-butyl-4-(5-quinolinyl) piperazine carboxylate with 1-t-butyl-4-(1-isoquinolinyl) piperazine carboxylate (2.33 g, 7.4 mmol) affording 1.5 g (95%) of a beige solid: mp 127–130° C.

INTERMEDIATE 38a

6-Methoxy, 8-Amino-quinoline

To a hot suspension of 6-methoxy, 8-nitro-quinoline in 100 mL of a mixture of ethanol: acetic acid: water (2:2:1) 3.0 g of iron powder were added in portions. The reaction was refluxed for about 2½ hours, the mixture was cooled, filtered over celite and basified with sodium bicarbonate. The product was extracted with ether, dried and the solvent was removed under vacuum to give 3.2 g of the title compound. MS (ES) m/z (relative intensity): 175 (M+H+, 100).

INTERMEDIATE 38b

8-Amino, 6-Chloro-quinoline

To a hot suspension of (0.800 g) 6-chloro, 8-nitro-quinoline in 25 mL of a mixture of ethanol: acetic acid : water (2:2:1) 0.5g of iron powder was added in portions. The reaction was refluxed for about 1½ hours, the mixture was cooled, filtered over celite and basified with sodium carbonate. The product was extracted with ether, dried and the solvent was removed under vacuum to give 0.5 g of the title compound. mp 70–73° C. MS (ES) m/z (relative intensity): 179 (M+H+).

Elemental analysis for $C_9H_7Cl\ N_2$; Calculated: C: 60.52; H: 3.95; N: 15.68; Found: C: 60.82; H: 3.77; N: 15.96.

INTERMEDIATE 39a

6-Methoxy, 8-piperazino-quinoline

6-Methoxy, 8-amino-quinoline (8.2 g) and bis(chloroethyl)amine hydrochloride (9.0 g) were taken in 70 mL chlorobenzene and heated at about 135° C. with vigorous stirring for 3 days. The reaction never went to completion. The mixture was cooled. Water was added and extracted with ether. The aqueous phase was basified with sodium carbonate and extracted with ethyl acetate, dried and the solvent removed. The crude product was filtered through 300 mL of silica gel using 10% $MeOH/CH_2Cl_2$, 20% $MeOH/CH_2Cl_2$, then 1% NH40H/80% MeOH/19% $CH_2Cl_2$, to give 1.5 g of the desired product. MS (ES) m/z (relative intensity): 244 (M+H+, 100).

INTERMEDIATE 39b

6-Chloro-, 8-piperazino-Quinoline 8-amino, 6-chloro-quinoline (0.980 g ) and bis(chloroethyl)amine hydrochloride (0.980 g) were taken in 13 mL chlorobenzene and heated at about 135° C. with vigorous stirring for 5 days. The reaction was cooled taken in water and extracted with ether. The aquous phase is basified with sodium carbonate and reextracted with ether, dried and the sovent was removed to give 0.400 g of the title compound. MS (ES) m/z (relative intensity): 248 (M+H+).

INTERMEDIATE 39c

5-Chloro-, 8-piperazino-quinoline

To a solution of 5-chloro,8-(trifluoromethylsulfonyloxy)-quinoline (1.0 g) in 15 mL chlorobenzene excess piperazine (1.0 g) was added. The mixture was heated at 120° C. for 2½ days. The reaction was cooled, poured on water and the product was extracted with ether, dried over magnesium sulfate to give 0.480 g of product. MS (ES) m/z (relative intensity): 248 (M+H+, 100).

INTERMEDIATE 39d

5-Fluoro, 8-piperazino-quinoline

To a solution of 5-Fluoro,8-(trifluoromethylsulfonyloxy)-quinoline (1 g) in 5 mL chlorobenzene excess piperazine (2.0 g) were added. The mixture was heated at 120° C. for 2½ days. The reaction was cooled, poured on water and the product was extracted with ethyl acetate, the organic phase was washed with dilute NaOH, then with water, dried and the solvent was removed. The product was chromatographed on silica gel using 15% methanol/methylene chloride then 79:20:1 methanol methylene chloride : $NH_4OH$ to give 0.240 g of product. MS (ES) m/z (relative intensity): 232 (M+H+, 100).

INTERMEDIATE 39e

8-piperazino-quinaldine

To a solution of 8-(trifluoromethylsulfonyloxy)-quinaldine (7 g) in 25 mL chlorobenzene, $K_2CO_3$ (3.3 g) and excess piperazine (10.0 g) were added. The mixture was heated at 130° C. for 3 days. The reaction was cooled, poured on water and the product was extracted with ethyl acetate, dried over magnesium sulfate. The product was chromatographed on silica gel using 20% methanol/methylene chloride then 79:20:1 methanol:methylene chloride: $NH_4OH$ to give 3.2 g of product. MS (ES) m/z (relative intensity): 228 (M+H+, 100).

INTERMEDIATE 39f

6-MeO, 4-piperazino-quinoline

To a solution of 6-MeO, 4-(trifluoromethylsulfonyloxy)-quinoline (2 g) in 10 mL acetonitrile, excess piperazine (2 g) was added. The mixture was heated at about 70° C. for 1½ hours. Water is added and the product is extracted with ethyl acetate, dried and the solvent was removed to give (2.5 g) of product. MS (ES) m/z (relative intensity): 308 (M+H+).

INTERMEDIATE 40a

6-Chloro, 8-Nitro-Quinoline

A solution of 1.0 g of 6-Chloro-quinoline in 5 ml fuming nitric acid, was heated to almost reflux for 2 days. The reaction was cooled, poured onto ice water and neutralized with concentrated ammonium hydroxide to about pH 5. The formed precipitate was filtered and dried to give 0.600 g of desired product. mp 149–155° C. MS (ES) m/z (relative intensity): 209 (M+H+).

INTERMEDIATE 40b

5-Cl-8-(trifluoromethylsulfonyloxy)-quinoline

To a suspension of 5-Chloro,8-hydroxy-quinoline (8.95 g) in 100 mL $CH_2Cl_2$, TEA is added (20 mL). The suspension dissolved, then cooled to −15° C. A solution of 21.1 g of triflic anhydride in 50 mL of $CH_2Cl_2$, is added drop by drop with cooling. After complete addition, the reaction was stirred at −15° C. for 1 hour; The reaction was diluted with $CH_2Cl_2$, washed with a solution of $NaHCO_3$, then with water dried and the solvent was removed to give 15.0 gr of product. mp 80–83° C. MS (ES) m/z (relative intensity): 312 (M+H+, 100). Elemental analysis for $C_{10}\ H_5ClF_3NO_3S$ Calculated: C: 38.54; H: 1.62; N: 4.49; Found: C: 38.3; H: 1.73; N: 4.5.

INTERMEDIATE 40c

5-Fluoro-8-(trifluoromethylsulfonyloxy)-quinoline

To a cold solution (−15° C.) of 5-Fluoro,8-hydroxy-quinoline (2.5 g) in 20 mL $CH_2Cl_2$, TEA is added (6.3 mL). To the cold mixture a solution of 6.5 g of triflic anhydride in 10 mL of $CH_2Cl_2$, is added drop by drop with cooling. After complete addition, the reaction was stirred at 0° C. for 1 hour; The reaction was quenched with water, and the product was extracted with ether, dried and the solvent was removed to give 3.4 g of product. MS (ES) m/z (relative intensity): 296 (M+H+, 100).

INTERMEDIATE 40d 8-(trifluoromethylsulfonyloxy)-quinaldine

To a cold solution (−15° C.) of 8-hydroxy-quinaldine (11.5 g) in 50 mL $CH_2Cl_2$, TEA is added (29 mL). To the cold mixture a solution of 29.6 g of triflic anhydride in 50 mL of $CH_2Cl_2$, were added drop by drop with cooling. After complete addition, the reaction was stirred at −15° C. for 1 hour; The reaction was quenched with water, and the product was extracted with ether, dried and the solvent was removed to give 20 g of product. MS (ES) m/z (relative intensity): 292 (M+H+).

INTERMEDIATE 41

6-MeO, 4-(trifluoromethylsulfonyloxy)-quinoline

To a cold solution (−15° C.) of 6-MeO,4-hydroxy-quinoline (5 g) in 30 mL $CH_2Cl_2$, TEA is added (12 mL). To the cold mixture a solution of 12 g of triflic anhydride in 15 mL of $CH_2Cl_2$, were added drop by drop with cooling. After complete addition, the reaction was stirred at −15° C. for 1 hour; The reaction was quenched with water, and the product was extracted with ether, dried and the solvent was removed to give 7 g of product. MS (ES) m/z (relative intensity): 308 (M+H+).

INTERMEDIATE 42a 1-benzyl-4-(6-methoxy-2-methylquinolin-8-yl) piperazine

A mixture of 8-amino-6-methoxy-2-methylquinoline (1.75 g, 9.30 mmol), N-benzyl-bis-dichloroethane (8.9 g, 38.3 mmol), and triethylamine (6.5 mL, 46.6 mmol) in 1-butanol (25 mL) was heated at 100° C. for 20 hours. After cooling to room temperature, the reaction was diluted with ethyl acetate (50 mL), and poured into saturated aqueous $NaHCO_3$. The aqueous layer was extracted with ethyl acetate (3×50 mL). The combined organic layers were washed with saturated aqueous $NaHCO_3$ (50 mL) and brine (50 mL), then were dried over anhydrous sodium sulfate, filtered and concentrated in vacuo. Excess 1-butanol was azeotroped with hexane (2×500 mL). Flash chromatography on 5.5×18 cm $SiO_2$ (25% EtOAc/hexane) afforded 1.15 g (36%) of a yellow oil, which crystallized on standing. Recrystallization from hexane provided 0.898 g (28%) of analytically pure product as yellow crystals: mp 83–85° C.

Elemental analysis for $C_{22}H_{25}N_3O$; Calc'd: C, 76.05; H, 7.25; N, 12.09; Found: C, 75.88; H, 7.37; N, 12.05.

INTERMEDIATE 42b 1-benzyl-4-(6-methoxy-3-methylquinolin-8-yl) piperazine

The title compound was prepared by the same method used for 1-benzyl-4-(6-methoxy-2-methylquinolin-8-yl) piperazine, except substituting 8-amino-6-methoxy-3-methylquinoline (2.82 g, 15.0 mmol) for the 8-amino-6-methoxy-2-methyl-quinoline. Flash chromatography on 6×20 cm $SiO_2$ (25–30% EtOAc/hexane), with rechromatography of the mixed fractions, provided 1.13 g (22%) of the title compound as a yellow gum. Crystallization from hexane afforded 0.88 g of analytically pure compound as yellow crystals: mp 112–113° C.

Elemental analysis for $C_{22}H_{25}N_3O$; Calc'd: C, 76.05; H, 7.25; N, 12.09; Found: C, 75.83; H, 7.26; N, 12.07.

INTERMEDIATE 42c 1-benzyl-4-(6-methoxy-4-methylquinolin-8-yl) piperazine

A mixture of 8-amino-6-methoxy-4-methylquinoline (3.0 g, 15.9 mmol), N-enzyl-bis-dichloroethane (11.1 g, 48.0 mmol), triethyl amine (4.8 g, 48 mmol) and 1-butanol were heated to 100° C. for 24 hours. The reaction mixture was poured into 2.5 N aqueous NaOH and extracted with ethyl acetate (3×200 mL). The combined organic layers were washed with water (100 mL) and brine (100 mL), then were dried over anhydrous sodium sulfate, filtered and concentrated to afford 12.0 g of a dark brown oil. Flash chromatography on silica gel (5% methanol/ethyl acetate) provided 2.3 g (42%) of the title compound as a thick oil, which solidified upon standing: mp 154–155° C.

Elemental analysis for $C_{22}H_{25}N_3O$; Calc'd: C, 76.05; H, 7.25; N, 12.09; Found: C, 75.92; H, 7.36; N, 11.96.

INTERMEDIATE 43a 4-(6-methoxy-2-methylquinolin-8-yl)piperazine

A mixture of 1-benzyl-4-(6-methoxy-2-methylquinolin-8-yl)piperazine (0.527 g, 1.52 mmol), 10% Pd/C (0.20 g), and ammonium formate (0.96 g, 15.2 mmol) in methanol (10 mL) were heated at reflux under $N_2$ for 3 hours. TLC analysis (35% EtOAc/hexane) indicated only a trace of starting material remained. After cooling to room temperature, the reaction was filtered through celite, washing with excess methanol. The filtrate was concentrated, diluted with $CH_2Cl_2$ (50 mL), and washed with saturated aqueous $NaHCO_3$. The aqueous layer was extracted with $CH_2Cl_2$ (2×50 mL). The combined organic layers were dried over anhydrous sodium sulfate, filtered, and concentrated in vacuo to afford 0.37 g (95%) of the title compound as a yellow oil, which was used in the subsequent reaction without purification.

INTERMEDIATE 43b 4-(6-methoxy-3-methylquinolin-8-yl)piperazine

The title compound was prepared by the same method used for the preparation of 4-(6-methoxy-2-methylquinolin-8-yl)piperazine, except 1-benzyl-4-(6-methoxy-3-methylquinolin-8-yl)piperazine (0.32 g, 0.92 mmol) was substituted for the 1-benzyl-4-(6-methoxy-2-methylquinolin-8-yl)piperazine. The title compound was isolated in nearly quantitative yield and used with purification in the subsequent reaction.

INTERMEDIATE 43c 4-(6-methoxy-4-methylquinolin-8-yl)piperazine

A mixture of 1-benzyl-4-(6-methoxy-4-methylquinolin-8-yl)piperazine (2.0 g, 5.76 mmol), methylene chloride (50 mL) and vinyl chloroformate (0.8 mL, 8.64 mmol) were refluxed for 4 hours. The mixture was concentrated, then dissolved in a 1:1 mixture of dioxane/conc. HCl and stirred at ambient temperature for 18 hours. The reaction mixture was made basic with 2.5 N aqueous NaOH and extracted with ethyl acetate (2×200 mL). The combined organic layers were washed with water (100 mL) and brine (100 mL), then were dried over anhydrous sodium sulfate, filtered, and concentrated to give 0.6 g (47%) of the title compound: mp 208–209° C.

Elemental analysis for $C_{15}H_{19}N_3O\cdot HCl\cdot 0.5H_2O$; Calc'd: C, 59.50; H, 6.99; N, 13.88; Found: C, 59.44; H, 7.09; N, 13.57.

INTERMEDIATE 44a 1-benzyl-4-(6-methoxy-5-methylquinolin-8-yl) piperazine

This compound was prepared in a manner similar to that used for 1-benzyl-4-(6-methoxy-4-methylquinolin-8-yl) piperazine to give 3.0 g (56%) of pure title compound: mp 129–133° C.

Elemental analysis for $C_{22}H_{25}N_3O$; Calc'd: C, 76.05; H, 7.25; N, 12.09; Found: C, 75.61; H, 7.35; N, 11.97.

INTERMEDIATE 44b 1-benzyl-4-(6-methoxy-5-chloro-quinolin-8-yl) piperazine

This compound was prepared in a manner similar to that used for 1-benzyl-4-(6-methoxy-4-methylquinolin-8-yl) piperazine to give 1.9 g (35%) of pure title compound: mp 138–140° C.

Elemental analysis for $C_{21}H_{22}ClN_3O$; Calc'd: C, 68.56; H, 6.03; N, 11.42; Found: C, 68.26; H, 5.98; N, 11.45.

INTERMEDIATE 45a 4-(6-methoxy-5-methylquinoline-8-yl)piperazine

A mixture of methanol (15mL), 10% Pd/C (0.12 g), 1-benzyl-4-(6-methoxy-5-methylquinolin-8-yl)piperazine (0.8 g, 2.3 mmol), and ammonium formate (0.88 g, 13.9 mmol) were refluxed for 45 minutes. The reaction mixture was filtered through celite and concentrated. The residue was diluted with 1 N aqueous NaOH (50 mL) and extracted with ethyl acetate (3×75 mL). The combined organic layers were washed with water (50 mL) and brine(50 mL), then were dried over anhydrous $Na_2SO_4$, filtered, and concentrated to give 0.52 g (61%) of the title compound as a thick oil. MS (ES) m/z: 258 (M+H+).

INTERMEDIATE 45b 4-(6-methoxy-5-chloro-quinolin-8-yl)piperazine

This compound was prepared in a manner as similar to that used 4-(6-methoxy-5-methylquinofine-8-yl)piperazine to give 0.48 g (68%) of pure title compound as a thick oil. MS (ES) m/z: 278 (M+H+).

INTERMEDIATE 46

5-Bromo-6-methoxy-quinoline

To a solution of 6-methoxyquinoline (5 g, 31.4 mmol) in acetic acid (50 mL) was slowly added $Br_2$ neat (1.62 mL, 31.4 mmol). The reaction mixture was stirred at ambient temperature for 1 hour and then poured onto ice. Saturated aqueous sodium bisulfite was added, and the resulting slurry was extracted into EtOAc (2×200 mL). The organic fractions were combined, dried over $Na_2SO_4$, concentrated, and purified by column chromatography (5% $MeOH/CH_2Cl_2$) affording 4.39 g of the title compound as the acetate salt. The free base was prepared by washing the salt with 1 N NaOH (50 mL) and $H_2O$ (100 mL) and extracting into $CH_2Cl_2$ (200 mL). The organic fractions were concentrated affording 3.89 g (52%) of the title compound as a pink solid.

Elemental analysis for $C_{10}H_8BrNO$; Calc'd: C, 50.45; H, 3.39; N, 5.88; Found: C, 50.34; H, 3.25; N, 6.09.

INTERMEDIATE 47

4-Bromo-2-nitrophenylamine

To a solution of 2-nitro-phenylamine (13.8 g, 100 mmol) in HOAc (150 mL) was added NBS (18 g, 101 mmol). The reaction mixture was stirred and heated to reflux over 1 hour. The cooled reaction mixture was poured into $H_2O$ (1000 mL) and stirred for 15 minutes. The resulting orange slurry was filtered and washed with $H_2O$ (300 mL) affording a 20.26 g (93%) of the title compound as a bright orange solid.

Elemental analysis for $C_6H_5BrN_2O_2$; Calc'd: C, 33.21; H, 2.32; N, 12.91; Found: C, 33.15; H, 2.31; N, 12.75; Ref: Montash Chem EN 1994, 125 p. 723–730.

INTERMEDIATE 48

6-Bromo-8-nitro-quinoline

A sulfuric acid solution was prepared by adding $H_2SO_4$ (50 mL) to an 250 mL flask containing $H_2O$ (20 mL) cooled in an ice bath. To this solution was added glycerol (12 mL, 16.5 mmol), m-nitrobenzene sulfonic acid sodium salt (11.4 g, 5.06 mmol), and 4-bromo-2-nitrophenylamine (10 g, 4.6 mmol). The reaction mixture was heated at 135° C. for 3 hours. The warm reaction mixture was poured into ice $H_2O$ (200 mL) and extracted into 50% MeOH/EtOAc (2×200 ML), dried over $Na_2SO_4$ and concentrated. The resulting brown solid was triturated with EtOH and filtered affording 3.8 g (33%) of a pink solid: mp 172–174° C.

Elemental analysis for $C_9H_5BrN_2O_2$; Calc'd: C, 42.72; H, 1.99; N, 11.07; Found: C, 42.69; H, 1.85; N, 11.01; Ref: Mantash Chem EN 1994, 125 p. 723–730.

INTERMEDIATE 49

6-Bromo-8-amino-quinoline

To a solution of 6-bromo-8-nitro-quinoline (4 g, 1.58 mmol) in $EtOH/HOAc/H_2O$ (50 mL/50 mL/25 mL) was added iron metal (3.18 g, 5.69 mmol). The resulting solution was heated at reflux for 3 hours. The cooled reaction mixture was neutralized with 2.5 N NaOH, filtered through celite to remove iron solids and washed with EtOAc. The eluent was extracted into EtOAc (3×200 mL), combined, dried over $NASO_4$ and concentrated. The resulting oil was purified by column chromatography (40% EtOAc/hexanes) affording 3.19 g (91%) of a yellow solid: mp 142–145° C.

Elemental analysis for $C_9H_7BrN_2$; Calc'd: C, 48.46; H, 3.16; N, 12.56; Found: C, 48.04; H, 2.93; N, 12.36.

INTERMEDIATE 50

8-(4-benzyl-piperazin-1-yl)-6-bromo-quinoline

The free base of bis(2-chloroethyl)-benzylamine (5.12 g, 19.3 mmol) was prepared by washing the HCl salt with 1 M NaOH (200 mL) and extracting into EtOAc. The resulting organic phases were dried over $NaSO_4$ and concentrated. To this flask was added 6-bromo-8-amino-quinoline (2.15 g, 9.6 mmol), n-BuOH (100 mL), and $Et_3N$ (4 mL, 28.9 mmol). The resulting reaction mixture was stirred at 100° C. overnight. TLC analysis showed starting amine was still present, therefore an additional portion of bis(2-chloroethyl)-benzylamine hydrochloride (5 g) was added. The reaction was heated an additional 72 hours. The cooled reaction mixture was quenched with 1 M NaOH (200 mL) and extracted into EtOAc (3×200 mL). The organic fractions were combined, dried over $Na_2SO_4$, and concentrated. The resulting gold oil was purified three times by column chromatography (40% EtOAc/hexanes) affording 1.2 g (33%) of a viscous orange oil which solidified upon standing: mp 65–68° C., MS (+) APCI m/z 382 $[M+H]^+$.

Elemental analysis for $C_{20}H_{20}BrN_3 \cdot 0.75 H_2O$; Calc'd: C, 60.69; H, 5.48; N, 10.62; Found: C, 60.81; H, 5.02; N, 10.88.

INTERMEDIATE 51

6-Bromo-8-piperazin-1-yl-quinoline

To a solution of 8-(4-benzyl-piperazin-1-yl)-6-bromo-quinoline (1.6 g, 4.2 mmol) in dichloroethane (50 mL) under a $N_2$ atmosphere was added chloroethylchloroformate (1.26 mL, 12.6 mmol) and the reaction mixture was heated at 80° C. for 4 hours, and at ambient temperaure overnight. No reaction was observed by TLC, therefore vinyl chloroformate (0.35 mL, 6.3 mmol) was added and the reaction was heated at 80° C. for another 4 hours. The cooled reaction was poured into $H_2O$ and extracted into $CH_2Cl_2$ (2×100 mL) and EtOAc (100 mL). The organic fractions were combined, dried over $Na_2SO_4$, and left in EtOAc overnight. The organic layer was concentrated and purified by column chromatography 10%$MeOH/CH_2C_2+NH_4OH$) affording 1.03 g (84%) of a brown foam. MS(+)APCI m/z 292 $[M+H]^+$.

INTERMEDIATE 52

6-hydroxy-8-nitro-quinoline

A solution of 6-methoxy-8-nitro-quinoline (9 g, 44.1 mmol) in HBr (100 mL) as heated at 110° C. overnight. Additional HBr (80 mL) was added and the reaction continued to heat for an additional 24 hours. The cooled reaction mixture was basified with 2.5 N NaOH (800 mL) and extracted into EtOAc (2×300 mL). The organic fractions were combined, dried over $Na_2SO_4$ and purified by column chromatography (50% EtOAc/hexane) to afford 2.71 g (32%) of the title compound as a white solid: mp discolors above 100° C., MS(−)ESI m/z 189 $[M-H]^-$.

INTERMEDIATE 53

6-Ethoxy-8-nitro-quinoline

A solution of 6-hydroxy-8-nitro-quinoline (2.5 g, 13.2 mmol), ethylbromide (1.08 mL, 14.5 mmol), and $K_2CO_3$ (4 g, 26.4 mmol) in DMF (50 mL) under a nitrogen atmosphere was heated at 40° C. for 5 hours. The cooled reaction mixture was poured into $H_2O$ (200 mL) and extracted into EtOAc (2×200 mL). The organic fractions were combined, dried over $NaSO_4$ and concentrated. The resulting beige solid was triturated with 40% EtOAc/hexane to give 2.46 g (85%) of the title compound as beige crystals.

Elemental analysis for $C_{11}H_{10}N_2O_3$; Calc'd: C, 60.55; H, 4.62; N, 12.84; Found: C, 60.15; H, 4.50; N, 12.75.

INTERMEDIATE 54

8-(4-benzyl-piperazin-1-yl)-6-methoxy-1,2,3,4-tetrahydroquinoline

A solution of 8-(4-benzyl-piperazin-1-yl)-6-methoxy-quinoline (1 g, 3 mmol) in HOAc (100 mL) was hydrogenated over $PtO_2$ (300 mg) at 40 psi overnight. The reaction mixture was filtered through a pad of celite and was washed with EtOAc (50 mL). The filtrate was concentrated. The resulting gold oil was purified by column chromatography (10%$MeOH/CH_2Cl_2+NH_4OH$) affording 330 mg (45%) of a viscous gold oil. An analytical sample was prepared as the HCl salt from EtOAc. MS EI m/z 247 $M^+$.

Ref: J. Chem Soc Perkins I 1980 p. 1933–1939

INTERMEDIATE 55

[1,6]naphthyridine

A sulfuric acid solution was prepared by adding $H_2SO_4$ (100 mL) to $H_2O$ (57 mL) cooled in an ice bath. To this solution was added glycerol (33 mL, 457 mmol), m-nitrobenzene sulfonic acid sodium salt (48 g, 212 mmol) and 4-amino-pyridine (10 g, 106 mmol). The reaction mixture was heated at 135° C. for 4 hours. The cooled reaction mixture was basicified with 2.5 N NaOH (500 mL) with cooling in an ice bath, and extracted into $CH_2Cl_2$ (3×200 mL). The organic fractions were combined, dried over $Na_2SO_4$ and concentrated. The resulting oil was purified by column chromatography (5% $MeOH/CH_2Cl_2$) affording 5.04 g (36%) as a dark orange oil. An analytical sample was prepared as the HCl salt from EtOAc yielding an orange low melting solid. MS EI m/z 130 $M^+$.

Ref: Chem Pharm Bull. 1971, 19, 9, p. 1751–1755

INTERMEDIATE 56

8-Bromo-[1,6]-naphthyridine

To a stirred solution of [1,6]-naphthyridine (4.73 g, 36.4 mmol) in $CCl_4$ (200 25 mL) was added $Br_2$ (2.25 mL, 43.7 mmol) in $CCl_4$ (35 mL) dropwise via an addition funnel. The resulting solution was heated at reflux for 1 hour. Pyridine (2.94 mL, 36.4 mmol) in $CCl_4$ (30 mL) was added dropwise to the refluxing solution, and the mixture was refluxed overnight. The cooled reaction mixture was filtered, and the solids were digested with 1 M NaOH (200 mL) for 1 hour. The basic solution was extracted into $CH_2Cl_2$ (2×200 mL), and the organic fractions were combined, dried over $Na_2SO_4$ and concentrated. The resulting oil was purified by column chromatography (10% $EtOAc/CH_2Cl_2$) affording 2.03 g (27%) of the title compound as yellow crystals: mp 79–81° C.

Elemental analysis for $C_8H_5BrN_2$; Calc'd: C, 45.97; H, 2.41; N, 13.40; Found: C, 45.72; H, 2.34; N, 13.36; Ref: JOC 1968, 33, 4, p. 1384–1387.

INTERMEDIATE 57

8-piperazin-1-yl-[1,6]-naphthyridine

To an oven-dried 100 mL flask under a nitrogen atmosphere was added 8-bromo-[1,6]-naphthyridine (1.3 g, 6.2 mmol), piperazine (3.21 g, 37.3 mmol), and sodium t-butoxide (900 mg, 9.33 mmol). The solids were suspended in anhydrous o-xylenes (40 mL), and Pd(dba) (285 mg, 5 mol %) and P(t-Bu)$_3$ (0.31 mL, 1.24 mmol) were added. The reaction mixture was heated at 120° C. for 3 hours. The cooled reaction mixture was poured into $H_2O$ (100 mL) and extracted into EtOAc (1×100 mL) and $CH_2Cl_2$ (2×100 mL). The organic fractions were combined, dried over $Na_2SO_4$, concentrated, and the resulting oil was chromatographed (10% MeOH/$CH_2Cl_2$+$NH_4OH$) affording 470 mg (35%) of the title compound as a dark gold oil. An analytical sample was prepared as the HCl salt from EtOAc giving a brown solid: mp decomposes above 200° C. MS(+)APCI m/z 215 $[M+H]^+$.

Ref: Tet. Lett. 1998, 39, p. 617–620

INTERMEDIATE 58

4-(6-Methylamino-quinolin-8-yl)-piperazine-1-carboxylic acid ethyl ester

To an oven-dried 25 mL round bottom flask was added $Cs_2CO_3$ (1.55 g, 4.76 mmol), BINAP (300 mg, 3 mol %), Pd(OAc)$_2$ (100 mg, 3 mol %) and kept under vacuum overnight. To this reaction vessel under a nitrogen atmosphere was added 8-(4-benzyl-piperazin-1-yl)-6-bromo-quinoline (1.3 g, 3.4 mmol), anhydrous toluene (12 mL) and benzylmethylamine (0.53 mL, 4.1 mmol). The reaction mixture was heated at 100° C. overnight. The cooled reaction mixture was diluted with $Et_2O$ (15 mL), filtered to remove solids, washed with EtOAc (10 mL) and concentrated. The resulting oil was purified by column chromatography (40% EtOAc/hexane) affording 830 mg (59%) of benzyl-[8-(4-benzyl-piperazin-1-yl)-quinolin-6-yl]-methyamine as an orange foam.

To a solution of benzyl-[8-(4-benzyl-piperazin-1-yl)-quinolin-6-yl]-methyamine (800 mg, 1.89 mmol) in anhydrous $CH_2Cl_2$ (100 mL) was added vinyl chloroformate (0.48 mL, 5.68 mmol) and heated at reflux overnight. A second aliquot of vinyl chloroformate (0.48 mL) was added and the reaction refluxed an additional 24 hours. The cooled reaction mixture was diluted with $H_2O$ (50 mL) and extracted into $CH_2Cl_2$ (2×50 mL). The combined organic phases were dried over $Na_2SO_4$, filtered and concentrated. The resulting oil was purified by column chromatography (40% EtOAc/hexane) affording 600 mg of a monodebenzylated product. This material was dissolved in EtOH (100 mL) and 10% Pd/C (150 mg) and ammonium formate (244 mg, 4.5 mmol) were added. The reaction was heated at reflux overnight. Additional ammonium formate (250 mg) was added and the reaction refluxed for an additional 72 hours. The cooled reaction mixture was filtered through a pad of celite and washed with EtOAc (200 mL), concentrated and purified by column chromatography (10% MeOH/$CH_2Cl_2$) affording 400 mg of the title compound as a dark gold oil. An analytical sample was prepared as the HCl salt from EtOAc as an orange solid: mp decomposes above 85° C. MS(+)APCI m/z 315 [M+H].

INTERMEDIATE 59

4-methoxy-2,6-dinitro-phenylamine

To a stirred solution of HNO3 (65 mL) was added 4-methoxy-2-nitro-phenylamine (15 g, 89.3 mmol). The reaction mixture was stirred at room temperature overnight. The dark red precipitate was filtered and washed with $H_2O$ (400 mL) affording 10.01 g (53%) of the title compound.

INTERMEDIATE 60

7-Methoxy-quinoxalin-5-ylamine

A solution of 4-methoxy-2,6-dinitro-phenylamine (5 g, 23.5 mmol) in EtOH (200 mL) was hydrogenated over 10% Pd/C (2 g) at 40 psi for 1 hour. After $H_2$ uptake had ceased, the reaction was filtered through a pad of celite and washed with EtOAc (50 mL) and concentrated. Glyoxal (8 ml, 704 mmol) and EtOH (50 mL) were immediately added and the reaction was heated at reflux for 2 hours. The cooled reaction was diluted with $H_2O$ (50 mL) and extracted into $CH_2Cl_2$ (3×100 mL). The organic phases were combined, dried over $Na_2SO_4$, filtered and concentrated. The resulting oil was purified by column chromatography (10% MeOH/$CH_2Cl_2$) affording 430 mg (10%) as a red oil. An analytical sample was prepared as the HCl salt from EtOAc affording a red solid.

INTERMEDIATE 61

(1-Oxy-pyridin-3-yl)-acetonitrile

A solution of 3-pyridylacetonitrile (11 g, 93.1 mmol), HOAc (55 mL), and 30% $H_2O_2$ (17 mL) was heated at 95° C. overnight, and at room temperature for 72 hours. $H_2O$ (50 mL) was added to the reaction mixture and the resulting solution was concentrated. This was repeated with additional $H_2O$ (100 mL). Toluene (2×100 mL) was used to remove residual $H_2O$, and the resulting white solid was dried under vacuum overnight affording a waxy white solid: mp 120–125° C.; MS(+)APCI m/z 135 $[M+H]^+$.

Ref: JACS 1959, 81 p. 740–743 25

INTERMEDIATE 62

3-Cyanomethyl-pyridine-2-carbonitrile

To a suspension of (1-oxy-pyridin-3-yl)-acetonitrile (10 g, 75 mmol) in anhydrous $CH_2Cl_2$ under a nitrogen atmosphere was added trimethylsilylcyanide (10.95 mL, 82 mmol) and dimethylcarbamoylchloride (7.55 mL, 82 mmol). The reaction mixture was stirred at room temperature for 72 hours and then concentrated. EtOAc (100 mL) was added to the residue and the organic phase was washed with 1 M NaOH (150 mL), dried over $Na_2SO_4$, filtered and concentrated. The resulting solid was purified by column chromatography (50% EtOAc/hexanes) affording 7.08 g (66%) of a yellow solid: mp 48–51° C.; MS(+)APCI m/z 144 $[M+H]^+$.

Ref: WO 9818796

INTERMEDIATE 63

6-Methoxy-[1,7]naphthyridin-8-ylamine

To an oven-dried 250 mL flask under a nitrogen atmosphere was added anhydrous MeOH (200 mL). Na metal (1.07 g, 44 mmol) was weighed to a small beaker containing hexane and then transferred to the reaction vessel. After dissolution of the sodium, 3-cyanomethyl-pyridine-2-carbonitrile (5.3 g, 37 mmol) dissolved in anhydrous MeOH (10 mL) was added to the reaction. The resulting solution was heated at 80° C. for 3 hours, then stirred at room temperature overnight. The reaction mixture was concentrated to remove MeOH and extracted into $CH_2Cl_2$ (2×200 mL). The organic phases were combined, dried over $Na_2SO_4$, filtered, concentrated and unsuccessfully chromatographed (2% MeOH/$CH_2Cl_2$). The mixed fractions were combined and recrystalized from EtOAc/hexane affording 1.16 g (18%) of the title compound as a yellow solid. The mother liquor was rechromatographed (50% EtOAc/hexanes) to afford an additional 560 mg (9%) of product: mp decomposes above 110° C.; MS(+)APCI m/z 176 $[M+H]^+$.

Ref: Tet. Lett. 1975 p. 173–174

INTERMEDIATE 64

6-Methoxy-8-piperazin-1-yl-[1,7]naphthyridine

A solution of 6-methoxy-[1,7]naphthyridin-8-ylamine (2.25 g, 12.8 mmol), bis(2-chloroethyl)-benzlyamine (10.25 g, 38.6 mmol) and $Et_3N$ (5.34 mL, 38.6 mmol) in BuOH (100 mL) was heated at 100° C. for 72 hours. The cooled reaction mixture was poured into $H_2O$ (100 mL) and 2.5 N NaOH (100 mL), and extracted into EtOAc (2×200 mL). The organic phases were combined, dried over $NASO_4$, filtered and concentrated. The resulting oil was purified twice by column chromatography (10% $MeOH/CH_2Cl_2$) affording a dark gold oil with BuOH impurity. This oil was dissolved in EtOH (50 mL) and 10% Pd/C (390 mg) and ammonium formate (730 mg) was added. The reaction mixture was heated at 80° C. for 2.5 hours. The cooled reaction mixture was filtered through a pad of celite and washed with EtOAc (50 mL). The organic phase was concentrated and purified by column chromatography (10% $MeOH/CH_2Cl_2+NH_4OH$) affording 270 mg of the title compound as a dark orange oil. An analytical sample was prepared as the HCl salt from EtOAc.

INTERMEDIATE 65

4-Piperazin-1-yl-1,3-dihydro-benzoimidazol-2-one

To a solution of 4-(4-benzylpiperazin-1-yl)-1,3-dihydro-benzoimidazol-2-one (1 g, 3.2 mmol) in anhydrous $CH_2Cl_2$ (50 mL) was added vinyl chloroformate (0.41 mL, 4.87 mmol) under a nitrogen atmosphere. The reaction mixture was heated at reflux for 2 hours, and then a second aliquot of vinyl chloroformate (0.41 mL) was added. The reaction was refluxed an additional 3 hours. The cooled reaction mixture was concentrated, and dioxan (25 mL) and conc. HCl (25 mL) were added to the residue. The resulting solution was stirred at room temperature for 72 hours. The reaction was basicified with 2.5 N NaOH (300 mL) and extracted in MeOH/EtOAc (2×200 mL). The organic fractions were combined, dried over $Na_2SO_4$ and concentrated and the resulting oil purified by column chromatography affording 393 mg (46%) as the oxalate salt. MS(+)ESI m/z 219 $[M+H]^+$.

INTERMEDIATE 66

6-Methoxy-IH-indol-4-ylamine

To a solution of 5-methoxy-2-methyl-1,3-dinitrobenzene[1] (3.28 g, 15 mmol) in 15 mL dry N,N-dimethylformamide was added N,N-dimethyformamide dimethyl acetal (6.16 mL, 45 mmol) and pyrrolidine (1.3 mL, 15 mmol). The reaction mixture was heated at 120° C. until TLC analysis showed complete consumption of the 5-methoxy-2-methyl-1,3-dinitrobenzene. N,N-Dimethylformamide was removed under the vacuum, affording a dark red material, which was dissolved in dry benzene and hydrogenated at 50 psi with 10% Pd/C (0.1 g) for 4 hours. The catalyst was filtered off and the solvent removed under vacuum. Chromatography (25% ethyl acetate/hexane) afforded 1.0 g (40%) of the desired product as a yellow solid: mp 83–861° C.; MS EI m/e 162.

INTERMEDIATE 67

4-(4-Benzyl-piperazin-1-yl)-6-methoxy-1H-indole

A solution of 6-methoxy-1H-indol-4-ylamine (0.76 g, 4.7 mmol) and bis(2-chloroethyl)-benzlyamine (2.72 g, 11.7 mmol) in 1-butanol (20 mL) was stirred at 100° C. for 18 hours then poured into aqueous sodium carbonate solution. The mixture was extracted with ethyl acetate (3×60 mL). The organic layer was dried over anhydrous sodium sulfate and filtered. The solvent was removed under vacuum. Chromatography (30% ethyl acetate/hexane) afforded 0.60 (40%) of product as a gray oil. MS(+)APCI $(M+H)^+$ m/e 322.

INTERMEDIATE 68

6-Methoxy-4-piperazin-1-yl-1H-indole

A mixture of 4-(4-benzyl-piperazin-1-yl)-6-methoxy-1H-indole (0.37 g, 1.1 mmol), 10% Pd/C (0.05 g) and ammonium formate (0.15 g, 2.2 mmol) in ethanol (20 mL) was allowed to reflux for 2 hours. The catalyst was filtered off and the solvent removed under vacuum. Chromatography (10% methanol/methylene chloride plus ammonium hydroxide) afforded 0.2 g (75%) of product as a yellow foam. MS (EI) m/e 231.

EXAMPLE 1a

3-[cis-4-[4-(1H-Indol-4-yl)-1-piperazinyl] cyclohexyl]-1H-indole

A solution of 4-(1H-indol-3-yl)-cyclohexanone (0.53 g, 2.5 mmol), 1-(indol-4-yl)piperazine (0.5 g, 2.5 mmol), sodium triacetoxyborohydride (0.78 g, 3.5 mmol) and acetic acid (0.14 ml, 2.5 mmol) in 1,2-dichloroethane (11 ml) was allowed to stir at room temperature overnight. The reaction was quenched with 1N sodium hydroxide (10 ml), extracted with methylene chloride (3×60 ml), and washed with brine (3×60 ml). The organic layer was dried over anhydrous sodium sulfate and filtered. Chromatography (10% methanol-ethyl acetate) afforded 0.52 g (53%) of product as a white solid: mp 85–87° C.

The HCl salt was prepared in ethyl acetate: mp 198–200° C. Elemental analysis for $C_{26}H_{30}N_4$.HCl; Calc'd: C, 68.25; H, 7.38; N, 12.25; Found: C, 68.12; H, 7.16; N, 11.93.

EXAMPLE 1b

3-[trans-4-[4-(1H-indol-4-yl)-1-piperazinyl] cyclohexyl]-1H-indole

The trans compound was isolated at the same time as the cis isomer in 21% yield (0.21 g) as a white solid: mp 105–107° C.

The HCl salt was prepared in ethyl acetate: mp 305° C. (decomposed). Elemental analysis for $C_{26}H_{30}N_4$.HCl; Calc'd: C, 68.25; H, 7.38; N, 12.25; Found: C, 68.12; H, 7.16; N, 11.93.

EXAMPLE 2a

4-Fluoro-3-[cis-4-[4-(1H-indol-4-yl)-1-piperazinyl] cyclohexyl]-1H-indole

A solution of 4-(4-fluoro-1H-indol-3-yl)-cyclohexanone (0.88 g, 3.8 mmol), 1-(indol-4-yl)piperazine (0.7 g, 3.5 mmol), sodium triacetoxyborohydride (1.1 g, 5.2 mmol) and acetic acid (0.4 ml, 7 mmol) in 1,2-dichloroethane (20 ml) was allowed to stir at room temperature overnight. The reaction was quenched with 1N sodium hydroxide (10 ml), extracted with methylene chloride (3×60 ml), and washed with brine (3×60 ml). The organic layer was dried over anhydrous sodium sulfate and filtered. Chromatography (5–7% methanol-ethyl acetate) afforded 1.14 g (79%) of product as a white foam.

The HCl salt was prepared in ethanol: mp 283–285° C. Elemental analysis for $C_{26}H_{29}FN_4 \cdot HCl \cdot 0.25H_2O$; Calc'd: C, 68.26; H, 6.72; N, 12.25; Found: C, 68.16; H, 6.74; N, 12.04.

EXAMPLE 2b

4-Fluoro-3-[trans-4-[4-(1H-indol-4-yl)-1-piperazinyl]cyclohexyl]-1H-indole

The trans compound was isolated at the same time as the cis isomer in 17% yield (0.24 g) as a white solid: mp 206–208° C.

The HCl salt was prepared in ethanol: mp 297–299° C. Elemental analysis for $C_{26}H_{29}FN_4 \cdot HCl \cdot H_2O$; Calc'd: C, 66.30; H, 6.85; N, 11.90; Found: C, 66.17; H, 6.51; N, 11.70.

EXAMPLE 3a

5-Fluoro-3-[cis-4-[4-(1H-indol-4-yl)-1-piperazinyl] cyclohexyl]-1H-indole

This compound was prepared in the manner described above for Example 2 by replacing 4-(4-fluoro-1H-indol-3-yl)-cyclohexanone with 4-(5-fluoro-1H-indol-3-yl)-cyclohexanone (0.56 g, 2.5 mmol) to afford 0.54 g (52%) of product as a white solid: mp 108–110° C.

The HCl salt was prepared in ethyl acetate: mp 215–217° C. Elemental analysis for $C_{26}H_{29}FN_4 \cdot HCl \cdot 0.36C_4H_8O_2$; Calc'd: C, 67.37; H, 6.88; N, 11.45; Found: C, 67.18; H, 6.72; N, 11.18.

EXAMPLE 3b

5-Fluoro-3-[trans-4-[4-(1H-indol-4-yl)-1-piperazinyl]cyclohexyl]-1H-indole

The trans compound was isolated at the same time as the cis isomer in 30% yield (0.31 g) as a white solid: mp 112–114° C.

The HCl salt was prepared in ethanol: mp 280° C. (decomposed). Elemental analysis for $C_{26}H_{29}FN_4 \cdot HCl$; Calc'd: C, 66.81; H, 6.81; N, 11.99; Found: C, 66.44; H, 6.66; N, 11.74.

EXAMPLE 4a

6-Fluoro-3-[cis-4-[4-(1H-indol-4-yl)-1-piperazinyl] cyclohexyl]-1H-indole

This compound prepared in the manner described above for Example 2 by replacing was 4-(4-fluoro-1H-indol-3-yl)-cyclohexanone with 4-(6-fluoro-1H-indol-3-yl)-cyclohexanone (1.15 g, 5.0 mmol) to afford 1.06 g (51%) of product as a white foam.

The HCl salt was prepared in ethanol: mp 250–252° C. (decomposed). Elemental analysis for $C_{26}H_{29}FN_4 \cdot HCl$; Calc'd: C, 67.37; H, 6.88; N, 11.45; Found: C, 67.18; H, 6.72; N, 11.18.

EXAMPLE 4b

6-Fluoro-3-[trans-4-[4-(1H-indol-4-yl)-1-piperazinyl]cyclohexyl]-1H-indole

The trans compound was isolated at the same time as the cis isomer in 27% yield (0.55 g) as a white foam.

The HCJ salt was prepared in ethanol: mp 319–320° C. (decomposed). Elemental analysis for $C_{26}H_{29}FN_4 \cdot HCl$; Calc'd: C, 66.81; H, 6.81; N, 11.99; Found: C, 66.44; H, 6.66; N, 11.74.

EXAMPLE 5a

5-Bromo-3-[cis-4-[4-(1H-indol-4-yl)-1-piperazinyl] cyclohexyl]-1H-indole

This compound was prepared in the manner described above for Example 2 by replacing 4-(4-fluoro-1H-indol-3-yl)-cyclohexanone with 4-(5-bromo-1H-indol-3-yl)-cyclohexanone (0.75 g, 2.5 mmol) to afford 0.81 g (68%) of product.

The HCl salt was prepared in ethyl acetate: mp 276° C. Elemental analysis for $C_{26}H_{29}BrN_4 \cdot HCl$; Calc'd: C, 60.23; H, 5.93; N, 10.81; Found: C, 59.95; H, 5.83; N, 10.64.

EXAMPLE 5b

5-Bromo-3-[trans-4-[4-(1H-indol-4-yi)-1-piperazinyl]cyclohexyl]-1H-indole

The trans compound was isolated at the same time as the cis isomer in 24% yield (0.29 g).

The HCl salt was prepared in ethyl acetate: mp >300° C. Elemental analysis for $C_{26}H_{29}BrN_4 \cdot HCl$; Calc'd: C, 60.75; H, 5.88; N, 10.90; Found: C, 60.38; H, 5.89; N, 10.61.

EXAMPLE 6a

5-Chloro-3-[cis-4-[4-(1H-indol-4-yl)-1-piperazinyl] cyclohexyl] -1 H-indole

A solution of 4-(5-chloro-1H-indol-3-yl)-cyclohexanone (0.78 g, 3.1 mmol), 1-(indol-4-yl)piperazine (0.6 g, 3 mmol), sodium triacetoxyborohydride (0.95 g, 4.5 mmol) and acetic acid (0.34 ml, 6 mmol) in 1,2-dichloroethane (20 ml) was allowed to stir at room temperature overnight. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (5% methanol-ethyl acetate) afforded 0.84 g (65%) of product as a white foam.

The HCl salt was prepared in ethanol: mp 283–285° C. Elemental analysis for $C_{26}H_{29}ClN_4 \cdot HCl \cdot 0.25H_2O$; Calc'd: C, 65.46; H, 6.69; N, 11.45; Found: C, 65.14; H, 6.73; N, 11.33.

EXAMPLE 6b

5-Chloro-3-[trans-4-[4-(1H-indol-4-yi)-1-piperazinyl]cyclohexyl]-1H-indole

The trans compound was isolated at the same time as the cis isomer in 24% yield (0.32 g) as a white foam.

The HCl salt was prepared in ethanol: mp 314–315.5° C. Elemental analysis for $C_{26}H_{29}ClN_4 \cdot HCl \cdot 0.25H_2O$; Calc'd: C, 65.65; H, 6.60; N, 11.62; Found: C, 65.50; H, 6.50; N, 11.30.

EXAMPLE 7a

3-{4-[(1,4-cis)-4-(1H-indol-4-yl)-piperazinyl-1-yl] cyclohexyl}-1H-indole-5-carbonitrile This compound was prepared in the manner described above for Example 2 by replacing 4-(4-fluoro-1H-indol-3-yl)-cyclohexanone with 4-(5-cyano-1H-indol-3-yl)-cyclohexanone (0.71 g, 3.0 mmol) to afford 0.38 g (30%) of product.

The HCl salt was prepared in ethyl acetate: mp 216–218° C. Elemental analysis for $C_{27}H_{29}N_5 \cdot HCl \cdot 0.33C_4H_8O_2$;

Calc'd: C, 66.25; H, 6.94; N, 13.64; Found: C, 66.05; H, 6.54; N, 13.28.

EXAMPLE 7b

3-{4-[(1,4-trans)-4-(1H-indol-4-yl)-piperazinyl-1-yl] cyclohexyl}-1H-indole-5-carbonitrile The trans compound was isolated at the same time as the cis isomer in 25% yield (0.32 g).

The HCl salt was prepared in ethyl acetate: mp>310° C. Elemental analysis for $C_{27}H_{29}N_5$.HCl; Calc'd: C, 68.48; H, 6.71; N, 14.79; Found: C, 68.43; H, 6.54; N, 14.63.

EXAMPLE 8a

5-Methoxy-3-[cis-4-[4-(1H-indol-4-yl)-1-piperazinyl]cyclohexyl]-1H-indole

A solution of 4-(5-methoxy-1H-indol-3-yl)-cyclohexanone (1.2 g, 5 mmol), 1-(indol-4-yl)piperazine (1 g, 5 mmol), sodium triacetoxyborohydride (1.47 g, 6.2 mmol) and acetic acid (0.28 ml, 4 mmol) in 1,2-dichloroethane (20 ml) was allowed to stir at room temperature overnight. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (2.5% methanol-ethyl acetate) afforded 1.18 g (55%) of product as a white solid: mp 105–108° C.

The HCl salt was prepared in ethyl acetate: mp 283–285° C. Elemental analysis for $C_{27}H_{32}N_4O.HCl.1.5H_2O$; Calc'd: C, 68.55; H, 7.03; N, 11.85; Found: C, 68.86; H, 7.29; N, 11.76.

EXAMPLE 8b

5-Methoxy-3-[trans-4-[4-(1H-indol-4-yl)-1-piperazinyl]cyclohexyl]-1H-indole

The trans compound was isolated at the same time as the cis isomer in 20% yield (0.43 g) as a white foam.

The HCl salt was prepared in ethyl acetate: mp 194–196° C. Elemental analysis for $C_{27}H_{32}N_4O.HCl.0.5H_2O$ Calc'd: C, 66.65; H, 7.15; N, 11.52; Found: C, 66.65; H, 7.06; N, 11.44.

EXAMPLE 9a

3-[cis-4-[4-(1H-Indol-4-yl)-1-piperazinyl] cyclohexyl]-2-methyl-1H-indole

A solution of 4-(1H-indol-3-yl)-cyclohexanone (1.44 g, 6.33 mmol), 1-(indol-4-yl)piperazine (1.27 g, 6.33 mmol), sodium triacetoxyborohydride (1.88 g, 8.86 mmol) and acetic acid (0.76 mg, 12.6 mmol) in 1,2-dichloroethane (100 ml) was allowed to stir at room temperature overnight. The reaction was quenched with 1N sodium hydroxide (80 ml), extracted with methylene chloride (3×300 ml), and washed with brine (150 ml). The organic layer was dried over anhydrous sodium sulfate and filtered. The solvent was removed under vacuum to afford an off-white solid. Trituration of the solid with warm methylene chloride (80 ml) followed by filtration afforded 0.88 g of white solid. The mother liquor was concentrated and chromatographed (2% methanol-methylene chloride) to afford another 0.18 g (total yield 40.7%) of product as a white solid: mp 279–280° C.

The HCl salt was prepared in ethanol: mp 200–203° C. Elemental analysis for $C_{27}1H_{32}N_4.2HCl$; Calc'd: C, 64.99; H, 7.17; N, 11.23; Found: C, 65.05; H, 7.07; N, 11.23.

EXAMPLE 9b

3-[trans-4-[4-(1H-Indol-4-yl)-1-piperazinyl] cyclohexyl]-2-methyl-1H-indole

The trans compound was isolated at the same time as the cis isomer in 25.7% yield (0.67 g) as a white foam.

The HCl salt was prepared in ethanol: mp>310° C. Elemental analysis for $C_{27}H_{32}N_4.2HCl$; Calc'd: C, 66.80; H, 7.06; N, 11.54; Found: C, 66.84; H, 6.87; N, 11.37.

EXAMPLE 10a

3-{(1,4-cis)-4-[4-(1H-Indole-4-yl)-piperazin-1-yl]-cyclohexyl}-1H-pyrrolo[2,3-b]pyridine This compound was prepared in the manner described above for Example 2 by replacing 4-(5-fluoro-1H-indol-3-yl)-cyclohexanone with 4-(1H-3-pyrrolo[2,3-b]pyridyl)-cyclohexanone (1.52 g, 7.1 mmol) in 27% (0.79 g) yield as a white solid.

The HCl salt was prepared in ethanol: mp>250° C. (dec.) Elemental analysis for $C_{25}H_{29}N_5.3HCl$; Calc'd: C, 58.49; H, 6.38; N, 13.64; Found: C, 58.47; H, 6.52; N, 12.91.

EXAMPLE 10b

3-{(1,4-trans)-4-[4-(1H-Indole-4-yl)-piperazin-1-yl]-cyclohexyl}-1H-pyrrolo[2,3-b]pyridine The trans compound was isolated at the same time as the cis isomer in 9% yield (0.26 g) as a white solid: mp>228° C. The HCl salt was prepared in ethanol: mp>250° C. (dec.) Elemental analysis for $C_{25}H_{29}N_5.3HCl$; Calc'd: C, 56.50; H, 6.54; N, 13.18; Found: C, 56.45; H, 6.63; N, 12.98.

EXAMPLE 11

6-Fluoro-1-methyl-3-{cis-4-[4-(1-methyl-1H-indol-4-yl)-1-piperazinyl]cyclohexyl}-1H-indole To a solution of 3-[cis-4-[4-(1H-indol-4-yl)-1-piperazinyl]cyclohexyl]-1H-indole (0.27 g, 0.65 mmol) in anhydrous N,N-dimethylformamide (4 ml) was added 60% sodium hydride (33.7 mg, 0.84 mmol) at room temperature. The mixture was allowed to stir for 30 minutes at room temperature, then iodomethane was added to the above solution. The resulting mixture was stirred for another 0.5 hour and then poured into water (80 ml) and extracted with ethyl acetate (2×80 ml). The organic layer was dried over anhydrous magnesium sulfate and filtered. Chromatography (20% acetone-hexanes) afforded 0.93 g (55%) of product as an oil which was heated in ethanol to afford a white solid: mp 188–190° C.

The HCl salt was prepared in ethanol: mp 253–254° C. Elemental analysis for $C_{28}H_{23}N_4F.HCl.0.5H_2O$; Calc'd: C, 68.62; H, 7.20; N, 11.43; Found: C, 68.98; H, 6.80; N, 11.47.

EXAMPLE 12a

3-{(1,4-cis)-4-[4-(1H-indol-4-yl)-piperazin-1-yl]-cyclohexyl}-1-methyl-1H-indole-5-carbonitrile A solution of 4-(5-cyano-1-methyl-3-indolyl)-cyclohexanone (0.75 g, 3 mmol), 1-(indol-4-yl)piperazine (0.6 g, 3 mmol), sodium triacetoxyborohydride (0.95 g, 4.5 mmol) and acetic acid (0.34 ml, 6 mmol) in 1,2-dichloroethane (20 ml) was allowed to stir at room temperature overnight. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (10% methanol-ethyl acetate) afforded 0.73 g (56%) of product as a white solid: mp 274–275° C.

The HCl salt was prepared in ethyl acetate: mp 285.5–288° C. Elemental analysis for $C_{28}H_{31}N_5 \cdot 2HCl \cdot H_2O$; Calc'd: C, 68.35; H, 6.97; N, 14.23; Found: C, 68.51; H, 6.65; N, 14.06.

EXAMPLE 12b

3-{(1,4-trans)-4-[4-(1H-indol-4-yl)-piperazin-1-yl]-cyclohexyl}-1-methyl-1H-indole-5-carbonitrile The trans compound was isolated at the same time as the cis isomer in 33% yield (0.42 g) as a white solid: mp 239–240° C.

The HCl salt was prepared in ethyl acetate: mp 286–288° C. Elemental analysis for $C_{28}H_{31}N_5 \cdot 2HCl \cdot 0.5H_2O$; Calc'd: C, 64.73; H, 6.60; N, 13.65; Found: C, 64.55; H, 6.42; N, 13.41.

EXAMPLE 13a

1-Ethyl-3-{(1,4-cis)-4-[4-(1H-indol-4-yl)-piperazin-1-yl]cyclohexyl}-1H-indole-5-carbonitrile A solution of 4-(5-cyano-1-ethyl-indol-3-yl)-cyclohexanone (1.5 g, 5.6 mmol), 1-(indol-4-yl)piperazine (1.19 g, 5.9 mmol), sodium triacetoxyborohydride (1.73 g, 8.2 mmol) and acetic acid (0.9 ml, 15 mmol) in 1,2-dichloroethane (30 ml) was allowed to stir at room temperature overnight. The reaction was quenched with 1N sodium hydroxide (10 ml), extracted with methylene chloride (3×80 ml), and washed with brine (3×80 ml). The organic layer was dried over anhydrous sodium sulfate and filtered. Chromatography (2.5% methanol-ethyl acetate) afforded 0.98 g (39%) of product as a white solid: mp 226° C. (dec.).

The HCl salt was prepared in ethyl acetate: mp 245° C. Elemental analysis for $C_{29}H_{33}N_5 \cdot 2HCl \cdot 0.25H_2O$; Calc'd: C, 65.84; H, 6.76; N, 13.24; Found: C, 65.97; H, 6.74; N, 13.40.

EXAMPLE 13b

1-Ethyl-3-{(1,4-trans)-4-[4-(1H-indol-4-yl)-piperazin-1-yl]-cyclohexyl}-1H-indole-5-carbonitrile The trans compound was isolated at the same time as the cis isomer in 19% yield (0.48 g) as a light brown solid: mp decomposed at 110C.

The HCl salt was prepared in ethyl acetate: mp 250° C. (decomposed). Elemental analysis for $C_{29}H_{33}N_5 \cdot 2HCl$; Calc'd: C, 66.40; H, 6.73; N, 13.35; Found: C, 66.32; H, 6.67; N, 13.10.

EXAMPLE 14a

3-{(1,4-cis)-4-[4-(1H-indol-4-yl)-piperazin-1-yl]-cyclohexyl}-1-propyl-1H-indole-5-carbonitrile A solution of 4-(5-cyano-1-n-propyl-indol-3-yl)-cyclohexanone (1.68 g, 6 mmol), 1-(indol-4-yl)piperazine (1.27 g, 6.3 mmol), sodium triacetoxyborohydride (1.84 g, 8.9 mmol) and acetic acid (0.94 ml, 16 mmol) in 1,2-dichloroethane (80 ml) was allowed to stir at room temperature overnight. The reaction was quenched with 1N sodium hydroxide (20 ml), extracted with methylene chloride (3×100 ml) and washed with brine (3×100 ml). The organic layer was dried over anhydrous sodium sulfate and filtered. Chromatography (10% methanol-ethyl acetate) afforded 0.42 g(15%) of product as a white powder.

The HCl salt was prepared in ethanol: mp 200–206° C. Elemental analysis for $C_{30}H_{35}N_5 \cdot 2HCl \cdot 0.75H_2O$; Calc'd: C, 65.27; H, 7.03; N, 12.69; Found: C, 65.18; H, 6.97; N, 12.68.

EXAMPLE 14b

3-{(1,4-trans)-4-[4-(1H-indol-4-yl)-piperazin-1-yl]-cyclohexyl}-1-propyl-1H-indole-5-carbonitrile The trans compound was isolated at the same time as the cis isomer in 14% yield (0.39 g) as a white foam.

The HCl salt was prepared in ethanol: mp decomposed>245° C. Elemental analysis for $C_{30}H_{35}N_5 \cdot 2HCl$; Calc'd: C, 66.90; H, 6.93; N, 13.00; Found: C, 66.68; H, 6.97; N, 12.96.

EXAMPLE 15a

3-{(1,4-cis)-4-[4-(1H-indol-4-yl)-piperazin-1-yl]-cyclohexyl}-1-isopropyl-1H-indole-5-carbonitrile A solution of 4-(5-cyano-1-n-propyl-indol-3-yl)-cyclohexanone (1.68 g, 6 mmol), 1-(indol-4-yl)piperazine (1.27 g, 6.3 mmol), sodium triacetoxyborohydride (1.84 g, 8.9 mmol) and acetic acid (0.94 ml, 16 mmol) in 1,2-dichloroethane (80 ml) was allowed to stir at room temperature overnight. The reaction was quenched with 1N sodium hydroxide (20 ml), extracted with methylene chloride (3×100 ml), and washed with brine (3×100 ml). The organic layer was dried over anhydrous sodium sulfate, and filtered. Chromatography (10% methanol-ethyl acetate) afforded 0.49 g (18%) of product as a white powder.

The HCl salt was prepared in ethanol: mp 285–286° C. Elemental analysis for $C_{30}H_{35}N_5 \cdot HCl_{0.5}H_2O$; Calc'd: C, 70.50; H, 7.30; N, 13.70; Found: C, 70.65; H, 7.16; N, 13.45.

EXAMPLE 15b

3-{(1,4-trans)-4-[4-(1H-indol -4-yl)-piperazin-1-yl]-cyclohexyl}-1-isopropyl-1H-indole-5-carbonitrile The trans compound was isolated at the same time as the cis isomer in 12% yield (0.34 g) as a white foam.

The HCl salt was prepared in ethanol: mp decomposed>245° C. Elemental analysis for $C_{30}H_{35}N_5 \cdot HCl$; Calc'd: C, 66.90; H, 6.93; N, 13.00; Found: C, 66.68; H, 6.97; N, 12.96.

EXAMPLE 16a

1-Benzyl-3-{(1,4-cis)-4-[4-(1H-indol-4-yl)-piperazin-1-yl]-cyclohexyl}-1H-indole-5-carbonitrile A solution of 4-(5-cyano-1-benzyl-indol-3-yl)-cyclohexanone (2.97 g, 9 mmol), 1-(indol-4-yl)piperazine (1.94 g, 9.6 mmol), sodium triacetoxyborohydride (2.7 g, 13 mmol) and acetic acid (1 ml, 24 mmol) in 1,2-dichloroethane (50 ml) was allowed to stir at room temperature overnight. The reaction was quenched with 1N sodium hydroxide (20 ml), extracted with methylene chloride (3×100 ml) and washed with brine (3×100 ml). The organic layer was dried over anhydrous sodium sulfate and filtered. Chromatography (25–50% ethyl acetate-hexanes) afforded 1.71 g (37%) of product as a white powder.

The HCl salt was prepared in ethanol: mp dec.>245° C. Elemental analysis for $C_{34}H_{35}N_5 \cdot HCl \cdot 0.5H_2O$; Calc'd: C, 68.56; H, 6.43; N, 11.76; Found: C, 68.93; H, 6.55; N, 11.52.

EXAMPLE 16b

1-Benzyl-3-{(1,4-trans)-4-[4-(1H-indol-4-yl)-
piperazin-1-yl]-cyclohexyl}-1H-indole-5-
carbonitrile The trans compound was isolated at the same time as the cis isomer in 15% yield (0.68 g) as a white foam.

The HCl salt was prepared in ethanol: mp>240° C. (dec.). Elemental analysis for $C_{34}H_{53}N_5 \cdot 2HCl \cdot 0.25H_2O$; Calc'd: C, 69.08; H, 6.40; N, 11.85; Found: C, 69.09; H, 6.17; N, 11.80.

EXAMPLE 17

1-Methyl-3-{(1,4-cis)-4-[4-(1-methyl-1H-indol-4-
yl)-piperazin-1-yl]-cyclohexyl}-1H-indole-5-
carbonitrile To a suspension of sodium hydride (60%, 95 mg, 2.4 mmol) in anhydrous N,N-dimethylformamide was added a solution 3-{(1,4-cis)-4-[4-(1H-indol-4-yl)-piperazin-1-yl]-cyclohexyl}-1-methyl-1H-indole-5-carbonitrile (0.52 g, 1.2 mmol) in 10 ml N,N-dimethylformide. The mixture was allowed to stir at room temperature for 30 minutes. Then iodomethane (0.17 g, 2.4 mmol) was added to the above reaction mixture. The mixture was allowed to stir at room temperature for another 30 minutes, then quenched with ice-water. The mixture was extracted with methylene chloride (150 ml), and dried over anhydrous sodium sulfate. Chromatography (methanol-methylene chloride-ethyl acetate; 1:1:8) afforded 0.53 g (99%) of product as a pink foam.

The HCl salt was prepared in ethanol: mp 252–255° C. Elemental analysis for $C_{29}H_{33}N_5 \cdot 2HCl$; Calc'd: C, 66.40; H, 6.73; N, 13.35; Found: C, 66.64; H, 6.82; N, 13.21.

EXAMPLE 18

5-Fluoro-3-{(cis)-4-[4-(2-methoxy-phenyl)-
piperazin-1-yl]-cyclohexyl}-1H-indole A solution of 4-(5-fluoro-1-indol-3-yl)-cyclohexanone (0.35 g, 1.5 mmol), 1-(2-methoxy-phenyl)piperazine (0.29 g, 1.5 mmol), sodium triacetoxyborohydride (0.47 g, 2.1 mmol) and acetic acid (0.05 ml, 1.5 mmol) in 1,2-dichloroethane (8 ml) was allowed to stir at room temperature for 12 hours. The reaction was quenched with 1N sodium hydroxide (pH>9) and extracted with methylene chloride (3×50 ml). The organic layer was dried over anhydrous sodium sulfate and filtered. Chromatography (10% methanol-ethyl acetate) afforded 0.34 g (56%) of product as a white solid.

The HCl salt was prepared in ethyl acetate: mp 170–172° C. Elemental analysis for $C_{25}H_{30}FN_3O \cdot HCl$; Calc'd: C, 66.95; H, 7.08; N, 9.37; Found: C, 66.93; H, 7.08; N, 9.29.

EXAMPLE 19a

5-Fluoro-3-{(1,4-cis)-4-[4-(2-methoxy-phenyl)-
piperidin-1-yl]-cyclohexyl}-1H-indole This compound was prepared in the manner described above for Example 18 by replacing 1-(2-methoxy-phenyl)piperazine with 1-(2-methoxy-phenyl)piperidine (1.0 g, 5.2 mmol) to afford 1.34 g of product in 63% yield.

The HCl salt was prepared in ethyl acetate: mp 245–250° C. Elemental analysis for $C_{26}H_{31}FN_2O \cdot HCl \cdot 0.09C_4H_8O_2$; Calc'd: C, 69.09; H, 7.36; N, 6.20; Found: C, 66.19; H, 7.18; N, 6.08.

EXAMPLE 19b

5-Fluoro-3-{(1,4-trans)-4-[4-(2-methoxy-phenyl)-
piperidin-1-yl]-cyclohexyl}-1H-indole The trans compound was isolated at the same time as the cis isomer in 20% yield (0.43 g).

The HCl salt was prepared in ethyl acetate: mp 297–299° C. Elemental analysis for $C_{26}H_{31}FN_2O \cdot HCl \cdot 0.08C_4H_8O_2$; Calc'd: C, 70.49; H, 7.28; N, 6.32; Found: C, 70.17; H, 7.30; N, 6.10.

EXAMPLE 20a

5-Methoxy-3-{(1,4-cis)-4-[4-(2-methoxy-phenyl)-
piperazin-1-yl]-cyclohexyl}-1H-indole This compound was prepared in the manner described above for Example 18 by replacing 4-(5-fluoro-1-indol-3-yl)-cyclohexanone with 4-(5-methoxy-1-indol- 3-yl)-cyclohexanone (1.2 g, 5 mmol) to afford 1.18 g (55%) of the title compound as a white solid: mp 105–108° C.

The HCl salt was prepared in ethyl acetate: mp 198–199° C. Elemental analysis for $C_{26}H33N_3O_2 \cdot HCl$; Calc'd: C, 68.48; H, 7.52; N, 9.21; Found: C, 68.31; H, 7.54; N, 9.08.

EXAMPLE 20b

5-Methoxy-3-{(1,4-trans)-4-[4-(2-methoxy-phenyl)-
piperazin-1-yl]-cyclohexyl]-1H-indole The trans compound was isolated at the same time as the cis isomer in 20% yield (0.43 g) as a white foam.

The HCl salt was prepared in ethyl acetate: mp 195–197° C. Elemental analysis for $C_{26}H_{33}N_3O_2 \cdot HCl$; Calc'd: C, 68.48; H, 7.52; N, 9.21; Found: C, 68.18; H, 7.50; N, 9.11.

EXAMPLE 21

3-{(1,4-cis)-4-[4-(2-methoxy-phenyl)-piperazin-1-
yl]-cyclohexyl}-1H-pyrrolo[2,3-b]pyridine This compound was prepared in the manner described above for Example 18 by replacing 4-(5-fluoro-1H-indol-3-yl)-cyclohexanone with 4-(1H-pyrrolo[2,3-b]-3-pyridyl)-cyclohexanone (1.71 g, 7.9 mmol) in 42% yield (1.34 g) as a white solid: mp 170–172° C.

The HCl salt was prepared in ethanol: mp 259–261° C. Elemental analysis for $C_{24}H_{30}ON_4 \cdot HCl$; Calc'd: C, 65.44; H, 7.44; N, 12.72; Found: C, 65.60; H, 7.36; N, 12.22.

EXAMPLE 22a

5-Fluoro-3-{(cis)-4-[4-(5-fluoro-2-methoxy-phenyl)-
piperazin-1-yl]-cyclohexyl}-1H-indole A solution of 4-(5-fluoro-1-indol-3-yl)-cyclohexanone (1.1 g, 4.8 mmol), 1-(2-methoxy-5-fluoro-phenyl)piperazine (1.0 g, 4.8 mmol), sodium triacetoxyborohydride (1.5 g, 7.1 mmol) and acetic acid (0.27 ml, 4.7 mmol) in 1,2-dichloroethane (20 ml) was allowed to stir at room temperature for 12 hours. The reaction was quenched with 1N sodium hydroxide (pH>9), extracted with methylene chloride (3×50 ml). The organic layer was dried over anhydrous sodium sulfate and filtered. Chromatography (10% methanol-ethyl acetate) afforded 1.16 g (53%) of product as a white solid: mp 152–153° C.

The HCl salt was prepared in ethyl acetate: mp 171–174° C. Elemental analysis for $C_{25}H_{29}F_2N_3O \cdot 2HCl$; Calc'd: C, 59.17; H, 6.36; N, 8.28; Found: C, 59.20; H, 6.33; N, 8.09.

EXAMPLE 22b

5-Fluoro-3-{(trans)-4-[4-(5-fluoro-2-methoxy-phenyl)-piperazin-1-yl]-cyclohexyl}-1H-indole The trans compound was isolated at same time as the cis isomer in 12% yield (0.25 g) as a white solid: mp 64–67° C.

The HCl salt was prepared in ethyl acetate: mp 272–273.5° C. Elemental analysis for $C_{25}H_{29}F_2ON_3.HCl$; Calc'd: C, 63.75; H, 6.64; N, 8.92; Found: C, 63.77, H, 6.41; N, 8.75.

EXAMPLE 23a

3-{(1,4-cis)-4-[4(2,3-Dihydro-benzo[1,4]dioxin-5-yl)-piperazin-1-yl]-cyclohexyl}-4-fluoro-1H-indole A solution of 4-(4-fluoro-1-indol-3-yl)-cyclohexanone (0.71 g, 3.1 mmol), 5-(1-piperazinyl)benzodioxan (0.77 g, 3.5 mmol), sodium triacetoxyborohydride (0.98 g, 4.6 mmol) and acetic acid (0.28 g, 4.6 mmol) in 1,2-dichloroethane (70 ml) was allowed to stir at room temperature for 12 hours. The reaction was quenched with 1N sodium hydroxide (100 ml), extracted with methylene chloride (3×100 ml). The organic layer was dried over anhydrous magnesium sulfate and filtered. Chromatography (1% methanol-ethyl acetate) afforded 0.8 g (53%) of product as a white foam which was dissolved in warm ethanol (15 ml) and crystallized to afford a white solid: mp 194–195.5° C.

The HCl salt was prepared in ethanol: mp 215–220° C. Elemental analysis for $C_{26}H_{30}FN_3O_2.HCl$; Calc'd: C, 61.42; H, 6.34; N, 8.62; Found: C, 61.15; H, 6.29; N, 8.04.

EXAMPLE 23b

3-{(1,4-trans)-4-[4-(2,3-Dihydro-benzo[1,4]dioxin-5-yl)-piperazin-1-yl]-cyclohexyl}-4-fluoro-1H-indole The trans compound was isolated at the same time as the cis isomer in 14% yield (0.21 g) as a white foam which was recrystallization in ethanol to afford a white solid: mp 188–190° C.

Elemental analysis for $C_{26}H_{30}FO_2N_3$; Calc'd: C, 71.70; H, 6.94; N, 9.65; Found: C, 71.33, H, 7.03; N, 9.55.

EXAMPLE 24a

3-{(1,4-cis)-4-[4-(2,3-Dihydro-benzo[1,4]dioxin-5-yl)-piperazin-1-yl]-cyclohexyl}-5-fluoro-1H-indole A solution of 4-(5-fluoro-1-indol-3-yl)-cyclohexanone (1.06 g, 4.6 mmol), 5-(1-piperazinyl)benzodioxan (1.14 g, 5.2 mmol), sodium triacetoxyborohydride (1.46 g, 6.9 mmol) and acetic acid (0.41 g, 6.9 mmol) in 1,2-dichloroethane (80 ml) was allowed to stir at room temperature for 12 hours. The reaction was quenched with saturated sodium bicarbonate (100 ml), extracted with methylene chloride (3×100 ml). The organic layer was dried over anhydrous magnesium sulfate and filtered. Chromatography (1% methanol-ethyl acetate) afforded 1.06 g (53%) of product as an oil which solidified to afford a white solid: mp 104–106° C.

The HCl salt was prepared in ethanol: mp 222–225° C. Elemental analysis for $C_{26}H_{30}FN_3O_2.2HCl.0.2H_2O$; Calc'd: C, 60.88; H, 6.39; N, 8.19; Found: C, 60.85; H, 6.03; N, 8.13.

EXAMPLE 24b

3-{(1,4-trans)-4-[4-(2,3-Dihydro-benzo[1,4]dioxin-5-yl)-piperazin-1-yl]-cyclohexyl}-5-fluoro-1H-indole The trans compound was isolated at the same time as the cis isomer in 27% yield (0.53 g) as a white solid: mp 206–210° C.

The HCl salt was prepared in ethanol: mp 295–297° C. Elemental analysis for $C_{26}H_{30}FO_2N_3.2HCl$; Calc'd: C, 61.42; H, 6.34; N, 8.26; Found: C, 61.22; H, 6.19; N, 8.13.

EXAMPLE 25a

3-{(1,4-cis)-4-[4-(2,3-Dihydro-benzo[1,4]dioxin-5-yl)-piperazin-1-yl]-cyclohexyl}-6-fluoro-1H-indole A solution of 4-(5-fluoro-1-indol-3-yl)-cyclohexanone (0.77 g, 3.0 mmol), 5-(1-piperazinyl)benzodioxan (0.78 g, 3.0 mmol), sodium cyanoborohydride (0.2 g, 3.0 mmol) in methanol (100 ml) was allowed to stir at room temperature for 48 h. The reaction was quenched with potassium hydroxide (0.4 g). The methanol was removed under vacuum, the residue was extracted with ethyl acetate (3×100 ml) and washed with water. The organic layer was dried over anhydrous magnesium sulfate and filtered. Chromatography (1% methanol-ethyl acetate) afforded 0.24 g (18%) of product as a yellow solid.

The HCl salt was prepared in ethanol: mp 228–230° C. Elemental analysis for $C_{26}H_{30}FN_3O_2.2HCl_{0.6}C_2H_6O$; Calc'd: C, 61.37; H, 6.38; N, 8.22; Found: C, 61.19; H, 6.32; N, 8.29.

EXAMPLE 25b

3-{(1,4-trans)-4-[4-(2,3-Dihydro-benzo[1,4]dioxin-5-yl)-piperazin-1-yl]-cyclohexyl}-6-fluoro-1H-indole The trans compound was isolated at the same time as the cis isomer in 8% yield (0.11 g) as an oil.

The HCl salt was prepared in ethanol: mp 309–310° C. Elemental analysis for $C_{26}H_{30}FO_2N_3.2HCl.0.08C_4H_8O_2$; Calc'd: C, 61.42; H, 6.34; N, 8.26; Found: C, 61.22; H, 6.19; N, 8.13.

EXAMPLE 26a

3-{(1,4-cis)-4-[4-(2,3-Dihydro-benzo[1,4]dioxin-5-yl)-piperazin-1-yl]-cyclohexyl}1H-indole-5-carbonitrile A solution of 4-(5-cyano-1-indol-3-yl)-cyclohexanone (0.60 g, 2.5 mmol), 5-(1-piperazinyl)benzodioxane (0.55 g, 2.5 mmol), sodium triacetoxyborohydride (0.78 g, 3.5 mmol) and acetic acid (0.14 g, 2.5 mmol) in 1,2-dichloroethane (11 ml) was allowed to stir at room temperature for 12 hours. The reaction was quenched with 1N sodium (100 ml), extracted with methylene chloride (3×100 ml). The organic layer was dried over anhydrous magnesium sulfate, and filtered. Chromatography (1% methanol-ethyl acetate) afforded 0.46 g (41%) of product.

The HCl salt was prepared in ethyl acetate: mp 300° C. Elemental analysis for $C_{27}H_{30}N_4O_2.HCl.0.07C_4H_8O_2$; Calc'd: C, 65.84; H, 6.65; N, 11.38; Found: C, 65.65; H, 6.47; N, 11.11.

EXAMPLE 26b

3-{(1,4-trans)-4-[4-(2,3-Dihydro-benzo[1,4]dioxin-5-yl)-piperazin-1-yl]-cyclohexyl}-1H-indole-5-carbonitrile The trans compound was isolated at the same time as the cis isomer in 31% yield (0.34 g).

The HCl salt was prepared in ethyl acetate: mp 300° C. (decomposed). Elemental analysis for C$_{27}$H$_{30}$O$_2$N$_4$.HCl.0.08C$_4$H$_8$O$_2$; Calc'd: C, 66.43; H, 6.69; N, 11.34; Found: C, 66.57; H, 7.02; N, 10.85.

EXAMPLE 27a

8-{4-[(1,4-cis)-4-(5-Fluoro-1H-indol-3-yl)-cyclohexyl]-piperazin-1-yl}-quinoline A solution of 4-(5-fluoro-1-indol-3-yl)-cyclohexanone (0.54 g, 2.3 mmol), 8-(piperazin-1-yl)-quinoline (0.5 g, 2.3 mmol), sodium triacetoxyborohydride (0.75 g, 3.5 mmol) and acetic acid (0.27 ml, 4.7 mmol) in 1,2-dichloroethane (20 ml) was allowed to stir at room temperature for overnight. The reaction was quenched with 1N sodium hydroxide (20 ml), extracted with methylene chloride (3×100 ml), and washed with brine (3×100 ml). The organic layer was dried over anhydrous sodium sulfate and filtered. Chromatography (5% methanol-ethyl acetate) afforded 0.46 g (46%) of product as a white solid: mp 122–125° C.

The HCl salt was prepared in ethanol: mp 209–212° C. Elemental analysis for C$_{27}$H$_{29}$FN$_4$.3HCl; Calc'd: C, 66.28; H, 6.00; N, 10.42; Found: C, 60.23; H, 6.29; N, 10.21.

EXAMPLE 27b

8-{4-[(1,4-trans)-4-(5-Fluoro-1H-indol-3-yl)-cyclohexyl]-piperazin-1-yl}-quinoline The trans compound was isolated at the same time as the cis isomer in 25% yield (0.25 g) as a white solid: mp 207.5–209° C.

The HCl salt was prepared in ethanol: mp 286–288° C. Elemental analysis for C$_{27}$H$_{29}$FN$_4$.HCl; Calc'd: C, 64.67; H, 6.23; N, 11.17; Found: C, 64.74; H, 6.27; N, 11.06.

EXAMPLE 28

8-{4-(1,4-cis)-4-[4-(5-Fluoro-1-methyl-1H-indol-3-yl)-cyclohexyl]-piperazin-1-yl}-quinoline To a suspension of sodium hydride (60%, 0.03 g, 0.76 mmol) in anhydrous N,N-dimethylformamide (4 ml) was added $^8$-{$^4$-[(1,4-cis)-4-(5-fluoro-1H-indol-3-yl)-cyclohexyl]-piperazin-1-yl}-quinoline (0.25 g, 0.58 mmol) in 6 ml anhydrous N,N-dimethylformamide at room temperature. The mixture was stirred at room temperature for 30 minutes, then iodomethane (0.044 ml, 0.7 mmol) was added to the above solution. The resulting mixture was stirred at room temperature for 30 minutes, and quenched with water. The mixture was extracted with ethyl acetate and the organic layer was dried over anhydrous sodium sulfate. The solvent was removed under vacuum. Chromatography (50% methylene-ethylactate plus 5% methanol) afforded 0.22 g (85%) of product as a yellow solid: mp>200° C.

The HCl salt was prepared in ethanol: mp 261–263.5° C. Elemental analysis for C$_{28}$H$_{31}$FN$_4$.2HCl.H$_2$O; Calc'd: C, 63.03; H, 6.61; N, 10.50; Found: C, 63.39; H, 6.43; N, 10.21.

EXAMPLE 29a

3-[(1,$^4$-cis)-4-(4-Quinolin-8-yl-piperazin-1-yl)-cyclohexyl]-1H-indole-5-carbonitrile A solution of 4-(5-cyano-1-indol-3-yl)-cyclohexanone (1.47 g, 6.2 mmol), 8-(piperazin-1-yl)-quinoline (1.32 g, 6.2 mmol), sodium triacetoxyborohydride (2.0 g, 7.2 mmol) and acetic acid (0.71 ml, 12 mmol) in 1,2-dichloroethane (40 ml) was allowed to stir at room temperature overnight. The reaction was quenched with 1N sodium hydroxide (20 ml), extracted with methylene chloride (3×100 ml), and washed with brine (3×100 ml). The organic layer was dried over anhydrous sodium sulfate and filtered. Chromatography (5% methanol-ethyl acetate) afforded 1.48 g(55%) of product as a white solid: mp 149–151° C.

The HCl salt was prepared in ethanol: mp 209–212° C. Elemental analysis for C$_{27}$H$_{29}$FN$_4$.2HCl.0.75H$_2$O; Calc'd: C, 64.43; H, 6.28; N, 13.58; Found: C, 64,46; H, 6.29; N, 13.37.

EXAMPLE 29b

3-[(1,4-trans)-4-(4-Quinolin-8-yl-piperazin-1-yl)-cyclohexyl]-1H-indole-5-carbonitrile The trans compound was isolated at the same time as the cis isomer in 26% yield (0.55 g) as a white solid: mp 276–278° C.

The HCl salt was prepared in ethanol: mp 286–288° C. Elemental analysis for C$_{27}$H$_{29}$FN$_4$.2HCl.O0.5H$_2$O; Calc'd: C, 64.98; H, 6.23; N, 13.53; Found: C, 65.28; H, 5.96; N, 13.30.

EXAMPLE 30

1-Methyl-3-[(1,4-cis)-4-(4-quinolin-8-yi-piperazin-1-yl)-cyclohexyl]-1H-indole-5-carbonitrile To a suspension of sodium hydride (60%, 0.06 g, 1.4 mmol) in anhydrous N,N-dimethylformamide (8 ml) was added 3-[(1,4-cis)-4-(4-quinolin-8-yl-piperazin-1-yl)-cyclohexyl]-1H-indole-5-carbonitrile (0.30 g, 0.69 mmol) in 4 ml anhydrous N,N-dimethylformamide at room temperature. The mixture was stirred at room temperature for 30 minutes, followed by the addition of iodomethane (0.051 ml, 0.83 mmol) to the above solution. The resulting mixture was stirred at room temperature for 30 minutes and quenched with water. The mixture was extracted with ethyl acetate, dried over anhydrous sodium sulfate, and the solvent removed under vacuum. Chromatography (50% methylene-ethyl acetate plus 5% methanol) afforded 0.27 g 90%) of product as a light yellow solid: mp 208–209° C.

The HCl salt was prepared in ethanol: mp 288–289° C. Elemental analysis for C$_{29}$H$_{31}$N$_5$.2HCl.0.15C$_4$H$_{10}$O; Calc'd: C, 66.62; H, 6.52; N, 13.12; Found: C, 66.79; H, 6.74; N, 12.81.

EXAMPLE 31a

5-Fluoro-3-{(1,4-cis)-4-[4-(6-fluoro-chroman-8-yl)-piperazin-1-yl]-cyclohexyl}-1H-indole A solution of 4-(5-fluoro-1-indol-3-yl)-cyclohexanone (0.49 g, 2.1 mmol), 4-(6-fluoro-chroman-8-yl)-piperazine (0.5 g, 2.1 mmol), sodium triacetoxyborohydride (0.67 g, 3.2 mmol) and acetic acid (0.24 ml, 4.2 mmol) in 1,2-dichloroethane (20 ml) was allowed to stir at room temperature overnight. The reaction was quenched with 1N sodium hydroxide (20 ml), extracted with methylene chloride (3×100 ml), and washed with brine (3×100 ml). The organic layer was dried over anhydrous sodium sulfate and filtered. Chromatography (5% methanol-ethyl acetate) afforded 0.42 g (44%) of product as a white foam.

The HCl salt was prepared in ethanol: mp 199–200.5° C. Elemental analysis for C$_{27}$H$_{31}$F$_2$ON$_3$.HCl.0.5H$_2$O; Calc'd: C, 65.25; H, 6.69; N, 8.45; Found: C, 65.04; H, 6.61; N, 8.29.

EXAMPLE 31b

5-Fluoro-3-{(1,4-trans)-4-[4-(6-fluoro-chroman-8-yl)-piperazin-1-yl]-cyclohexyl}-1H-indole The trans compound was isolated at the same time as the cis isomer in 35% yield (0.33 g) as a clear oil.

EXAMPLE 32a

5-Fluoro-3-{(1,4-cis)-4-[4-(5-fluoro-2,3-dihydro-benzofuran-7-yl)-piperazin-1-yl]-cyclohexyl}-1H-indole A solution of 4-(5-fluoro-1-indol-3-yl)-cyclohexanone (0.52 g, 2.2 mmol), 4-(5-fluoro-2,3-dihydro-benzofuran-7-yl)-piperazine (0.5 g, 2.2 mmol), sodium triacetoxyborohydride (0.72 g, 3.4 mmol) and acetic acid (0.26 ml, 4.5 mmol) in 1,2-dichloroethane (20 ml) was allowed to stir at room temperature overnight. The reaction was quenched with 1N sodium hydroxide (20 ml), extracted with methylene chloride (3×100 ml), and washed with brine (3×100 ml). The organic layer was dried over anhydrous sodium sulfate and filtered. Chromatography (5% methanol-ethyl acetate) afforded 0.37 g (38%) of product as a white solid: mp 182–183.5° C.

The HCl salt was prepared in ethanol: mp 196–198° C. Elemental analysis for $C_{26}H_{29}F_2ON_3 \cdot HCl \cdot 0.5H_2O$; Calc'd: C, 64.65; H, 6.47; N, 8.70; Found: C, 64.45; H, 6.20; N, 8.60.

EXAMPLE 32b

5-Fluoro-3–1(1,4-trans)-4-[4-(5-fluoro-2,3-dihydro-benzofuran-7-yl)-piperazin-1-yl]-cyclohexyl}-1H-indole The trans compound was isolated at the same time as the cis isomer in 34% yield (0.34 g) as a clear oil.

The HCl salt was prepared in ethanol: mp 303–305° C. Elemental analysis for $C_{26}H_{29}F_2ON_3 \cdot HCl \cdot 0.5H_2O$; Calc'd: C, 64.65; H, 6.47; N, 8.70; Found: C, 64.86; H, 6.40; N, 8.36.

EXAMPLE 33a

3–1(1,4-cis)-4-[4-(5-Fluoro-2,3-dihydro-benzofuran-7-yl)-piperazin-1-yl]-cyclohexyl}-1H-indole-5-carbonitrile A solution of 4-(5-cyano-1-indol-3-yl)-cyclohexanone (0.46 g, 1.9 mmol), 4-(5-fluoro-2,3-dihydro-benzofuran-7-yl)-piperazine (0.43 g, 1.9 mmol), sodium triacetoxyborohydride (0.62 g, 2.9 mmol) and acetic acid (0.22 ml, 3.9 mmol) in 1,2-dichloroethane (20 ml) was allowed to stir at room temperature overnight. The reaction was quenched with 1N sodium hydroxide (20 ml), extracted with methylene chloride (3×100 ml), and washed with brine (3×100 ml). The organic layer was dried over anhydrous sodium sulfate and filtered. Chromatography (5% methanol-ethyl acetate) afforded 0.35 g (41%) of product as a white foam.

The HCl salt was prepared in ethanol: mp 298–301° C. Elemental analysis for $C_{27}H_{29}FON_4 \cdot HCl \cdot 0.75H_2O$; Calc'd: C, 65.58; H, 6.42; N, 11.33; Found: C, 65.38; H, 6.22; N, 11.14.

EXAMPLE 33b 3-f(1,4-trans)-4-[4-(5-Fluoro-2,3-dihydro-benzofuran-7-yl)-piperazin-1-yl]-cyclohexyl}-1H-indole-5-carbonitrile The trans compound was isolated at the same time as the cis isomer in 23% yield (0.20 g) as a white foam.

The HCl salt was prepared in ethanol: mp 330–331° C. Elemental analysis for $C_{27}H_{29}FON_4 \cdot HCl_{0.75}H_2O$; Calc'd: C, 65.58; H, 6.42; N, 11.33; Found: C, 65.17; H, 6.14; N, 10.97.

EXAMPLE 33c

3-{(1,4-cis)-4-[4-(5-Fluoro-2,3-dihydro-benzofuran-7-yl)-piperazin-1-yl]-cyclohexyl}-1-methyl-1H-indole-5-carbonitrile To a suspension of sodium hydride (60%, 0.036 g, 0.9 mmol) in anhydrous N,N-dimethylformamide (2 ml) was added 3-{(1,4-cis)-4-[4-(5-fluoro-2,3-dihydro-benzofuran-7-yl)-piperazin-1-yl]-cyclohexyl}-1H-indole-5-carbonitrile (0.2 g, 0.45 mmol) in 6 ml anhydrous N,N-dimethylformamide at room temperature. The mixture was stirred at room temperature for 30 minutes, followed by the addition of iodomethane (0.034 ml, 0.54 mmol) to the above solution. The resulting mixture was stirred at room temperature for 30 minutes, and quenched with water. The mixture was extracted with ethyl acetate, and the organic layer was dried over anhydrous sodium sulfate. The solvent was removed under vacuum. Chromatography (5% methanol-ethyl acetate) afforded 0.18 g (87%) of product as a white solid: mp 207–208° C.

The HCl salt was prepared in ethanol: mp 282–284° C. Elemental analysis for $C_{28}H_{31}FON_4 \cdot HCl$; Calc'd: C, 67.94; H, 6.52; N, 11.32; Found: C, 67.61; H, 6.39; N, 10.98.

EXAMPLE 34a

3-[(1,4-cis)-4-[4-(Benzofuran-7-yl-piperazin-1-yl)-cyclohexyl]-1H-indole-5-carbonitrile A solution of 4-(5-fluoro-1-indol-3-yl)-cyclohexanone (0.72 g, 3.1 mmol), 1-(7-benzofuranyl)piperazine (0.55 g, 2.8 mmol), sodium triacetoxyborohydride (0.84 g, 3.9 mmol) and acetic acid (0.18 g, 2.8 mmol) in 1,2-dichloroethane (80 ml) was allowed to stir at room temperature overnight. The reaction was quenched with 0.5 N sodium hydroxide (100 ml), extracted with methylene chloride (2×100 ml. The organic layer was dried over anhydrous magnesium sulfate and filtered. The solvent was removed, crystals appeared after 1 hour. The crystals were triturated with ethyl ether (80 ml) to afford 0.47 g (35%) of product as a white solid: mp 158–159° C.

The HCl salt was prepared in ethanol: mp 295–296° C. Elemental analysis for $C_{27}H_{28}ON_4 \cdot HCl \cdot 0.25H_2O$; Calc'd: C, 69.66; H, 6.39; N, 12.04; Found: C, 69.56; H, 6.38; N, 12.12.

EXAMPLE 34b

3-[(1,4-trans)-4-[4-(Benzofuran-7-yl-piperazin-1-yl)-cyclohexyl]-1H-indole-5-carbonitrile The remaining residue of the above reaction was purified by chromatography (acetone-methanol-hexanes: 3:5:3) to afford 0.17 g (12%) of product as a glass.

The HCl salt was prepared in ethanol: mp 330–331° C. Elemental analysis for $C_{27}H_{28}FON_4 \cdot HCl \cdot 0.75H_2O$; Calc'd: C, 65.58; H, 6.42; N, 11.33; Found: C, 65.17; H, 6.14; N, 10.97.

EXAMPLE 35

5-Fluoro-3-{4-[4-(2-methoxy-phenyl)-piperazin-1-yl]cyclohex-1-enyl}-1H-indole

This compound was prepared in the manner described above for Example 18 by replacing 4-(5-fluoro-1H-indol-3- yl)-cyclohexanone (1.71 g, 7.9 mmol) with 4-(5-fluoro-1H-3-indolyl)-cyclohex-3-enone in 32% (0.26 g) yield.

The HCl salt was prepared in ethyl acetate: mp 250° C. Elemental analysis for $C_{25}H_{28}OFN_3.HCl$; Calc'd: C, 67.94; H, 6.61; N, 9.51; Found: C, 66.47; H, 6.58; N, 9.38.

EXAMPLE 36

3-{4-[4-(1H-Indol-4-yl)-piperazin-1-yl]-cyclohex-1-enyl}-1H-indole-5-carbonitrile This compound was prepared in the manner described above for Example 18 by replacing with 4-(5-fluoro-1H-3-indolyl)-cyclohex-3-enone with 4-(5-cyano-1H-3-indolyl)-cyclohex-3-enone in (0.7 g, 2.96 mmol) in 62% (0.78 g) yield.

The HCl salt was prepared in ethyl acetate: mp 199–201° C. Elemental analysis for $C_{27}H_{27}N_5.2HCl$; Calc'd: C,66.25; H, 6.49; N, 14.31; Found: C, 66.43; H, 6.24; N, 14.27.

EXAMPLE 38

5-Fluoro-3-{cis-4-[4-(1H-indol-4-yl)-piperazinyl]-cyclohexyl}-1-methyl-1H-indole This compound was prepared in the manner described above for Example 2 by replacing with 4-(5-fluoro-1H-3-indolyl)-cyclohexone with 4-(5-fluoro-1-methyl-3-indolyl)-cyclohexone in (0.34 g, 1.4 mmol) in 34% (0.24 g) yield as a clear oil.

The HCl salt was prepared in ethanol: mp 247–249° C. Elemental analysis for $C_{27}H_{31}FN_4.2HCl.0.25H_2O$; Calc'd: C, 63.84; H, 6.65; N, 11.03; Found: C, 63.88; H, 6.51; N, 10.77.

EXAMPLE 39a

3-{(1,4-cis)-4-[4-(Quinoxalin-yl)-piperazin-1-yl]-cyclohexyl}-1-methyl-1H-indole-5-carbonitrile A solution of 4-(5-cyano-1H-3-indolyl)-cyclohexanone (443 mg, 1.87 inmol), Intermediate 34 (400 mg, 1.87 mmol), acetic acid (0.22 mL, 3.7 mmol), and sodium triacetoxyborohydride (590 mg, 2.8 mmol) in dichloroethane (50 mL) was stirred at room temperature overnight. The reaction was quenched with 1 M NaOH (100 mL) and extracted into $CH_2Cl_2$ (3×100 mL). The organic fractions were combined, dried over $Na_2SO_4$, and filtered. The resulting oil was purified by column chromatography (5% MeOH/EtOAc) yielding 130 mg (16%) of the product as a yellow solid: mp 223–225° C.

Elemental Analysis for $C_{27}H_{28}N_61.H_2O$; Calc'd C, 71.34; H, 6.65; N, 18.49; Found C, 71.02; H, 6.33; N, 18.03.

EXAMPLE 39b

3-{(1,4-trans)-4-[4-(Quinoxalin-yl)-piperazin-1-yl]-cyclohexyl}-1-methyl-1H-indole-5-carbonitrile The trans isomer was isolated at the same time as the cis isomer affording 240 mg (29%) of a pale yellow solid: mp 257–259° C. Elemental Analysis for $C_{27}H_{28}N_6.1H_2O$; Calc'd C, 71.34; H, 6.65; N, 18.49; Found C, 71.63; H, 6.38; N, 18.39.

EXAMPLE 40a

3-[(1,4-cis)-4-(4-Quinolin-5-yl-piperazin-1-yl)-cyclohexyl]-1H-indole-5-carbonitrile To a solution of 5-(1-piperazinyl)-quinoline (500 mg, 2.35 mmol), 4-(5-cyano-1H-3-indolyl)-cyclohexanone (540 mg, 2.35 mmol), and sodium triacetoxyborohydride (740 mg, 3.5 mmol) in dichloroethane (20 mL) was added acetic acid (0.27 mL, 4.7 mmol) and stirred overnight at room temperature. The reaction was quenched with 1 M NaOH (50 mL) and extracted in $CH_2Cl$ (3×100 mL). The organic fractions were combined, dried over $Na_2SO_4$, concentrated, filtered and chromatographed (5% MeOH/EtOAc) yielding 410 mg (41%) of the cis isomer as a white solid. The HCl salt was generated from EtOAc yielding a white solid: mp 220–223° C. Elemental Analysis for $C_{28}H_{29}N_5.HCl.1H_2O$; Calc'd C, 68.62; H, 6.58; N, 14.29; Found C, 68.99; H, 6.54; N, 14.06.

EXAMPLE 40b

3-[(1,4-trans)-4-(4-Quinolin-5-yl)-piperazin-1-yl)-cyclohexyl]-1H-indole-5-carbonitrile The trans isomer was isolated at the same time as the cis isomer in Example 40a affording 180 mg (18%) as a beige solid. The HCl salt was generated from EtOAc yielding a white solid: mp 210–21 1° C.

Elemental Analysis for $C_{28}H_{29}N_5.HCl.0.4H_2O$; Calc'd C, 70.17; H, 6.48; N, 14.62; Found C, 70.23; H, 6.21; N, 14.45.

EXAMPLE 40c

5-{4-[(1,4-cis)-4-(5-Fluoro-1H-indol-3-yl)-cyclohexyl]-piperazin-1-yl}-quinoline This compound was prepared in the same manner as the compound in Example 40a replacing 4-(5-cyano-1H-3-indolyl)-cyclohexanone with 4-(5-fluoro-1H-3-indolyl)-cyclohexanone (540 mg, 2.35 mmol) to afford 410 mg (41%) of a pale yellow solid: mp 220–223° C.; MS(+)ESI m/e 429 $[M+H]^+$.

EXAMPLE 40d

5-{4-[(1,4-trans)-4-(5-Fluoro-1H-indol-3-yl)-cyclohexl]-piperazin-1-yl}-isoquinoline The trans isomer was isolated at the same time as the cis isomer of Example 40c as the cis isomer of Example 40c affording 180 mg (18%) as a white solid: mp 210–211° C.; MS(+)ESI m/e 429 $[M+H]^+$.

EXAMPLE 40e

5-{4-[(1,4-cis)-4-(5-Fluoro-1-methyl-1H-indol-3-yl)-cyclohexyl]-piperazin-1-yl}-quinoline To a solution of NaH (38 mg, 0.94 mmol) in anhydrous DMF (4 mL) under nitrogen atmosphere was added a solution of 5-{4-[(1,4-cis)-4-(5-fluoro-1H-indol-3-yl)-cyclohexyl]-piperazin-1-yl}-quinoline (200 mg, 0.47 mmol) in DMF (6 mL). The mixture was stirred at room temperature 0.5 hour after which MeI (0.035 mL, 0.56 mmol) was added via syringe. The reaction mixture was stirred an additional 0.5 hour and then quenched with $H_2O$ (50 mL) and extracted with EtOAc (3×50 mL). The organic fractions were combined, dried over $Na_2SO_4$ and concentrated yielding 190 mg (92%) of a clear oil. The HCl salt was made from EtOAc affording a pale yellow solid: mp decomposes>270° C.

Elemental Analysis for $C_{28}H_{31}FN_4.HCl.0.75H_2O$; Calc'd C, 68.28; H, 6.86; N, 11.37; Found C, 68.34; H, 6.56; N, 11.26.

EXAMPLE 41a

5-Fluoro-3-[(1,4-cis)-4-(4-naphthalen-1-yl-piperazine-1-yl)-cyclohexyl]-1H-indole This compound was prepared in the same manner as the compound of Example 40a replacing 4-(5-cyano-1H-3- indolyl)-cyclohexanone with 4-(5-fluoro-1H-3-indolyl)-cyclohexanone (437 mg, 1.9 mmol) and 5-(1-piperazinyl)-quinoline with 1-(1-naphthyl)piperazine (410 mg, 1.9 mmol) affording 240 mg (29%) of the product as a white solid: mp 195–197° C.

Elemental Analysis for $C_{28}H_{30}FN_3$; Calc'd C, 78.66; H, 7.07; N, 9.83; Found C, 78.24; H, 7.06; N, 9.59.

EXAMPLE 41b

5-Fluoro-3-[(1,4-trans)-4-(4-naphthalen-1-yl-piperazine-1-yl)-cyclohexyl]-1H-indole The trans isomer was isolated at the same time as the cis isomer of Example 41a affording 70 mg (9%) of a white solid: mp 179–181° C.

Elemental Analysis for $C_{28}H_{30}FN_3$; Calc'd C, 78.66; H, 7.07; N, 9.83; Found C, 78.28; H, 7.05; N, 9.79.

EXAMPLE 42a

5-{4-[(1,4-cis)-4-(5-fluoro-1H-indol-3-yl)-cyclohexyl]piperazin-1-yl}-isoquinoline This compound was prepared in the same manner as described for the compound of Example 36a replacing 5-(trifluoromethylsulfonyloxy)-quinoline with 5-(trifluoromethylsulfonyloxy)-isoquinoline (12 g, 43.3 mmol) to afford an inseparable mixture of the desired product and impurities. The mixture was treated with TFA (10 mL), MeOH (10 drops), and $CH_2Cl_2$ (20 mL) at 0° C. and warmed to room temperature overnight. The resulting solution was concentrated and the redissolved in $CH_2CH_2$ and neutralized with $NaHCO_3$. The aqueous layer was extracted in $CH_2CH_2$ (3×100 mL) and EtOAc (3×100 mL), dried over $Na_2SO_4$, filtered and concentrated giving a bright orange oil. The oil was purified twice by column chromatography (10% $MeOH/CH_2Cl_2/NH_4OH$) but a highly colored impurity persisted. The 5-(1-piperazinyl)-isoquinoline (450 mg, 2.1 mmol), 4-(5-fluoro-1H-3-indolyl)-cyclohexanone (485 mg, 2.1 mmol) and sodium triacetoxyborohydride (672 mg, 3.2 mmol) were dissolved in dichloroethane (30 mL). Acetic acid (0.25 mL, 4.2 mmol) was added and the resulting solution stirred at ambient temperature overnight. The reaction mixture was quenched with 1 M NaOH (40 mL) and extracted in $CH_2CH_2$ (4×100 mL). The organic fractions were combined, dried over $Na_2SO_4$ and concentrated yielding a yellow oil which was purified by column chromatography (5% MeOH/EtOAc) affording 300 mg (33% from 5-(1-piperazinyl)isoquinoline)of the title compound as a beige solid: mp 209–21 1° C. Elemental Analysis for $C_{27}H_{29}FN_4$; Calc'd C, 75.67; H, 6.82; N, 13.07; Found C, 75.40; H, 6.83; N, 12.89.

EXAMPLE 42b

5-{4-[(1,4-trans)-4-(5-fluoro-1H-indol-3-yl)-cyclohexyl]piperazin-1-yl}-isoquinoline The trans isomer was isolated at the same time as the cis isomer of Example 42a affording 110 mg (12%) of a pink solid: mp 218–221° C.

Elemental Analysis for $C_{27}H_{29}FN_4.0.25H_2O$; Calc'd C, 74.89; H, 6.87; N, 12.94; Found C, 74.79; H, 6.79; N, 12.85.

EXAMPLE 43a

1{4-[(1,4-cis)-4-(5-Fluoro-1H-indol-3-yi)-cyclohexl]-piperazin-1-yl}-isoquinoline This compound was prepared in the same manner as the compound of Example 40a replacing 4-(5-cyano-1H-3-indolyl)-cyclohexanone with 4-(5-fluoro-1H-3-indolyl)-cyclohexanone (530 mg, 2.3 mmol) and 5-(1-piperazinyl)-quinoline with 1-(1-piperazinyl)-isoquinoline (500 mg, 2.3 mmol) affording 260 mg (27%) of the product as a pale yellow solid: mp 180–183° C.

Elemental Analysis for $C_{27}H_{29}FN_4.0.5H_2O$; Calc'd C, 74.11; H, 6.91; N, 12.81; Found C, 74.13; H, 6.58; N, 12.60.

EXAMPLE 43b

1{4-[(1,4-trans)-4-(5-Fluoro-1H-indol-3-yl)-cyclohexl]-piperazin-1-yl}-isoquinoline The trans isomer was isolated at the same time as the cis isomer of Example 43a affording 180 mg (18%) of a white solid: mp 232–235° C.

Elemental Analysis for $C_{27}H_{29}FN_4.0.25H_2O$; Calc'd C, 74.89; H, 6.87; N, 12.94; Found C, 74.68; H, 6.88; N, 12.64.

EXAMPLE 43c

1{4-[(1,4-cis)-4-(5-Cyano-1H-indol-3-yl)-cyclohexl]-piperazin-1-yl}-isoquinoline This compound was prepared in the same manner as the compound of Example 40a replacing 5-(1-piperazinyl)-quinoline with 1-(1-piperazinyl)-isoquinoline (500 mg, 2.3 mmol) affording 230 mg (23%) of the product as a pale yellow solid: mp 107–109° C.; HRMS EI m/e 435.2431 (M+).

EXAMPLE 43d

1{4-[(1,4-trans)-4-(5-Cyano-1H-indol-3-yl)-cyclohexl]-piperazin-1-yl}-isoquinoline The trans isomer was isolated at the same time as the cis isomer of Example 43c affording 170 mg (17%) of a white solid: mp 252–255° C.; MS(+)APCI m/e 436 $(M+H)^+$.

EXAMPLE 44a

8-{(1,4-cis)-4-[4-(5-Fluoro-1H-indol-3-yl)-cyclohexyl]-piperazin-1-yl}-6-methoxy-quinoline To a solution of 0.360 g of 6-Methoxy, 8-piperazino-Quinoline in 10 mL of $CH_2Cl_2$, was added 0.285 g of 4-(5-fluoro-1-H-3-indolyl)-cyclohexanone followed by 0.625 g of sodium triacetoxyborohydride and 0.09 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 75 mL of silica gel using 50% ethyl acetate/hexanes, 75% ethyl acetate/hexanes, and finally 100% ethyl acetate to give 0.053 g of the desired product: mp 226–227° C.; MS (ES) m/z (relative intensity): 459 (M+H+, 100).

EXAMPLE 44b

8-{(1,4-trans)-4-[4-(5-Fluoro-1H-indol-3-yl)-cyclohexyl]-piperazin-1-yl}-6-methoxy-quinoline The trans isomer of the compound of Example 44a was isolated at the same time as the cis isomer as an off white solid (0.013 g).mp 207–215° C. MS (ES) m/z (relative intensity): 459 (M+H+, 100).

EXAMPLE 44c

3-{(1,4-cis)-4-[4-(6-Methoxy-quinolin-8-yl)-piperazin-1-yl]-cyclohexyl}-1H-indole-5-carbonitrile To a solution of 1.0 g of 6-Methoxy, 8-piperazino-quinoline in 20 mL of $CH_2Cl_2$, was added 0.979 g of 3-(4-oxo-cyclohexyl)-1H-indole-5-carbonitrile followed by 1.3 g of sodium triacetoxyborohydride and 0.246 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 300 mL of silica gel using 2.5% MeOH/$CH_2Cl_2$ to give 0.550 g of the desired product: mp 183–185° C.; MS (ES) m/z (relative intensity): 466 (M+H+, 100). The hydrochloride was also prepared to give a yellow solid mp 183–185° C.

EXAMPLE 44d

3-{(1,4-trans)-4-[4-(6-Methoxy-quinolin-8-yl)-piperazin-1-yl]-cyclohexyl}-1H-indole-5-carbonitrile The trans isomer of the compound of Example 44c was isolated at the same time as the cis isomer as an off white solid (0.170 g) mp 148–152° C. MS (ES) m/z (relative intensity): 466 (M+H+, 100). The maleic acid salt was prepared to give an off white solid (0.129 g). mp 160–165° C.

EXAMPLE 45a

6-Chloro-8-{4-[(1,4-cis)-4-(5-fluoro-1H-indol-3-yl)-cyclohexyl]-piperazin-1-yl}-quinoline To a solution of 0.200 g of 6-Chloro, 8-piperazino-quinoline in 10 mL of $CH_2Cl_2$, was added 0.266 g of 4-(5-fluoro-1-H-3-indolyl)-cyclohexanone followed by 0.430 g of sodium triacetoxyborohydride and 0.09 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 75 mL of silica gel using 50% ethyl acetate/hexanes, and then 75% ethyl acetate/hexanes, to give 0.119 g of the desired product: mp 166–176° C.; MS (ES) m/z (relative intensity): 464 (M+H+, 100).

Elemental analysis for $C_{27}H_{28}ClFN_4$; Calculated: C: 70.04; H: 6.1; N:12.1; Found: C: 70.07; H: 6.33; N: 11.87.

EXAMPLE 45b

6-Chloro-8-{4-[(1,4-trans)-4-(5-fluoro-1H-indol-3-yl)-cyclohexyl]-piperazin-1-yl}-quinoline The trans isomer of the compound of Example 45a was isolated at the same time as the cis isomer as an off white solid (0.026 g) mp 209–210° C. MS (ES) m/z (relative intensity): 464 (M+H+100). Elemental analysis for $C_{27}H_{28}ClFN_4$;

Calculated: C : 70.04; H : 6.1; N: 12.1; Found: C: 70.23; H: 6.33; N: 11.94.

EXAMPLE 45c

3-{(1,4-cis)-4-[4-(6-Chloro-quinolin-8-yl)-piperazin-1-yl]-cyclohexyl}-1H-indole-5-carbonitrile To a solution of 0.250 g of 6-chloro, 8-piperazino-quinoline in 10 mL of $CH_2Cl_2$, was added 0.240 g of 3-(4-oxo-cyclohexyl)-1H-indole-5-carbonitrile followed by 0.532 g of sodium triacetoxyborohydride and 0.09 mL acetic acid. The reaction was stirred at room temperature overnight. It was quenched with 1N NaOH, and the product was extracted with ether. The organic phase was washed with water and dried. The product was filtered through 75 mL of silica gel using 25% ethyl acetate/hexanes, and then 75% ethyl acetate/hexanes, to give 0.123 g of the desired product: mp 152–160° C.; MS (ES) m/z (relative intensity): 471 (M+H+, 100).

EXAMPLE 45d

3-{(1,4-trans)-4-[4-(6-Chloro-quinolin-8-yl)-piperazin-1-yl]-cyclohexyl}-1H-indole-5-carbonitrile The trans isomer of the compound of Example 45c was isolated at the same time as the cis isomer as an off white solid (0.032 g) mp 144–152° C. MS (ES) m/z (relative intensity): 471 (M+H+, 100).

EXAMPLE 46a

5-Chloro-8-{4-[(1,4-cis)-4-(5-fluoro-1H-indol-3-yl)-cyclohexyl]-piperazin-1-yl}-quinoline To a solution of 0.250 g of 5-chloro, 8-piperazino-quinoline in 10 mL of $CH_2Cl_2$, was added 0.200 g of 4-(5-fluoro-1-H-3-indolyl)-cyclohexanone followed by 0.533 g of sodium triacetoxyborohydride and 0.09 mL acetic acid. The reaction was stirred at room temperature overnight. It was quenched with 1N NaOH, and the product was extracted with ether. The organic phase was washed with water and dried over magnesium sulfate. The product was filtered through 75 mL of silica gel using 25% ethyl acetate/hexanes, 75% ethyl acetate/hexanes, to give 0.074 g of the desired product: mp 101–104° C.; MS (ES) m/z (relative intensity): 464 (M+H+, 100).

EXAMPLE 46b

3-{(1,4-cis)-4-[4-(5-Chloro-quinolin-8-yl)-piperazin-1-yl]-cyclohexyl}-1H-indole-5-carbonitrile To a solution of 0.300 g of 5-chloro, 8-piperazino-quinoline in 10 mL of $CH_2Cl_2$, was added 0.230 g of 3-(4-oxo-cyclohexyl)-1H-indole-5-carbonitrile followed by 0.550 g of sodium triacetoxyborohydride and 0.09 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 75 mL of silica gel using 50% ethyl acetate/hexanes, 75% ethyl acetate/hexanes, and finally 100% ethyl acetate to give 0.051 g of the desired product: mp 135–144° C.; MS (ES) m/z (relative intensity): 471 (M+H+, 100).

EXAMPLE 47a

5-Fluoro-8-{4-[(1,4-cis)-4-(6-fluoro-1H-indol-3-yl)-cyclohexyl]-piperazin-1-yl}-quinoline To a solution of 0.231 g of 5-fluoro, 8-piperazino-quinoline in 10 mL of $CH_2Cl_2$, was added 0.230 g of 4-(6-fluoro-1-H-3-indolyl)-cyclohexanone followed by 0.530 g of sodium triacetoxyborohydride and 0.09 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 100% ethyl acetate, then 6% MeOH/ethyl acetate to give 0.049 g of the desired product: mp 172–174° C.; MS (ES) m/z (relative intensity): 447 (M+H+, 100).

EXAMPLE 47b

5-Fluoro-8-{4-[(1,4-trans-4-(6-fluoro-1H-indol-3-yl)-cyclohexyl]piperazin-1-yl}-quinoline The trans isomer of the compound of Example 47a was isolated at the same time as the cis isomer as an off white solid (0.055 g) mp173–175° C. MS (ES) m/z (relative intensity): 447 (M+H+, 100).

EXAMPLE 48a

3-{(1,4-cis)-4-[4-(2-Methyl-quinolin-8-yl)-piperazin-1-yl]-cyclohexyl}-1H-indole-5-carbonitrile To a solution of 0.230 g of 8-piperazino-quinaldine in 10 mL of $CH_2Cl_2$, was added 0.238 g of 3-(4-oxo-cyclohexyl)-1H-indole-5-carbonitrile followed by 0.527 g of sodium triacetoxyborohydride and 0.09 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 100% ethyl acetate and finally 10% MeOH/ethyl acetate to give 0.089 g of the desired product: mp 197–199° C.; MS (ES) m/z (relative intensity): 450 (M+H+, 100).

EXAMPLE 48b

3-{(1,4-trans)-4-[4-(2-Methyl-quinolin-8-yl)-piperazin-1-yl]-cyclohexyl}-1H-indole-5-carbonitrile The trans isomer of the compound of Example 48a was isolated at the same time as the cis isomer as an off white solid (0.058 g) mp 268–280° C. MS (ES) m/z (relative intensity): 450 (M+H+, 100).

EXAMPLE 49a

4-{4-[(1,4-cis)-4-(5-Fluoro-1H-indol-3-yl)-cyclohexyl]-piperazin-1-yl}-2-trifluoromethyl-quinoline To a solution of 0.281 g of 1-[2-(trifluoromethyl)quinol-4yl]piperazine in 10 mL $CH_2Cl_2$, was added 0.231 g of 4-(5-fluoro-1-H-3-indolyl)-cyclohexanone followed by 0.528 g of sodium triacetoxyborohydride and 0.09 mL acetic acid. The reaction was stirred at room temperature overnight. It was quenched with 1N NaOH, and the product was extracted with ether. The organic phase was washed with water and dried over magnesium sulfate. The product was filtered through 100 mL of silica gel using 25% ethyl acetate/hexanes,then 50% ethyl acetate/hexanes, to give 0.089 g of the desired product: mp 235–239° C.; MS (ES) m/z (relative intensity): 497 (M+H+, 100).

EXAMPLE 49b

4-{4-[(1,4-trans)-4-(5-Fluoro-1H-indol-3-yl)-cyclohexyl]-piperazin-1-yl)-2-trifluoromethyl-quinoline The trans isomer of the compound of Example 49A was isolated at the same time as the cis isomer as an off white solid (0.110 g) mp218–223° C. MS (ES) m/z (relative intensity): 497 (M+H+, 100).

EXAMPLE 49c

3-{(1,4-cis)-4-[4-(2-Trifluoromethyl-quinolin-4-yl)-piperazin-1-yl]-cyclohexyl}-1H-indole-5-carbonitrile This compound was prepared in the same manner as in Example 49a replacing 4-(5-fluoro-1-H-3-indolyl)-cyclohexanone with 3-(4-oxo-cyclohexyl)-1H-indole-5-carbonitrile tto afford 0.137 g of a white solid. mp 235–239° C.; MS (ES) m/z (relative intensity): 504 (M+H+, 100).

Elemental analysis for $C_{29}H_{28}F_3N_5$; Calculated: C: 69.17; H: 5.6; N: 13.91; Found: C: 68.96; H: 5.37; N: 13.8.

EXAMPLE 49d

3-{(1,4-trans)-4-[4-(2-Trifluoromethyl-quinolin-4-yl)-piperazin-1-yl]-cyclohexyl}-1H-indole-5-carbonitrile The trans isomer of the compound of Example 49C was isolated at the same time as the cis isomer as an off white solid (0.036 g) mp 259–264° C. MS (ES) m/z (relative intensity): 504 (M+H+, 100).

EXAMPLE 50a

4-{4-[(1,4-cis)-4-(5-Fluoro-1H-indol-3-yl)-cyclohexyl]-piperazin-1-yl}-6-methoxy-quinoline To a solution of 0.280 g of 6-methoxy-4-piperazino-quinoline in 10 mL $CH_2Cl_2$, was added 0.230 g of 4-(5-fluoro-1-H-3-indolyl)-cyclohexanone followed by 0.530 g of sodium triacetoxyborohydride and 0.09 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 100% ethyl acetate, then 10% MeOH/ethyl acetate, to give 0.036 g of the desired product: mp 222–227° C.; MS (ES) m/z (relative intensity): 459 (M+H+, 100).

EXAMPLE 50b

4-{4-[(1,4-trans)-4-(5-Fluoro-1H-indol-3-yl)-cyclohexyl]-piperazin-1-yl}-6-methoxy-quinoline The trans isomer of the compound of Example 50a was isolated at the same time as the cis isomer as an off white solid (0.027 g) mp 249–251° C. MS (ES) m/z (relative intensity): 459 (M+H+, 100).

EXAMPLE 50c

3-{(1,4-cis)-4-[4-(6-Methoxy-quinolin-4-yl)-piperazin-1-yl]-cyclohexyl}-1H-indole-5-carbonitrile This compound was prepared in the same manner as in Example 50a replacing 4-(5-fluoro-1-H-3-indolyl)-cyclohexanone with 3-(4-oxo-cyclohexyl)-1H-indole-5-carbonitrile to afford 0.016 g of a white solid. mp 271–272° C.; MS (ES) m/z (relative intensity): 466 (M+H+, 100).

EXAMPLE 50d

3-{(1,4-trans)-4-[4-(6-Methoxy-quinolin-4-yl)-piperazin-1-yl]-cyclohexyl}-1H-indole-5-carbonitrile The trans isomer of the compound of Example 50c was isolated at the same time as the cis isomer as an off white solid (0.014 g) mp 288–292° C.MS (ES) m/z (relative intensity): 466 (M+H+, 100).

EXAMPLE 51a (cis)-3-{4-[4-(6-methoxy-2-methylquinolin-8-yl)piperazin-1-yl]cyclohexyl}-1-methyl-1H-indole-5-carbonitrile To a mixture of 4-(6-methoxy-2-methylquinolin-8-yl)piperazine (300 mg, 1.16 mmol), 3-(1-methyl-1H-indole-5- carbonitrile)cyclohexane-4-one (440 mg, 1.75 mmol), and sodium triacetoxyborohydride (495 mg, 2.34 mmol) in 5 mL of anhydrous THF was added 70 [L (73 mg, 1.22 mmol) glacial acetic acid. The resulting mixture was stirred at ambient temperature under $N_2$ for 24 hours. The reaction was treated with saturated aqueous sodium bicarbonate (50 mL), and aqueous mixture was extracted with $CH_2CL_2$ (3×50 mL). The organic layers were combined, dried over anhydrous $Na_2SO_4$, filtered, and concentrated in vacuo. Flash chromatography on 4×15 cm $SiO$, (gradient elution, 50% EtOAc/hex to 100% EtOAc then 5% MeOH/EtOAc) afforded still impure title compound. A second chromatography using the same eluent on 2×20 cm $SiO_2$ afforded 190 mg (33%) of clean product and 140 mg of still impure product. Recrystallization of the clean product from EtOAc/hexane afforded 100 mg (17%) of the title compound: mp 201–203° C.

Elemental analysis for $C_{31}H_{35}N_5O.0.1C_4H_8O_2$; Calc'd: C, 75.06; H, 7.18; N, 13.94; Found: C, 75.00; 7.32; N, 13.83.

EXAMPLE 51b (cis)-3-{4-[4-(6-methoxy-3-methylquinolin-8-yl) piperazin-1-yl]cyclohexyl}-1-methyl-1H-indole-5-carbonitrile To a mixture of 4-(6-methoxy-3-methylquinolin-8-yl) piperazine (210 mg, 0.82 mmol), 3-(1-methyl-1H-indole-5-carbonitrile)cyclohexane-4-one (330 mg, 1.31 mmol), and sodium triacetoxyborohydride (435 mg, 2.05 mmol) in 5 mL of anhydrous THF was added 55 mL (68 mg, 0.96 mmol) glacial acetic acid. The resulting mixture was stirred at ambient temperature under $N_2$ for 24 hours. The reaction was treated with saturated aqueous sodium bicarbonate (50 mL), and the aqueous mixture was extracted with $CH_2CH_2$ (3×50 mL). The organic layers were combined, dried over anhydrous $Na_2SO_4$, filtered, and concentrated in vacuo. Flash chromatography on 2×20 cm $SiO_2$ (5% MeOH/EtOAc) Afforded the title compound, which was slightly impure. Recrystallization from EtOAc/hexane afforded 0.26 g (64%) of the title compound: mp 190–191.5° C.

Elemental analysis for $C_{31}H_{35}N_5O$; Calc'd: C, 75.43; H, 7.15; N, 14.19; Found: C, 75.13; 7.25; N, 14.01.

EXAMPLE 51c (cis)-3–14-[4-(6-methoxy-4-methylquinolin-8-yl) piperazin-1-yl]cyclohexy11–1-methyl-1H-indole-5-carbonitrile To a mixture of 4-(6-methoxy-4-methylquinolin-8-yl) piperazine (0.2 g, 0.78 mmol), 3-(1-methyl-1H-indole-5-carbonitrile)cyclohexane-4-one (0.215 g, 0.85 mmol), dichloroethane (10 mL) and glacial acetic acid (0.12 mL) was added sodium triacetoxyborohydride (0.25 g, 1.16 mmol). The reaction mixture was stirred at ambient temperature for 24 hours. The reaction mixture was diluted with dichloromethane (60 ml), washed with 1N aqueous sodium hydroxide (2×50 mL), water (50 mL), and brine (50 mL). The organic layer was dried over anhydrous sodium sulfate, filtered and concentrated to give 0.43 g of crude product. Flash chromatography on 50 g of silica gel (5% methanol/ethyl acetate) afforded 0.15 g (40%) of the title compound. Recrystallization from ethyl acetate/hexane yielded 0.085 g (23%) of pure product: mp 210–212° C.

Elemental analysis for $C_{31}H_{35}N_5O.0.0.25H_2O$; Calc'd: C, 74.74; H, 7.18; N, 14.06; Found: C, 74.82; H, 7.12; N, 14.11.

EXAMPLE 51d (trans)-3-{4-[4-(6-methoxy-4-methylquinolin-8-yl) piperazin-1-yl]cyclohexyl}-1-methyl-1H-indole-5-carbonitrile The trans isomer was isolated at the same time as the cis isomer in 16% yield (0.062 g). Trituration with ethyl acetate/hexane afforded 0.058 g (15%) of pure title compound: mp 230–232° C.

Elemental analysis for $C_{31}H_{35}N_5O.0.5H_2O$; Calc'd: C, 74.07; H, 7.22; N, 13.93; Found: C, 74.12; H, 7.10; N, 13.95.

EXAMPLE 52a (cis)-3-{4-[4-(6-methoxy-5-methylquinolin-8-yl) piperazin-1-yl]cyclohexyl}-1-methyl-1H-indole-5-carbonitrile The above compound was prepared utilizing the same method as that used for the preparation of (cis)-3-{4-[4-(6-methoxy-4-methylquinolin-8-yl)piperazin-1-yl]-cyclohexyl}-1-methyl-1H-indole-5-carbonitrile to give 0.25 g of the title compound. Recrystallization from ethyl acetate afforded 0.125 g (20%) of pure product: mp 227–228° C.

Elemental analysis for $C_{33}H_{35}N_5O.0.25H_2O$; Calc'd: C, 74.74; H, 7.18; N, 14.06; Found: C, 74.61; H, 7.20; N, 13.71.

EXAMPLE 52b (trans)-3-{4-[4-(6-methoxy-5-methylquinolin-8-yl) piperazin-1-yl]cyclohexyl}-1-methyl-1H-indole-5-carbonitrile The trans isomer (0.15 g) was isolated at the same time as the cis compound. Trituration from ethyl acetate afforded 0.110 g (18%) of pure product: mp 212–213° C.

Elemental analysis for $C_{31}H_{35}N_5O.0.25H_2O$; Calc'd: C, 75.43; H, 7.15; N, 14.19; Found: C, 75.09; H, 7.10; N, 13.96.

EXAMPLE 52c (cis)-5-chloro-8-{4-[-(5-fluoro-1-methyl-1H-indol-3-yl)cyclohexyl]piperazin-1-yl}-6-methoxyquinoline The above compound was prepared utilizing the same method as that used for the preparation of (cis)-3-{4-[4-(6-methoxy-4-methylquinolin-8-yl)piperazin-1-yl]-cyclohexyl}-1-methyl-1H-indole-5-carbonitrile to give 0.13 g of the title compound. Trituration from ethyl acetate afforded 0.120 g (29%) of pure product.

Elemental analysis for $C_{29}H_{32}ClFN_4O$; Calc'd: C, 68.70; H, 6.36; N, 11.05; Found: C, 68.45; H, 6.24; N, 10.89.

EXAMPLE 52d (trans)-5-chloro-8-{4-[-(5-fluoro-1-methyl-1H-indol-3-yl)cyclohexyl]piperazin-1-yl}-6-methoxyquinoline The trans isomer was isolated in 19% yield (0.075 g) at the same time as the cis compound. Trituration from ethyl acetate afforded 0.070 g (17%) of pure product: mp 170–171° C.

Elemental analysis for $C_{29}H_{32}ClFN_4O$; Calc'd: C, 68.70; H, 6.36; N, 11.05; Found: C, 68.44; H, 6.32; N, 11.02.

EXAMPLE 52e (cis)-3-{4-[4-(5-chloro-6-methoxyquinolin-8-yl) piperazin-1-yl]cyclohexyl}-1-methyl-1H-indole-5-carbonitrile The above compound was prepared utilizing the same method as that used for the preparation of (cis)-3-{4-[4-(6-methoxy-4-methylquinolin-8-yl)piperazin-1-yl]-cyclohexyl}-1-methyl-1H-indole-5-carbonitrile to give 0.1 g (24%) of title compound. Recrystallizion from ethyl acetate afforded 0.080 g (20%) of pure product: mp 231–231° C.

Elemental analysis for $C_{30}H_{32}ClN_5O.0.25H_2O$; Calc'd: C, 69.48; H, 6.32; N, 13.50; Found: C, 69.49; H, 6.31; N, 13.29.

EXAMPLE 52f (trans)-3-{4-[4-(5-chloro-6-methoxyquinolin-8-yl)piperazin-1-yl]cyclohexyl}-1-methyl-1H-indole-5-carbonitrile The trans isomer was isolated in 22% yield (0.095 g) at the same time as the cis compound. Trituration from ethyl acetate afforded 0.070 g (17%) of pure product: mp 215–216° C.

Elemental analysis for $C_{30}H_{32}ClN_5O.0.25H_2O$; Calc'd: C, 69.48; H, 6.32; N, 13.50; Found: C, 69.36; H, 6.28; N, 13.27.

EXAMPLE 53a

4-{4-[(1,4-cis)-4-(1H-indol-3-yl)cyclohexyl]piperazin-1-yl}-2-(trifluoromethyl)-1H-benzimidazole To a solution of 4-piperazin-1-yl-2-trifluoromethyl-1H-benzoimidazole (400 mg, 1.48 mmol), 4-(1H-3-indolyl)-cyclohexanone (315 mg, 1.48 mmol), and sodium triacetoxyborohydride (470 mg, 2.22 mmol) in dichloroethane (30 mL) was added acetic acid (0.20 mL, 2.96 mmol) and stirred overnight at room temperature. The reaction was quenched with 1 M NaOH (50 mL) and extracted in $CH_2Cl_2$ (2×100 mL) and 50% EtOAc/MeOH (3×100 mL). The organic fractions were combined, dried over $Na_2SO_4$, concentrated, filtered and chromatographed twice (5% MeOH/EtOAc) yielding 170 mg (25%) of the cis isomer as a white solid. The HCl salt was generated from EtOAc yielding a white solid: mp foams above 207° C.

Elemental analysis for $C_{26}H_{28}F_3N_5.HCl.H_2O$; Calc'd: C, 59.82; H, 5.99; N, 13.42; Found: C, 60.18; H, 5.84; N, 13.29.

EXAMPLE 53b

4-{4-[(1,4-trans)-4-(1H-indol-3-yl)cyclohexyl]piperazin-1-yl}-2-(trifluoromethyl)-1H-benzimidazole The trans isomer was isolated at the same time affording 180 mg (9%) as a beige solid. The HCl salt was generated from EtOAc yielding a white solid: mp decomposes above 200° C.

Elemental analysis for $C_{26}H_{28}F_3N_5.HCl.0.75H_2O$; Calc'd: C, 60.34; H, 5.94; N, 13.53; Found: C, 60.37; H, 5.68; N, 13.43.

EXAMPLE 54a

4-{4-[(1,4-cis)-4-(1H-indol-3-yl)cyclohexyl]piperazin-1-yl}-1H-benzimidazole

This compound was prepared as described for 1a replacing 4-piperazin-1-yl-2-trifluoromethyl-1H-benzoimidazole with 4-piperazin-1-yl-1H-benzoimidazole (510 mg, 2.5 mmol) to afford 350 mg (34%) of the title compound as a yellow foam which was triturated with $Et_2O$ to give a white solid: mp 217–219° C.

Elemental analysis for $C_{25}H_{29}N_5$; Calc'd: C, 75.16; H, 7.32, N, 17.53; Found: C, 74.82; H, 7.21; N, 17.05.

EXAMPLE 54b

4-{4-[(1,4-trans)-4-(1H-indol-3-yl)cyclohexyl]piperazin-1-yl}-1H-benzimidazole

The trans isomer was isolated at the same time affording 200 mg (20%) as a white solid. The HCl salt was generated from $Et_2O$/EtOH to give a white solid: mp decomposes above 215° C.

Elemental analysis for $C_{25}H_{29}N_5.2HCl.H_2O$; Calc'd: C, 61.22; H, 6.78; N, 14.28; Found: C, 61.24; H, 6.97; N, 14.09.

EXAMPLE 55a

4-{4-[(1,4-cis)-4-(1H-indol-3-yl)cyclohexyl]piperazin-1-yl}-2-methyl-1H-benzimidazole This compound was prepared as described for Example 53a replacing 4-piperazin-1-yl-2-trifluoromethyl-1H-benzoimidazole with 4-piperazin-1-yl-2-methyl-1H-benzoimidazole (340 mg, 1.57 mmol) to afford 350 mg (54%) of the title compound as a white foam. The HCl salt was generated from EtOAc to give a white solid: mp decomposes above 190° C.

Elemental analysis for $C_{26}H_{31}N_5.2HCl.H_2O$; Calc'd: C, 61.90; H, 6.99; N, 13.88; Found: C, 62.26; H, 7.18; N, 13.46.

EXAMPLE 55b

4-{4-[(1,4-trans)-4-(1H-indol-3-yl)cyclohexyl]piperazin-1-yl}-2-methyl-1H-benzimidazole The trans isomer was isolated at the same time affording 110 mg (17%) as a white solid. The HCl salt was generated from $EtOH/Et_2O$ to give a white solid: mp decomposes above 220° C.

Elemental Analysis for $C_{25}H_{29}N_5.2HCl.1.5H_2O$; Calc'd: C, 60.81; H, 7.07; N, 13.64; Found: C, 60.84; H, 7.04; N, 13.31.

EXAMPLE 56

3-{4-[(1,4-cis)-4-(6-methoxyquinolin-5-yl)piperazin-1-yl]cyclohexyl}-1H-indole-5-carbonitrile To an oven-dried 100 mL flask under $N_2$ atmosphere was added 5-bromo-6-methoxyquinoline (3 g, 12.6 mmol), piperazine (6.5 g. 75.6 mmol), $Pd(dba)_2$ (570 mg, 5 mol %), $P(t-Bu)_3$ (0.628 mL, 5 mol %) and sodium t-butoxide (1.82 g, 18.9 mmol). 50 mL dry o-xylene was added and the reaction mixture stirred and heated at 120° C. for 3 hours, then at room temperature overnight. The reaction mixture was poured into $H_2O$ (100 mL) and extracted into EtOAc (3×100 mL). The organic fractions were combined, dried over $Na_2SO_4$, concentrated and purified by column chromatography (10% $MeOH/CH_2Cl_2$+NH1OH) affording 170 mg (6%) of 6-methoxy-5-piperazin-1-yl-quinoline. This material was used without further purification (combined with another batch) in the next step. (Ref: Tet Lett. 1998, 39, p. 617–620).

To a solution of 6-methoxy-5-piperazin-1-yl-quinoline (220 mg, 0.9 mmol), 4-(5-cyano-1H-3-indolyl)-cyclohexanone (215 mg, 0.9 mmol), and sodium triacetoxyborohydride (288 mg, 1.36 mmol) in dichloroethane (20 nmL) was added acetic acid (0.10 mL, 1.75 mmol) and stirred overnight at room temperature. The reaction was quenched with 2.5 M NaOH (20 mL) and $H_2O$ (150 mL) then extracted in $CH_2Cl_2$ (2×100 mL) and 5% MeOH/EtOAc (3×100 mL). The organic fractions were combined, dried over $Na_2SO_4$, concentrated, filtered and chromatographed (5% MeOH/EtOAc) yielding 140 mg (33%) of the cis isomer as a yellow glass. The HCl salt was generated from EtOAc yielding a yellow solid: mp discolors above 85° C.

Elemental analysis for $C_{26}H_{31}N_5.3HCl.H_2O$; Calc'd: C, 58.74; H, 6.12; N, 11.81; Found: C, 58.67; H, 6.34; N, 11.47.

EXAMPLE 57

2-{4-(1,4-trans)-[4-(6-Bromoquinolin-8-yl)piperazin-1-yl]cyclohexyl}-1-methyl-1H-indole-5-carbonitrile To a solution of 6-bromo-8-piperazin-1-yl-quinoline (1 g, 3.4 mmol), 4-(5-cyano-1-methyl-1H-3-indolyl)- cyclohexanone (857 mg, 3.4 mmol), and sodium triacetoxyborohydride (1.08 g, 5.1 mmol) in dichloroethane (40 mL) was added acetic acid (0.40 mL, 6.8 mmol) and stirred overnight at room temperature. The reaction was quenched with 2.5 M NaOH (20 mL) and $H_2O$ (150 mL) then extracted in $CH_2Cl_2$ (2×100 mL) and 5% MeOH/EtOAc (3×100 mL). The organic fractions were combined, dried over $Na2SO_4$, concentrated, filtered and chromatographed (5% MeOH/EtOAc) yielding 360 mg (20%) of the trans isomer as a white foam. The HCl salt was generated from EtOAc to give a white solid: mp decomposes above 85° C.

Elemental analysis for $C_{29}H_{30}BrN_5.HCl.0.75H_2O$; Calc'd: C, 60.21; H, 5.66; N, 12.11; Found: C, 60.17; H, 5.44; N, 11.99.

EXAMPLE 58a (Cis)-6-bromo-8-{4-[4-(5-fluoro-1-methyl-1H-indol-3-yl)cyclohexyl]piperazin-1-yl}quinoline To a solution of 6-bromo-8-piperazin-1-yl-quinoline (610 mg, 2.09 mmol), 4-(5-fluoro-1-methyl-1H-indol-3-yl)-cyclohexanone (510 mg, 2.09 mmol), and sodium triacetoxyborohydride (660 mg, 3.14 mmol) in dichloroethane (40 mL) was added acetic acid (0.24 mL, 4.18 mmol) and stirred overnight at room temperature. The reaction was quenched with 1 M NaOH (50 mL) and $H_2O$ (100 mL) then extracted in $CH_2Cl_2$ (100 mL) and EtOAc (100 mL). The organic fractions were combined, dried over $Na_2SO_4$, concentrated, filtered and chromatographed (5% MeOH/EtOAc). The majority of the cis compound precipitated out of 5% MeOH/EtOAc before application to the column and was purified by filtration affording 510 mg (47%) of the cis isomer as a pale yellow solid: mp 215–217° C.

Elemental analysis for $C_{28}H_{30}BrFN_4.0.5H_2O$; Calc'd: C, 60.21; H, 5.66; N, 12.11; Found: C, 60.17; H, 5.44; N, 11.99.

EXAMPLE 58b (Trans)-6-bromo-8-{4-[4-(5-fluoro-1-methyl-1H-indol-3-yl)cyclohexyl]piperazin-1-yl}quinoline The trans isomer was isolated by chromatography affording 210 mg (19%) as a pale yellow foam. The HCl salt was generated from EtOAc to give a gray solid: mp decomposes above 225° C.

Elemental analysis for $C_{28}H_{30}BrFN_4.HCl.0.5H_2O$; Calc'd: C, 59.32; H, 5.69; N, 9.88; Found: C, 59.36; H, 5.47; N, 9.79.

EXAMPLE 59a

3-{4-(1,4-cis)-4-(6-ethoxyquinolin-8-yl)piperazine-1-yl]cyclohexyl}-1-methyl-1H-indole-5-carbonitrile To a solution of 6-ethoxy-8-piperazin-1-yl-quinoline (500 mg, 1.95 mmol), 4-(5-cyano-1-methyl-1H-indol-3-yl)-cyclohexanone (490 mg, 1.95 mmol), and sodium triacetoxyborohydride (620 mg, 2.93 mmol) in dichloroethane (40 mL) was added acetic acid (0.25 mL, 3.9 mmol) and stirred overnight at room temperature. The reaction was quenched with 1 M NaOH (100 mL) and $H_2O$ (50 mL) then extracted in $CH_2Cl_2$ (50 mL) and 5% MeOH/EtOAc (2×100 mL). The organic fractions were combined, dried over $Na_2SO_4$, concentrated, filtered and chromatographed (5% MeOH/EtOAc). The majority of the cis compound precipitated out of 5% MeOH/EtOAc before application to the column and was purified by filtration and combined with the column fractions affording 450 mg (47%) of the cis isomer as an off-white solid: mp decomposes above 215° C.

Elemental analysis for $C_{31}H_{35}N_5O.1.25H_2O$; Calc'd: C, 72.14; H, 7.32; N, 13.57; Found: C, 72.23; H, 7.06; N, 13.35.

EXAMPLE 59b

3–14-(1,4-trans)-4-(6-ethoxyquinolin-8-yl)piperazine-1-yl]cyclohexyl}-1-methyl-1H-indole-5-carbonitrile The trans isomer was isolated at the same time by chromatography affording 210 mg (22%) as a yellow foam which was triturated with $Et_2O$ to afford a pale yellow solid: mp 225–228° C.

Elemental Analysis for $C_{31}H_{35}N_5O.H_2O$; Calc'd: C, 72.77; H, 7.29; N, 13.69; Found: C, 72.79; H, 7.07; N, 13.41.

EXAMPLE 60

3-[4-(4-{6-[benzyl(methyl)amino]quinolin-8-yl}piperazin-1-yl)cyclohexyl]-1-methyl-1H-indole-5-carbonitrile To an oven-dried 10 mL round bottom flask under a $N_2$ atmosphere was added $Cs_2CO_3$ (173 mg, 0.53 mmol), BINAP (15 mg, 3 mol %), $Pd(OAc)_3$ (5 mg, 3 mol %) and 2-{4-(1,4-trans)-[4-(6-bromoquinolin-8-yl)piperazin-1-yl]cyclohexyl}-1-methyl-1H-indole-5-carbonitrile (200 mg, 0.38 mmol). Toluene (1 ML) and benzylmethylamine (0.06 mL, 0.45 mmol) were added via syringe, and the reaction mixture was heated at 100° C. overnight. The cooled reaction mixture was diluted with $Et_2O$ (15 mL), filtered to remove solids, and concentrated. The resulting oil was purified by column chromatography (5%MeOH/EtOAc+$NH_4OH$) to give 60 mg of the title compound as a brown solid. The HCl salt was generated from EtOAc/$Et_2O$ affording an orange solid: mp decomposes above 90° C.

Elemental analysis for $C_{37}H_4ON_6.3HCl$; Calc'd: C, 65.53; H, 6.39; N, 12.39; Found: C, 65.36; H, 6.71; N, 12.39.

EXAMPLE 61a

1-Methyl-3-[(1,4-cis)-4-(4-quinolin-5-ylpiperazin-1-yl)cyclohexyl]-1H-indole-5-carbonitrile To a solution of 5-piperazin-1-yl-quinoline (300 mg, 1.4 mmol), 4-(5-cyano-1-methyl-1H-indol-3-yl)-cyclohexanone (350 mg, 1.4 mmol), and sodium triacetoxyborohydride (450 mg, 2.1 mmol) in dichloroethane (40 mL) was added acetic acid (0.2 mL, 3.4 mmol) and stirred overnight at room temperature. The reaction was quenched with 1 M NaOH (25 mL) and $H_2O$ (100 mL) then extracted into $CH_2Cl_2$ (100 mL) and EtOAc (2×100 mL). The organic fractions were combined, dried over $Na_2SO_4$, concentrated, filtered and chromatographed (5% MeOH/EtOAc) affording 190 mg (30%) of the cis isomer as a white foam. The HCl salt was generated from EtOAc to give a white solid: mp decomposes above 235° C.

Elemental analysis for $C_{29}H_{31}N_5.HCl.0.5H_2O$; Calc'd: C, 70.36; H, 6.72; N, 14.15; Found: C, 70.43; H, 6.57; N, 13.83.

EXAMPLE 61b

1-Methyl-3-[(1,4-trans)-4-(4-quinolin-5-ylpiperazin-1-yl)cyclohexyl]-1H-indole-5-carbonitrile The trans isomer was isolated at the same time affording 140 mg (22%) as a pale yellow solid: mp discolors above 200° C.

Elemental analysis for $C_{29}H_{31}N_5.0.5H_2O$; Calc'd: C, 75.95; H, 7.03; N, 15.27; Found: C, 75.82; H, 6.72; N, 15.09.

EXAMPLE 62a

3–1(1,4-cis)-4-[4-(6-methoxy-1,2,3,4-tetrahydroquinolin-8-yl)piperazin-{-yl]cyclohexyl}-1-methyl-1H-indole-5-carbonitrile To a solution of 6-methoxy-5-piperazin-1-yl-1,2,3,4-tetrahydroquinoline (300 mg, 1.2 mmol), 4-(5-cyano-1-methyl-1H-indol-3-yl)-cyclohexanone (306 mg, 1.2 mmol), and sodium triacetoxyborohydride (254 mg, 1.8 mmol) in dichloroethane (50 mL) was added acetic acid (0.15 mL, 2.4 mmol) and stirred overnight at room temperature. The reaction was quenched with 1 M NaOH (50 mL) and H$_2$O (50 mL) then extracted in CH$_2$Cl$_2$ (100 mL) and EtOAc (2×100 mL). The organic fractions were combined, dried over Na$_2$SO$_4$, concentrated, filtered and chromatographed twice (5% MeOH/EtOAc) affording 140 mg (24%) of the cis isomer as a white foam. The HCl salt was generated from EtOAc to give a white solid: mp decomposes above 170° C.

Elemental analysis for C$_{30}$H$_{37}$N$_5$O.HCl.H$_2$O; Calc'd: C, 66.96; H, 7.49; N, 13.01; Found: C, 66.71; H, 7.28; N, 12.50.

EXAMPLE 62b

3-{(1,4-trans)-4-[4-(6-methoxy-1,2,3,4-tetrahydroquinolin-8-yl)piperazin-1-yl]cyclohexyl}-1-methyl-1H-indole-5-carbonitrile The trans isomer was isolated at the same time affording 80 mg (22%) as a white foam. The HCl salt was generated from EtOAc affording a white solid: mp decomposes above 225° C.

Elemental analysis for C$_{30}$H$_{37}$N$_5$O.HCl.0.5H$_2$O; Calc'd: C, 68.10; H, 7.43; N, 13.24; Found: C, 68.17; H, 7.30; N, 13.17.

EXAMPLE 63a

1-Methyl-3-[(1,4-cis)-4-(4-[1,6]naphthyridine-8-ylpiperazin-1-yl)cyclohexyl]-1H-indole-5-carbonitrile To a solution of 8-piperazin-1-yl-naphthyridine (470 mg, 2.19 mmol), 4-(5-cyano-1-methyl-1H-indol-3-yl)-cyclohexanone (550 mg, 2.19 mmol), and sodium triacetoxyborohydride (700 mg, 3.28 mmol) in dichloroethane (40 mL) was added acetic acid (0.25 mL, 4.38 mmol) and stirred overnight at room temperature. The reaction was quenched with 1 M NaOH (40 mL) and H$_2$O (20 mL) then extracted in CH$_2$Cl$_2$ (50 mL) and EtOAc (2×100 mL). The organic fractions were combined, dried over Na2SO$_4$, concentrated, filtered and chromatographed three times (5% MeOH/EtOAc) affording 490 mg (50%) of the cis isomer as a pale yellow solid: mp decomposes above 215° C., then melts 227–230° C.

Elemental analysis for C$_{28}$H$_{30}$N$_6$.0.5H$_2$O; Calc'd: C, 73.90; H, 6.76; N, 18.47; Found: C, 73.90; H, 6.76; N, 18.61.

EXAMPLE 63b

1-Methyl-3-[(1,4-trans)-4-(4-[1,6]naphthyridine-8-yl-piperazin-1-yl)cyclohexyl]-1H-indole-5-carbonitrile The trans isomer was isolated at the same time affording 120 mg (12%) as a pale yellow solid: mp decomposes above 195° C.

Elemental analysis for C$_{30}$H$_{37}$N$_5$O.0.5H$_2$O; Calc'd: C, 73.90; H, 6.76; N, 18.47; Found: C, 73.87; H, 6.75; N, 18.66.

EXAMPLE 64

1-Methyl-3-((1,4-cis)-4-{4-[6-(methylamino)quinolin-8-yl]piperazin-1-yl}cyclohexyl)-1H-indole-5-carbonitrile To a solution of 6-(methylamino)-8-piperazin-1-yl-quinoline (100 mg, 0.43 mmol), 4-(5-cyano-1-methyl-1H-indol-3-yl)-cyclohexanone (100 mg, 0.43 mmol), and sodium triacetoxyborohydride (130 mg, 0.62 mmol) in dichloroethane (30 mL) was added acetic acid (0.1 mL, 0.86 mmol) and stirred overnight at room temperature. The reaction was quenched with 1 M NaOH (50 mL) and H$_2$O (50 mL) then extracted in CH$_2$Cl$_2$ (100 mL) and EtOAc (2×100 mL). The organic fractions were combined, dried over Na$_2$SO$_4$, concentrated, filtered and chromatographed (10% MeOH/EtOAc) affording 60 mg (30%) of the cis isomer as a gold oil. The HCl salt was generated from EtOAc affording a yellow solid: mp decomposes above 170° C.

Elemental analysis for C$_{30}$H$_{34}$N$_6$.HCl.H$_2$O; Calc'd: C, 67.59; H, 7.00; N, 15.76; Found: C, 67.58; H, 6.86; N, 15.65.

EXAMPLE 65a (Cis)-3-{4-[4-(7-methoxyquinoxalin-5-yl)piperazin-1-yl]cyclohexyl}-1-methyl-1H-indole-5-carbonitrile To a solution of 7-methoxy-5-piperazin-1-yl-quinoxaline (160 mg, 0.66 mmol), 4-(5-cyano-1-methyl-1H-indol-3-yl)-cyclohexanone (170 mg, 0.66 mmol), and sodium triacetoxyborohydride (210 mg, 0.98 mmol) in dichloroethane (30 mL) was added acetic acid (0.1 mL, 1.3 mmol) and stirred overnight at room temperature. The reaction was quenched with 1 M NaOH (100 mL) then extracted in CH$_2$Cl$_2$ (75 mL) and EtOAc (100 mL). The organic fractions were combined, dried over Na$_2$SO$_4$, concentrated, filtered and chromatographed (5% MeOH/EtOAc) affording 120 mg (38%) of the cis isomer as a bright yellow solid: mp 226–229° C.

Elemental analysis for C$_{29}$H$_{32}$N$_6$O.H$_2$O; Calc'd: C, 69.86; H, 6.87; N, 16.85; Found: C, 69.94; H, 6.71; N, 16.60.

EXAMPLE 65b (Trans)-3-{4-[4-(7-methoxyquinoxalin-5-yl)piperazin-1-yl]cyclohexyl}-1-methyl-1H-indole-5-carbonitrile The trans isomer was isolated at the same time affording 80 mg (12%) as a yellow solid: mp 230–233° C.

Elemental analysis for C$_{29}$H$_{32}$N$_6$O.0.5H$_2$O; Calc'd: C, 71.14; H, 6.79; N, 17.16; Found: C, 71.29; H, 6.69; N, 17.16.

EXAMPLE 66a (Cis)-3-{4-[4-(6-methoxy[1,7]naphthyridin-8-yl)piperazin-1-yl]cyclohexyl}-1-methyl-1H-indole-5-carbonitrile To a solution of 6-methoxy-8-piperazin-1-yl-[1,7]naphthyridine (250 mg, 1.02 mmol), 4-(5-cyano-1-methyl-1H-indol-3-yl)-cyclohexanone (260 mg, 1.02 mmol), and sodium triacetoxyborohydride (320 mg, 1.53 mmol) in dichloroethane (50 mL) was added acetic acid (0.12 mL, 2.04 mmol) and stirred overnight at room temperature. The reaction was quenched with 1 M NaOH (50 mL) then extracted in CH$_2$Cl$_2$ (1×50 mL) and EtOAc (75 mL). The organic fractions were combined, dried over Na$_2$SO$_4$, concentrated, filtered and chromatographed (5% MeOH/EtOAc+NH$_4$OH) affording 160 mg (33%) of the cis isomer as a yellow foam. The HCl salt was generated form EtOAc affording a pale yellow solid: mp 235–238° C.

Elemental analysis for $C_{29}H_{32}N_6O.HCl.H_2O$; Calc'd: C, 65.10; H, 6.59; N, 15.71; Found: C, 65.09; H, 6.77; N, 15.60.

EXAMPLE 66b (Cis)-3-{4-[4-(6-methoxy[1,7]naphthyridin-8-yl) piperazin-1-yl]cyclohexyl}-1-methyl-1H-indole-5-carbonitrile The trans isomer was isolated at the same time affording 90 mg (18%) as a yellow foam. The HCl salt was generated from EtOAc affording a pale yellow solid: mp 230–233° C.

Elemental analysis for $C_{29}H_{32}N_6O.HCl.0.5H_2O$; Calc'd: C, 66.21; H, 6.51; N, 15.97; Found: C, 66.26; H, 6.37; N, 15.91.

EXAMPLE 67a

3-{(1,4-cis)4-[4-(2-Oxo-2,3-dihydro-1H-benzimidoazol-4-yl)-piperazin-1-yl]-cyclohexyl}-1H-indole-5-carbonitrile To a solution of 4-piperazin-1-yl-1,3-dihydro-benzoimidazol-2-one (400 mg, 1.8 mmol), 4-(5-cyano-1H-indol-3-yl)-cyclohexanone (430 mg, 1.8 mmol), and sodium triacetoxyborohydride (590 mg, 2.8 mmol) in dichloroethane (50 mL) was added acetic acid (0.21 mL, 3.7 mmol) and stirred overnight at room temperature. The reaction was quenched with 2.5 M NaOH (100 mL) then extracted in MeOH/CH$_2$Cl$_2$ (2×100 mL). The organic fractions were combined, dried over Na$_2$SO$_4$, concentrated, filtered and chromatographed two times (10% MeOH/EtOAc) affording 185 mg (23%) of the cis isomer as a beige solid. The HCl salt was generated form EtOAc affording an off-white solid: mp decomposes above 235° C.

Elemental analysis for $C_{26}H_{28}N_6O.HCl.1.5H_2O$; Calc'd: C, 61.96; H, 6.40; N, 16.67; Found: C, 61.97; H, 6.26; N, 16.28.

EXAMPLE 67b

3-{(1,4-trans)4-[4-(2-Oxo-2,3-dihydro-1H-benzimidoazol-4-yl)-piperazin-1-yl]-cyclohexyl3-1H-indole-5-carbonitrile The trans isomer was isolated at the same time affording 90 mg (18%) as a white solid. The HCl salt was generated from EtOAc affording a white solid: mp decomposes above 265° C.

Elemental analysis for $C_{26}H_{28}N_6O.HCl.1.5H_2O$; Calc'd: C, 61.96; H, 6.40; N, 16.67; Found: C, 61.98; H, 6.25; N, 16.38.

EXAMPLE 68a

3-[cis-4-[4-(6-Methoxy-1H-dinole-4-yl)-1-piperazinyl]cyclohexyl]1H-indole-5-carbonitrile A solution of 4-(5-cyano-1-methyl-3-indolyl)-cyclohexanone (0.43 g, 1.8 mmol), 6-methoxy-4-piperazin-1-yl-1H-indole (0.4 g, 1.8 mmol), sodium triacetoxyborohydride (0.77 g, 2.7 mmol) and acetic acid (0.21 mL, 3.6 mmol) in 1,2-dichloroethane (20 mL) was allowed to stir at room temperature overnight. The reaction was quenched with 1 N aqueous sodium hydroxide (10 mL), and extracted with methylene chloride (3×50 mL). The combined organic layers were washed with brine (2×50 mL), then dried over anhydrous sodium sulfate and filtered. Chromatography (5% methanol/ethyl acetate) afforded 0.38 g (48%) of the title compound as a white solid: mp 182–185° C.

The HCl salt was prepared in ethyl acetate: mp 225–226° C. Elemental analysis for $C_{28}H_{31}N_5O.2HCl.0.25H_2O.0.40C_4H_8O_2$; Calc'd: C, 62.79; H, 6.53; N, 12.37; Found: C, 62.28; H, 6.44; N, 12.97.

EXAMPLE 68b

3-[trans-4-[4-(6-Methoxy-1H-indole-4-yl)-1-piperazinyl]cyclohexyl]1H-indole-5-carbonitrile The trans compound was isolated at same time as the cis isomer in 33% yield (0.26 g) as a white solid: mp 157–160° C. The HCl salt was prepared in ethyl acetate: mp>210° C.

Elemental analysis for $C_{28}H_{31}N_5O.HCl.1.5H_2O$; Calc'd: C, 64.82; H, 6.58; N, 13.94; Found: C, 65.04; H, 6.82; N, 13.54.

EXAMPLE 69

5-Fluoro-3-{4-[4-(6-methoxy-naphthalen-2-yl)-piperazin-1-yl]-cyclohexyl}-1H-indole To 400 mg (1.66 mmol) of 1-(6-methoxy-naphthalen-2-yl)-piperazine in 40 mL of CH$_2$Cl$_2$ and 100 mg of glacial HOAc at 23° C. was added 384 mg (1.66 mmol) of 4-(5-fluoro-1H-indol-3-yl)-cyclohex-3-enone followed by 216 mg, (1.89 mmol) of Na(OAc)$_3$BH. After stirring at 23° C. for 12 hours, the reaction mixture was transferred to a separatory funnel and partitioned between water and CH$_2$Cl$_2$. The organics were washed with brine, dried over MgSO$_4$, and chromatographed on silica gel eluting with 20:1 EtOAc:2 M NH$_3$ in MeOH. The product fractions were pooled, stripped, and treated with 115 mg (1.3 mmol) of (CO$_2$H)$_2$ in absolute EtOH to give 640 mg (1.40 mmol, an 84% yield) of the oxalate salt of the title compound as a white crystalline solid. mp: 200–203° C.; MS (ES) m/z 458 (MH)$^+$.

Elemental Analysis for $C_{29}H_{32}FN_3O$; Calc'd.: C, 67.95; H, 6.25, N, 7.67. Found: C, 66.64; H, 6.71; N, 7.11.

EXAMPLE 70a

3-[4-[(Cis)-4-(6-[1,3]dioxolan-2-yl-quinolin-8-yl)-piperazin-1-yl]-cyclohexyl-1H-indole-5-carbonitrile 6-[1,3]Dioxolan-2-yl-8-piperazinyl-quinoline 1.36 g (4.8 mmol) was combined with 1-methyl-3-(4-oxo-cyclohexyl)-1H-indole-5-carbonitrile, 1.53 g (7.2 mmol), 0.43 g (7.2 mmol) CH$_3$CO$_2$H, and 100 mL CH$_2$Cl$_2$ by the process described for Example 1. The crude was chromatographed on silica gel in a gradient of CH$_2$Cl$_2$ to 10:1 CH$_2$Cl$_2$:MeOH, and the cis compound was isolated, (R$_f$=0.39, 10:1 CH$_2$Cl$_2$:MeOH). The product fractions were pooled, stripped, and treated with 0.09 g (1.0 mmol) (CO$_2$H)$_2$ in absolute EtOH to give 1.0 g (1.9 mmol, a 40% yield) of the oxalate salt of the cis isomer of the title compound as a yellow crystalline solid. mp: 105° C.; MS (ES) m/z 522 (MH)$^+$.

Elemental Analysis for $C_{32}H_{35}N_5O_2$; Calc'd.: C, 73.68; H, 6.76, N, 13.43. Found: C, 73.67; H, 6.82; N, 13.23.

EXAMPLE 70b

3-[4-[(Trans)-4-(6-[1,3]dioxolan-2-yl-quinolin-8-yl)-piperazirn-1-yl]-cyclohexyl-1H-indole-5-carbonitrile The trans compound was also obtained, (R$_f$=0.24, 10:1 CH$_2$Cl$_2$:MeOH). The product fractions were pooled, stripped, and treated with 0.07 g (0.8 mmol) of $(CO_2H)_2$ in absolute EtOH to give 0.80 g (1.5 mmol, a 31% yield) mp: 160° C.; MS ES m/z 522 (MH)$^+$.

Elemental Analysis for $C_{32}H_{35}N_5O_2$; Calc'd.: C, 73.68; H, 6.76, N, 13.43. Found: C, 67.05; H, 6.27; N, 12.03.

EXAMPLE 71

8-[4-[(Cis)-4-(5-Cyano-1-methyl-1H-indole-3-yl)- cyclohexyl]-piperazin-1-yl]-6-quinolinecarbaldehyde To 920 mg (1.8 mmol) of 3-[4-[(cis)-4-(6-[1,3]dioxolan-2-yl-quinolin-8-yl)-piperazinyl]cyclohexyl-1H-indole-5-carbonitrile in 7 mL of THF and 14 mL of glacial HOAc at 23° C. was added 0.8 ml of 6N HCl. The reaction was heated at 40° C. for 5 hours. The volatiles were removed by rotary evaporation and the aqueous was neutralized with 5 N NaOH. The organics were extracted into $CH_2CH_2$ and washed with brine, dried over $MgSO_4$, and chromatographed on silica gel eluting with 10:1 $CH_2CH_2$: MeOH. ). The product fractions were pooled, stripped, and treated with 147 mg (1.6 mmol) $(CO_2H)_2$ in absolute EtOH to give 780 mg (1.3 mmol, a 72% yield) oxalate salt of the title compound as a pale yellow crystalline solid. mp: 172–174° C.; MS (ES) m/z 478 (MH)$^+$.

Elemental Analysis for $C_{30}H_{31}N_5O$; Calc'd.: C, 75.44; H, 6.54, N, 14.66. Found: C, 73.27; H, 6.66; N, 13.98.

EXAMPLE 72

8-[4-[(Trans)-4-(5-Cyano-1-methyl-1H-indole-3-yl)- cyclohexyl]-piperazin-1-yl]-6-quinolinecarbaldehyde The trans compound was obtained by the process described for Example 4 by combining 0.750 mg (1.4 mmol) 3-[4-[(trans)-4-(6-[1,3]dioxolan-2-yl-quinolin-8-yl)- piperazinyl]cyclohexyl-1H-indole-5-carbonitrile, 0.6 ml 6N HCl, 7 ml THF, 7 ml glacial HOAc. The product fractions were pooled, striped, and treated with 85 mg (0.9 mmol) $(CO_2H)_2$ in absolute EtOH to give 450 mg (.76 mmol, a 42% yield) Mp: 201–203° C.; MS (ES m/z 478 (MH)$^+$.

Elemental Analysis for $C_{30}H_{31}N_5O$; Calc'd.: C, 75.44; H, 6.54, N, 14.66. Found: C, 72.10; H, 6.80; N, 12.64.

EXAMPLE 73

8-[4-[(Cis)-4-(5-cyano-1-methyl-1H-indole-3-yl) cyclohexyl]-1-piperazinyl]-6-quinolinecarboxylic acid To 750 mg (1.6 mmol) of 8-[4-[(Cis)-4-(5-cyano-1-methyl-1H-indole-3-yl)cyclohexyl]-1-piperazinyl]-6-quinolinecarbaldehyde in 60 mL of t-BuOH and 8 mL of $CH_3CHC(CH_3)_2$ at 23° C. was added a solution of 1.3 mg (14.4 mmol) $NaClO_2$, 1.3 g (10.8 mmol) $NaH_2PO_4$ in 3 ml water. After stirring at 23° C. for 12 hours, the volatiles were removed by rotary evaporation. The reaction mixture was transferred to a separatory funnel and partitioned between water and $CH_2Cl_2$. The organics were washed with brine, dried over $MsSO_4$, and chromatographed on silica gel eluting with 20:1 $CH_2Cl_2$:MeOH containing 5% glacial HOAc. The product fractions were pooled, stripped, and treated with 75 mg (0.83 mmol) of $(CO_2H)_2$ in absolute EtOH to give 390 mg (0.6 mmol, a 38% yield) of the oxalate salt of the title compound as a tan crystalline solid. mp: 230° C.; MS (ES) m/z: 494 (MH)$^+$.

Elemental Analysis for $C_{30}H_{31}N_5O_2$; Calc'd.: C, 73.00; H, 6.33, N, 14.19. Found: C, 50.91; H, 4.92; N, 7.70.

EXAMPLE 74

8-[4-[(Trans)-4-(5-cyano-1-methyl-1H-indole-3-yl) cyclohexyl]-1-piperazinyl]-6-quinolinecarboxylic acid The trans was obtained by the process described for Example 73 by combining 0.30 g (.60 mmol) 8-[4-[(Trans)-4-(5-cyano-1-methyl-1H-indole-3-yl)cyclohexyl]-1-piperazinyl]-6-quinolinecarbaldehyde, 0.48 g (5.5 mmol) $NaClO_2$, 0.48 g (4.1mmol) $NaH_2PO_4$, 24 mL t-BuOH, 3 mL$CH_3CHC(CH_3)_2$, and 6 ml water. The product fractions were pooled, striped, and treated with 54 mg (0.60 mmol) of $(CO_2H)_2$ in absolute EtOH to give 97 mg (.16 mmol, a 10% yield) mp: 275° C. MS (ES) m/z: 494 (MH)$^+$.

Elemental Analysis for $C_{30}H_{31}N_5O$; Calc'd.: C, 75.44; H, 6.54, N, 14.66. Found: C, 50.42; H, 4.66; N, 8.82.

EXAMPLE 75

Methyl 8-[4-[(Cis)-4-(5-cyano-1-methyl-1H-indol-3-yl)cyclohexyl]-1-piperazinyl]-6-quinolinecarboxylate To 50 mg (0.1 mmol) of 8-[4-[(Cis)-4-(5-cyano-1-methyl-1H-indole-3-yl)cyclohexyl]-1-piperazinyl]-6-quinolinecarboxylic acid in 1 mL of MeOH and 3 mL of $C_6H_5CH_3$ at 23° C. was added 0.9 mL (0.39 mmol) of a 10% solution of $(CH_3)_3SiCHN_2$ in hexanes. After stirring at 23° C. for 12 hours, the volatiles were removed by rotary evaporation. The crude product was chromatographed on silica gel eluting with 20:1 $CH_2Cl_2$:MeOH. The product fractions were pooled, stripped, and treated with 5 mg (0.05 mmol) of $(CO_2H)_2$ in absolute EtOH to give 20 mg (0.04 mmol, a 40% yield) of the oxalate salt of the title compound as a tan crystalline solid. mp: 153–155° C.; MS (ES) m/z: 599 (MH)$^+$.

Elemental Analysis for $C_{31}H_{33}N_5O_2$; Calc'd.: C, 66.28; H, 5.90, N, 11.71. Found: C, 61.49; H, 5.85; N, 10.35.

EXAMPLE 76a

3-[4-[(Cis)-4-(7-methoxy-8-quinolinyl)-1- piperazinyl]cyclohexyl]-1-methyl-1H-indole-5- carbonitrile 7-Methoxy-8-(1-piperazinyl)quinoline 400 mg (1.6 mmol) was combined with 404 mg (1.6 mmol) of 1-methyl-3-(4-oxo-cyclohexyl)-1H-indole-5-carbonirile, 510 mg (2.4 mmol) of $Na(OAc)_3BH$, 143 mg (2.4 mmol) of glacial HOAc, in 30 mL $CH_2Cl_2$ by the process described for Example 69. The crude was chromatographed on silica gel eluting with 20:1 $CH_2Cl_2$:MeOH, the cis compound was isolated ($R_f$=0.34, 10:1 EtOAc:MeOH). The product fractions were pooled, stripped, and treated with 27 mg (0.30 mmol) of $(CO_2H)_2$ in absolute EtOH to give 179 mg (0.37 mmol, a 23% yield) of the oxalate salt of the title compound as a yellow crystalline solid. mp: 183–186° C.; MS (ES) m/z: 480 (MH)$^+$.

Elemental Analysis for $C_{30}H_{33}N_5O$; Calc'd.: C, 67.43; H, 6.19, N, 12.29. Found: C, 65.38; H, 6.34; N, 11.83.

EXAMPLE 76b

3-[4-[(Trans)-4-(7-methoxy-8-quinolinyl)-1- piperazinyl]cyclohexyl]-1-methyl-1H-indole-5- carbonitrile The trans compound was obtained at the same time ($R_f$=0.17, 10:1 EtOAc:MeOH). The product fractions were pooled, stripped, and treated with 12 mg (0.13 mmol) of $(CO_2H)_2$ in absolute EtOH to give 80 mg (.17 mmol, an 11% yield) mp: 144–148° C.; MS (ES) m/z: 480 (MH)$^+$.

Elemental Analysis for $C_{30}H_{33}N_5O$; Calc'd.: C, 67.43; H, 6.19, N, 12.29. Found: C, 64.17; H, 6.37; N, 11.68.

EXAMPLE 77a

8-[4-[(Cis)-4-(5-cyano-1-methyl-1H-indol-3-yl) cyclohexyl]-1-piperazinyl]-N,N-dimethyl-6-quinolincarboxamide N,N-dimethyl-8-(1-piperazinyl)-6-quinolinecarboxamide 300 mg (1.1 mmol) was combined with 267 mg (1.1 mmol) of 1-methyl-3-(4-oxo-cyclohexyl)-1H-indole-5-carbonirile, 339 mg (1.6 mmol) of $Na(OAc)_3BH$, 96 mg (1.6 mmol) of glacial HOAc in 20 mL $CH_2Cl_2$ by the process described for Example 69. The crude product was chromatographed on silica gel with a gradient of EtOAc to 10:1 EtOAc:MeOH, and the cis compound was isolated ($R_f$=0.43, 10:1 EtOAc:2 M $NH_3$ in MeOH). The product fractions were pooled, striped, and treated with 35 mg (0.39 mmol) of $(CO_2H)_2$ in absolute EtOH to give 210 mg (0.40 mmol, a 36% yield) of the oxalate salt of the title compound as a pale yellow crystalline solid. mp: 163–165° C.; MS (ES) m/z: 521 (MH)$^+$.

Elemental Analysis for $C_{32}H_{36}N_6O$; Calc'd.: C, 66.83; H, 6.27, N, 13.75. Found: C, 59.62; H, 6.15; N, 11.33.

EXAMPLE 77b

8-[4-[(Trans)-4-(5-cyano-1-methyl-1H-indol-3-yl) cyclohexyl]-1-piperazinyl]-N,N-dimethyl-6-quinolincarboxamide The trans compound was obtained at the same time, ($R_f$=0.33, 10:1 EtOAc:2M $NH_3$ in MeOH). The product fractions were pooled, striped, and treated with 15 mg (0.17 mmol) of $(CO_2H)_2$ in absolute EtOH to give 80 mg (0.15 mmol, a 14% yield) mp: 160–163° C.; MS (ES) m/z: 521 (MH)$^+$.

Elemental Analysis for $C_{32}H_{36}N_6O$; Calc'd.: C, 66.83; H, 6.27, N, 13.75. Found: C, 62.7; H, 6.52; N, 12.33.

EXAMPLE 78

6-Methoxy-8-{cis-4-[4-(1H-pyrrolo[2,3-b]pyridin-3-yl)cyclohexyl]-1-piperazinyl}quinoline To a stirred solution of 195 mg (0.80 mmol) of 6-methoxy-8-(1-piperazinyl)quinoline in 10 mL of 1,2-dichloroethane at 23° C. was added 177.9 mg (0.83 mmol) of 4-(1H-pyrrolo[2,3-b]pyridin-3-yl)cyclohexanone, 254 mg (1.2 mmol) of sodium triacetoxyborohydride, and 78 mg (1.3 mmol) of glacial acetic acid. The reaction was monitored by TLC on a silica gel plate eluted with $CH_2CH_2$/MeOH (10:1). After stirring at 23° C. for 64 hours, the reaction was quenched with 10 mL of 1 N NaOH, and extracted with $CH_2Cl_2$ (2×25 mL). The aqueous layer was adjusted to pH 10 with AcOH, and further extracted with $CH_2Cl_2$ (2×75 mL). The combined organic layers were washed with brine (2×75 mL), dried over $MgSO_4$, filtered, and evaporated to a tan solid.

The crude product was purified by flash chromatography on silica gel using a gradient elution of $CH_2CH_2$/MeOH (40:1 to 10:1 to 4:1). The appropriate fractions were combined and evaporated to afford 94.8 mg (0.21 mmol, a 27% yield) of the title compound as a tan crystalline solid.

The oxalate salt of the title compound was prepared by adding 19 mg (0.21 mmol) of oxalic acid to 92 mg (0.21 mmol) of the title compound in 1 mL of ethanol at 23° C. After stirring at 23° C. for 64 hours, a solid precipitated out of solution. Diethyl ether (5 mL) was added to the suspension and cooled to 0° C., to further crystallize the product. The precipitated solid was collected and washed with ether to afford 79.5 mg (15 mmol, a 71% yield) of the oxalate salt. mp: 216–220° C.; MS (ES) m/z: 442.3 (MH)$^+$, 221.6 (M/2+H)$^+$.

Elemental Analysis For $C_{29}H_{33}N_5O_5$; Calc'd.: C, 65.48; H, 6.25; N, 13.17. Found: C, 62.66; H, 5.95; N, 11.67.

EXAMPLE 79

6-Methoxy-8-{cis-4-[4-(1-methyl-1H-pyrrolo[2,3-b]pyridin-3-yl)cyclohexyl]-1-piperazinyl}quinoline The title compound was prepared by the procedure described in Example 78 using 4-(1-methyl-1H-pyrrolo[2,3-b]pyridin-3-yl)-cyclohexanone (204.7 mg, 0.89 mmol) in place of 4-(1H-pyrrolo[2,3-b]pyridin-3-yl)cyclohexanone. Yield: 30% (108.5 mg, 0.24 mmol); viscous yellow oil.

The oxalate salt was prepared in the manner previously described in Example 78 using 108.5 mg (0.24 mmol) of the title compound. Yield: 30% (39.2 mg, 0.072 mmol). mp: 105–110° C.; MS (ES) m/z: 456.3 (MH)$^+$, 228.8 (M/2 +H)$^+$.

Elemental Analysis for $C_{30}H_{35}N_5O_5$; Calc'd.: C, 66.00; H, 6.46; N, 12.83. Found: C, 58.43; H, 6.31; N, 10.57.

EXAMPLE 80

8-{Cis-4-[4-(6-fluoro-1H-indol-3-yl)cyclohexyl]-1-piperazinyl}-6-methoxyquinoline The title compound was prepared by the procedure described in Example 78 using 4-(6-fluoro-1H-indol-3-yl)-cyclohexanone (401 mg, 1.87 mmol) in place of 4-(1H-pyrrolo[2,3-b]pyridin-3-yl)cyclohexanone. Yield: 28% (243 mg, 0.53 mmol); white crystalline solid.

The oxalate salt was prepared in the manner previously described in Example 78 using 78.0 mg (0.24 mmol) of the title compound. Yield: 66% (61.1 mg, 0.11 mmol) as a white solid. mp: 239–243° C.; MS (ES) m/z: 459.3 (MH)$^+$, 230.1 (M/2+H).

Elemental Analysis for $C_{30}H_{33}FN_4O_5$; Calc'd.: C, 65.64; H, 6.06; N, 10.21. Found: C,65.16; H,6.40; N, 9.86.

EXAMPLE 81

8-{Cis-4-[4-(6-fluoro-1-methyl-1H-indol-3-yl) cyclohexyl]-1-piperazinyl}-6-methoxyquinoline The title compound was prepared by the procedure described in Example 78 using 4-(6-fluoro-1-methyl-1H-indol-3-yl)-cyclohexanone (230 mg, 0.94 mmol) in place of 4-(1H-pyrrolo[2,3-b]pyridin-3-yl)cyclohexanone. Yield: 30% (131.6 mg, 0.28 mmol); white crystalline solid.

The oxalate salt was prepared in the manner previously described in Example 78 using 127.9 mg (0.27 mmol) of the title compound. Yield: 20% (30.1 mg, 0.054 mmol). mp: 219–223° C.; MS (ES) m/z: 473.2 (MH)$^+$.

Elemental Analysis for $C_{31}H_{35}FN_4O_5$; Calc'd.: C, 66.14; H, 6.27; N, 9.95. Found: C, 66.26; H, 6.16; N, 7.49.

EXAMPLE 82

6-Methoxy-8-(4-{(cis)-4-[5-(trifluoromethyl)-1H-indol-3-yl]cyclohexyl}-1-piperazinyl)quinoline The title compound was prepared by the procedure described in Example 78 using cyclohexanone 4-(5- trifluoromethyl-1H-indol-3-yl)-cyclohexanone (271.5 mg, 0.97 mmol) in place of 4-(1H-pyrrolo[2,3-b]pyridin-3-yl) cyclohexanone. Yield: 12% (57 mg, 0.12 mmol); off-white solid.

The oxalate salt was prepared in the manner previously described in Example 78 using 25.6 mg (0.050 mmol) of the title compound. Yield: 67% (20 mg, 0.033 mmol). mp: 143–147° C.; MS (ES) m/z: 509.4 (MH)$^+$.

Elemental Analysis for $C_{31}H_{33}F_3N_4O_5$; Calc'd.: C, 62.17; H, 5.55; N, 9.35. Found: C, 57.55; H, 5.84; N, 8.63.

EXAMPLE 83a (Cis)-6-methoxy-8-(4-{4-[1-methyl-5-(trifluoromethyl)-1H-indol-3-yl] cyclohexyl}piperazinyl)quinoline The title compound was prepared by the procedure described in Example 78 using 4-(1-methyl-5-trifluoromethyl-1H-indol-3-yl)-cyclohexanone (750.3 mg, 2.54 mmol) in place of 4-(1H-pyrrolo[2,3-b]pyridin-3-yl) cyclohexanone. Flash chromatography was performed using a gradient elution of ethyl acetate/MeOH (40:1 to 10:1 to 4:1) in place of $CH_2Cl_2$/MeOH; $R_f$=0.36. Yield: 12% (162.1 mg, 0.30 mmol); tan solid.

The oxalate salt was prepared in the manner previously described in Example 78 using 93.5 mg (0.18 mmol) of the title compound. Yield: 29% (31.4 mg, 0.051 mmol). mp: 101–104° C.; MS (ES) m/z: 523.2 (MH)$^+$.

Elemental Analysis for $C_{32}H_{35}F_3N_4O_5$; Calc'd.: C, 62.70; H, 5.76; N, 9.14. Found: C, 55.43; H, 6.21; N, 7.75.

EXAMPLE 83b (Trans)-6-methoxy-8-(4-{4-[1-methyl-5-(trifluoromethyl)-1H-indol-3-yl] cyclohexyl}piperazinyl)quinoline The trans compound ($R_f$=0.26) was isolated at the same time as the cis isomer in 11% yield (140 mg, 0.27 mmol) as a tan solid. The oxalate salt was prepared in the manner previously described in Example 78 using 100 mg (0.19 mmol) of the title compound. Yield: 86% (101 mg, 0.16 mmol). mp: 111–115° C.; MS (ES) m/z: 523.3 (MH)$^+$.

Elemental Analysis for $C_{32}H_{35}F_3N_4O_5$; Calc'd.: C, 62.70; H, 5.76; N, 9.14. Found: C, 59.47; H, 5.80; N, 7.93.

EXAMPLE 84

3-{(Cis)-4-[4-(6-methoxy-8-quinolinyl)-1-piperazinyl]cyclohexyl}-1-methyl-1H-carbonitrile The title compound was prepared in a similar manner described in Example 781 using 1-methyl-3-(4-oxo-cyclohexyl)-1H-indole-6-carbonitrile (164 mg, 0.69 mmol) in place of 4-(1H-pyrrolo[2,3-b]pyridin-3-yl) cyclohexanone. Flash chromotography was performed using a gradient elution of ethyl acetate/MeOH (40:1 to 10:1 to 4:1) in place of $CH_2CH_2$/MeOH. Yield: 20% (80.4 mg, 0.17 mmol); yellow solid.

The oxalate salt was prepared in the manner previously described in Example 78 using 80.4 mg (0.17 mmol) of the title compound and DMF in place of EtOH. Yield: 56% (53.4 mg, 0.094 mmol). mp: 111–114° C.; MS (ES) m/z: 480.2 (MH)$^+$, 240.7 (M/2 +H)$^+$.

Elemental Analysis for $C_{32}H_{35}N_5O_5$; Calc'd.: C, 67.43; H, 6.19; N, 12.29. Found: C, 62.99; H, 5.98; N, 11.16.

EXAMPLE 85

3-{4-[4-(6-Methoxy-8-quinolinyl)-1-piperazinyl] cyclohexyl}-1H-indole-6-carbonitrile The title compound was prepared by the procedure described in Example 78 using 3-(4-oxo-cyclohexyl)-1H-indole-6-carbonitrile (404.8 mg, 1.7 mmol) in place of 4-(1H-pyrrolo[2,3-b]pyridin-3-yl)cyclohexanone. Flash chromatography was performed using a gradient elution of ethyl acetate/MeOH (40:1 to 10:1 to 4:1) in place of $CH_2CH_2$/MeOH. Yield: 63% (493.7 mg, 1.06 mmol); tan solid.

The oxalate salt was prepared in the manner previously described in Example 78 using 183.5 mg (0.39 mmol) of title compound and DMF in place of EtOH. Yield: 43% (93 mg, 0.20 mmol). mp: 242–244° C.; MS (ES) m/z: 466.2 (MH)$^+$.

Elemental Analysis for $C_{31}H_{33}N_5O_5$; Calc'd.: C, 66.97; H, 5.98; N, 12.60. Found: C, 67.56; H, 6.09; N, 13.15.

EXAMPLE 86a

8-{4-[(1,4-cis)-4-(5-Fluoro-1-methyl-1H-indol-3-yl)-cyclohexyl]-piperazin-1-'yl}-6-methoxy-quinoline To a solution of 0.270 g of 6-Methoxy, 8-piperazino-quinoline in 20 mL of $CH_2Cl_2$, was added 0.245 g of 4-(5-fluoro-1-methyl-1H-3-indolyl)-cyclohexanone followed by 0.530 g of sodium triacetoxyborohydride and 0.09 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 75 mL of silica gel using 50% ethyl acetate/hexanes, 75% ethyl acetate/hexanes, and finally 100% ethyl acetate to give 0.115 g of the desired product: mp 216–218° C.; MS (ES) m/z (relative intensity): 473 (M++H, 100).

EXAMPLE 86b

8-{4-[(1,4-trans)-4-(5-Fluoro-1-methyl-1H-indol-3-yl)-cyclohexyl]-piperazin-1-'yl}-6-methoxy-quinoline The trans isomer was isolated at the same time as the cis isomer as an off white solid (0.013020 g).mp 198–200° C. MS (ES) m/z (relative intensity): 473 (M$^+$+H, 100).

EXAMPLE 87a

8-{4-[4-((1,4-cis)-1H-Indol-3-yl)-cyclohexyl]-piperazin-1-yl}-6-methoxy-quinoline To a solution of 0.350 g of 6-Methoxy, 8-piperazino-quinoline in 10 mL of $CH_2Cl_2$, was added 0.335 g of 4-(1-H-3-indolyl)-cyclohexanone followed by 0.840 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 125 mL of silica gel using 50% ethyl acetate/hexanes, 75% ethyl acetate/hexanes, and finally 100% ethyl acetate to give 0.041 g of the desired product: mp 165–171° C.; MS (ES) m/z (relative intensity): 441 (M$^+$+H, 100).

EXAMPLE 87b

8-{4-[4-((1,4-trans)-1H-Indol-3-yl)-cyclohexyl]-piperazin-1-yl}-6-methoxy-quinoline The trans isomer was isolated at the same time as the cis isomer as an off white solid (0.023 g).mp 118–122° C. MS (ES) m/z (relative intensity): 441 (M$^+$+H, 100).

EXAMPLE 88a

3-{(1,4-cis)-4-[4-(6-Methoxy-quinolin-8-yl)-piperazin-1-yl]-cyclohexyl}-1-methyl-1H-indole-5-carbonitrile To a solution of 0.243 g of 6-Methoxy, 8-piperazino-quinoline in 10 mL of $CH_2Cl_2$, was added 0.252 g of 3-(4-oxo-cyclohexyl)-1-methyl-1H-indole-5-carbo-nitrile followed by 0.527 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.085 g of the desired product: mp 239–240° C.; MS (ES) m/z (relative intensity): 480 ($M^+$+H, 100).

EXAMPLE 88b

3-{(1,4-trans)-4-[4-(6-Methoxy-quinolin-8-yl)-piperazin-1-yl]-cyclohexyl}-1-methyl-1H-indole-5-carbonitrile The trans isomer was isolated at the same time as the cis isomer as an off white solid (0.029 g).mp 225–228° C. MS (ES) m/z (relative intensity): 480 ($M^+$+H, 100).

EXAMPLE 89a

6-Methoxy-8-{4(1,4-cis)-[4-(1-methyl-1H-indol-3-yl)-cyclohexyl]-piperazin-1-'yl}-quinoline To a solution of 0.243 g of 6-Methoxy, 8-piperazino-quinoline in 10 mL of $CH_2Cl_2$, was added 0.250 g of 4-(1-methyl-1-H-3-indolyl)-cyclohexanone followed by 0.527 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.120 g of the desired product: mp 190–191° C.; MS (ES) m/z (relative intensity): 455 ($M^+$+H, 100).

EXAMPLE 89b

6-Methoxy-8-{4-(1,4-trans)[4-(1-methyl-1H-indol-3-yl)-cyclohexyl]-piperazin-1-'yl}-quinoline The trans isomer was isolated at the same time as the cis isomer as an off white solid (0.027 g).mp 208–210° C. MS (ES) m/z (relative intensity): 455 ($M^+$+H, 100).

EXAMPLE 90a

8-{4-(1,4-cis)[4-(5-Fluoro-1-methyl-1H-indol-3-yl)-cyclohexyl]-piperazin-1-'yl}-6-methyl-quinoline To a solution of 0.275 g of 6-Methyl, 8-piperazino-quinoline in 10 mL of $CH_2Cl_2$, was added 0.326 g of 4-(5-fluoro-1-methyl-3-indolyl)-cyclohexanone followed by 0.639 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 75 mL of silica gel using 50% ethyl acetate/hexanes, 75% ethyl acetate/hexanes, and finally 100% ethyl acetate to give 0.145 g of the desired product: mp 179–181° C.; MS (ES) m/z (relative intensity): 457 ($M^+$+H, 100).

EXAMPLE 90b

8-{4-(1,4-trans)[4-(5-Fluoro-1-methyl-1H-indol-3-yl)-cyclohexyl]-piperazin-1-'yl}-6-methyl-quinoline The trans isomer was isolated at the same time as the cis isomer as an off white solid (0.043 g).mp 98–103° C. MS (ES) m/z (relative intensity): 457 ($M^+$+H, 100).

EXAMPLE 91a

8-{(1,4-cis)-4-[4-(5-cyano-1H-indol-3-yl)-cyclohexyl]-piperazin-1-yl}-6-methyl-quinoline To a solution of 0.300 g of 6-Methyl, 8-piperazino-quinoline in 10 mL of $CH_2Cl_2$, was added 0.280 g of 4-(1-H-3-indolyl)-cyclohexanone followed by 0.700 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.125 g of the desired product: mp 132–135° C.; MS (ES) m/z (relative intensity): 425 ($M^+$+H, 100).

EXAMPLE 91b

8-{(1,4-cis)-4-[4-(5-cyano-1H-indol-3-yl)-cyclohexyl]-piperazin-1-yl}-6-methyl-quinoline To a solution of 0.275 g of 6-Methyl, 8-piperazino-quinoline in 10 mL of $CH_2Cl_2$, was added 0.315 g of 3-(4-oxo-cyclohexyl)-1H-indole-5-carbonitrile followed by 0.639 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.175 g of the desired product: mp 142–147° C.; MS (ES) m/z (relative intensity): 450 ($M^+$+H, 100).

EXAMPLE 92

8-{(1,4-cis)-4-[4-(1-ethyl-5 -Fluoro-1H-indol-3-yl)-cyclohexyl]-piperazin-1-yl}-6-methoxy-quinoline To a solution of 0.400 g of 6-Methoxy, 8-piperazino-quinoline in 20 mL of $CH_2Cl_2$, was added 0.300 g of 4-(5-fluoro-1-ethyl-3-indolyl)-cyclohexanone followed by 0.651 g of sodium triacetoxyborohydride and 0.4 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.041 g of the desired product: mp 203–205° C.; MS (ES) m/z (relative intensity): 487 ($M^+$+H, 100).

EXAMPLE 93a

8-{(1,4-cis)-4-[4-(5-methoxy-1-methyl-1H-indol-3-yl)-cyclohexyl]-piperazin-1-yl}-6-methoxy-quinoline To a solution of 0.500 g of 6-Methoxy, 8-piperazino-quinoline in 20 mL of $CH_2Cl_2$, was added 0.565 g of 4-(5-methoxy-1-methyl-3-indolyl)-cyclohexanone followed by 1.1 g of sodium triacetoxyborohydride and 0.4 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 200 mL of silica gel using 50% ethyl acetate/hexanes, 75% ethyl acetate/hexanes, and finally 100% ethyl acetate to give 0.077 g of the desired product: mp 170–172° C.; MS (ES) m/z (relative intensity): 485 (M$^+$+H, 100).

EXAMPLE 93b

8-{(1,4-trans)-4-[4-(5-methoxy-1H-indol-3-yl)-cyclohexyl]-piperazin-1-yl}-6-methoxy-quinoline The trans isomer was isolated at the same time as the cis isomer as an off white solid (0.039 g).mp 185–186° C. MS (ES) m/z (relative intensity): 485 (M$^+$+H, 100).

EXAMPLE 94a

3-{(1,4-cis)-4-[4-(6-isopropoxy-quinolin-8-yl)-piperazin-1-yl]-cyclohexyl}-1-methyl-1H-indole-5-carbonitrile To a solution of 0.350 g of 6-Isopropoxy, 8-piperazino-quinoline in 10 mL of CH$_2$Cl$_2$, was added 0.356 g of 3-(4-oxo-cyclohexyl)-1-methyl-1H-indole-5-carbonitrile followed by 0.405 g of sodium triacetoxyborohydride and 0.08 mL acetic acid. The reaction was stirred at room temperature overnight. It was quenched with 1N NaOH, and the product was extracted with CH$_2$Cl$_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.141 g of the desired product: mp 223–226° C.; MS (ES) m/z (relative intensity): 508 (M$^+$+H, 100).

EXAMPLE 94b

3-{(1,4-trans)-4-[4-(6-isopropoxy-quinolin-8-yl)-piperazin-1-yl]-cyclohexyl}-1-methyl-1H-indole-5-carbonitrile The trans isomer was isolated at the same time as the cis isomer as an off white solid (0.087 g).mp 221–223° C. MS (ES) m/z (relative intensity): 508 (M$^+$+H, 100).

EXAMPLE 95a

3-{(1,4-cis)-4-[4-(6-fluoro-quinolin-8-yl)-piperazin-1-yl]-cyclohexyl}-1-methyl-i1H-indole-5-carbonitrile To a solution of 0.300 g of 6-Fluoro, 8-piperazino-quinoline in 10 mL of CH$_2$Cl$_2$, was added 0.411 g of 3-(4-oxo-cyclohexyl)-1-methyl-1H-indole-5-carbonitrile followed by 0.359 g of sodium triacetoxyborohydride and 0.1 mL acetic acid. The reaction was stirred at room temperature overnight. It was quenched with 1N NaOH, and the product was extracted with CH$_2$Cl$_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.187 g of the desired product: mp 230° C.; MS (ES) m/z (relative intensity): 468 (M$^+$+H, 100).

EXAMPLE 95b

3-{(1,4-trans)-4-[4-(6-fluoro-quinolin-8-yl)-piperazin-1-yl]-cyclohexyl}-1-methyl-1H-indole-5-carbonitrile The trans isomer was isolated at the same time as the cis isomer as an off white solid (0.039 g).mp 214–216° C. MS (ES) m/z (relative intensity): 468 (M$^+$+H, 100).

EXAMPLE 96a

3-{(1,4-cis)-4-[4-(6-trifluoromethoxy-quinolin-8-yl)-piperazin-1-yl]-cyclohexyl}-1-methyl-1H-indole-5-carbonitrile To a solution of 0.297 g of 6-Trifluoromethoxy, 8-piperazino-quinoline in 10 mL of DCE was added 0.272 g of 3-(4-oxo-cyclohexyl)-1-methyl-1H-indole-5-carbonitrile followed by 0.316 g of sodium triacetoxyborohydride and 0.1 mL acetic acid. The reaction was stirred at room temperature overnight. It was quenched with 1N NaOH, and the product was extracted with CH$_2$Cl$_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.166 g of the desired product: mp 206° C.; MS (ES) m/z (relative intensity): 534 (M$^+$+H, 100).

EXAMPLE 96b

3-{(1,4-trans)-4-[4-(6-trifluoromethoxy-quinolin-8-yl)-piperazin-1-yl]-cyclohexyl}-1-methyl-1H-indole-5-carbonitrile The trans isomer was isolated at the same time as the cis isomer as an off white solid (0.064 g).mp 170° C. MS (ES) m/z (relative intensity): 534 (M$^+$+H, 100).

EXAMPLE 97a

3-{(1,4-cis)-4-[4-(5-methoxy-quinolin-8-yl)-piperazin-1-yl]-cyclohexyl}-1-methyl-1H-indole-5-carbonitrile To a solution of 0.500 g of 5-Methoxy, 8-piperazino-quinoline in 10 mL of DCE, was added 0.544 g of 3-(4-oxo-cyclohexyl)-1-methyl-1H-indole-5-carbonitrile followed by 0.633 g of sodium triacetoxyborohydride and 0.2 mL acetic acid. The reaction was stirred at room temperature overnight. It was quenched with 1N NaOH, and the product was extracted with CH$_2$Cl$_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.310 g of the desired product: mp 221° C.; MS (ES) m/z (relative intensity): 480 (M$^+$+H, 100).

EXAMPLE 97b

3-{(1,4-trans)-4-[4-(5-methoxy-quinolin-8-yl)-piperazin-1-yl]-cyclohexyl}-1-methyl-1H-indole-5-carbonitrile The trans isomer was isolated at the same time as the cis isomer as an off white solid (0.118 g).mp 206° C. MS (ES) m/z (relative intensity): 480 (M$^+$+H, 100).

EXAMPLE 98a

8-{(1,4-cis)-4-[4-(5-Fluoro-1H-indol-3-yl)-cyclohexyl]-piperazin-1-yl}-6-Fluoro-quinoline To a solution of 0.300 g of 6-Fluoro, 8-piperazino-quinoline in 10 mL of DCE, was added 0.411g of 4-(5-fluoro-1-methyl-3-indolyl)-cyclohexanone followed by 0.349 g of sodium triacetoxyborohydride and 0.1 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.190 g of the desired product: mp 194.5° C.; MS (ES) m/z (relative intensity): 461 ($M^++H$, 100).

EXAMPLE 98b

8-{(1,4-trans)-4-[4-(5-Fluoro-1H-indol-3-yl)-cyclohexyl]-piperazin-1-yl}-6-Fluoro-quinoline The trans isomer was isolated at the same time as the cis isomer as an off white solid (0.062 g).mp 171° C. MS (ES) m/z (relative intensity): 461 ($M^++H$, 100).

EXAMPLE 99a

3-{(1,4-cis)-4-[4-(6-Benzyloxy-quinolin-8-yl)-piperazin-1-yl]-cyclohexyl}-1-methyl-1H-indole-5-carbonitrile To a solution of 0.300 g of 6-Benzyloxy, 8-piperazino-quinoline in 10 mL of DCE, was added 0.252 g of 3-(4-oxo-cyclohexyl)-1-methyl-1H-indole-5-carbonitrile followed by 0.297 g of sodium triacetoxyborohydride and 0.1 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.172 g of the desired product: mp 171° C.; MS (ES) m/z (relative intensity): 556 ($M^++H$, 100).

EXAMPLE 99b

3-{(1,4-trans)-4-[4-(6-Benzyloxy-quinolin-8-yl)-piperazin-1-yl]-cyclohexyl}-1-methyl-1H-indole-5-carbonitrile The trans isomer was isolated at the same time as the cis isomer as an off white solid (0.083 g).mp 118.5° C. MS (ES) m/z (relative intensity): 556 ($M^++H$, 100).

EXAMPLE 100

3-{(1,4-cis)-4-[4-(6-Hydroxy-quinolin-8-yl)-piperazin-1-yl]-cyclohexyl}-1-methyl-1H-indole-5-carbonitrile A solution of 0.100 g of 3-{(1,4-cis)-4-[4-(6-Benzyloxy-quinolin-8-yl) piperazin-1-yl]-cyclohexyl}-1-methyl-1H-indole-5-carbonitrile in THF is added to a suspension of 0.015 gr 10% Pd/C in MeOH and hydrogenated for ½ hour. Filtered and the solvent was evaporated to give 0.045 g of the desired product. mp 144° C. MS (ES) m/z (relative intensity): 466 ($M^++H$, 100).

EXAMPLE 101

3-{(1,4-cis)4-[4-(6-fluoro-8-quinolinyl)-1-piperazinyl]-cyclohexyl}-1-methyl-1H-indole-5-'carboxamide To a solution of 0.100 g of 6-fluoro-8-{4-[4-(5-fluoro-1-methyl-1H-indol-3-yl)cyclohexyl]-1-'piperazinyl}quinoline in 5 ml (THF:MeOH ), 1 ml of 5N NaOH was added followed by 2 ml 30% $H_2O_2$. The mixture was stirred at ROOM TEMPERATURE for 24 hours. Water was added and the product was filtered to give 0.035 g of the desired product. mp 289° C. MS (ES) m/z (relative intensity): 486 ($M^++H$, 100).

EXAMPLE 102a

3-{(1,4-cis)-4-[4-(5-trifluoromethyl-quinolin-8-yl)-piperazin-1-yl]-cyclohexyl}-1-methyl-1H-indole-5-carbonitrile To a solution of 0.250 g of 5-Trifluoromethyl, 8-piperazino-quinoline in 10 mL of DCE, was added 0.224 g of 3-(4-oxo-cyclohexyl)-i-methyl-1H-indole-5-carbonitrile followed by 0.287 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.057 g of the desired product: mp 231° C.; MS (ES) m/z (relative intensity): 518 ($M^++H$, 100).

EXAMPLE 102b

3-{(1,4-trans)-4-[4-(5-trifluoromethyl-quinolin-8-yl)-piperazin-1-yl]-cyclohexyl}-1-methyl-1H-indole-5-carbonitrile The trans isomer was isolated at the same time as the cis isomer as an off white solid (0.044 g).mp 194–197° C. MS (ES) m/z (relative intensity): 518 ($M^++H$, 100).

EXAMPLE 103a

3-{(1,4-cis)-4-[4-(6-chloro-quinolin-8-yl)-piperazin-1-yl]-cyclohexyl}-1-methyl-1H-indole-5-carbonitrile To a solution of 0.300 g of 6-Chloro, 8-piperazino-quinoline in 10 mL of DCE, was added 0.305 g of 3-(4-oxo-cyclohexyl)-1-methyl-1H-indole-5-carbonitrile followed by 0.274 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.057 g of the desired product: mp 222° C.; MS (ES) m/z (relative intensity): 485 ($M^++H$, 100).

EXAMPLE 103b

3-{(1,4-trans)-4-[4-(6-chloro-quinolin-8-yl)-piperazin-1-yl]-cyclohexyl}-1-methyl-1H-indole-5-carbonitrile The trans isomer was isolated at the same time as the cis isomer as an off white solid (0.044 g).mp 229° C. MS (ES) m/z (relative intensity): 485 ($M^++H$, 100).

EXAMPLE 104a

8-{(1,4-cis)-4-[4-(5-Fluoro-1-methyl-1H-indol-3-yl)-cyclohexyl-piperazin-1-yl}-6-chloro-quinoline To a solution of 0.247 g of 6-Chloro, 8-piperazino-quinoline in 10 mL of DCE, was added 0.245 g of 4-(5- fluoro-1-methyl-3-indolyl)-cyclohexanone followed by 0.274 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.070 g of the desired product: mp 219° C.; MS (ES) m/z (relative intensity): 478 ($M^++H$, 100).

EXAMPLE 104b

8-{(1,4-trans)-4-[4-(5-Fluoro-1-methyl-1H-indol-3-yl)-cyclohexyl]-piperazin-1-yl}-6-chloro-quinoline The trans isomer was isolated at the same time as the cis isomer as an off white solid (0.049 g).mp 193° C. MS (ES) m/z (relative intensity): 478 ($M^++H$, 100).

EXAMPLE 105a

3-{(1,4-Cis)-4-[4-(5-chloro-8-quinolinyl)-1-piperazinyl]-cyclohexyl}-1-methyl-1H-indole-5-'carbonitrile To a solution of 0.250 g of 5-Chloro, 8-piperazino-quinoline in 10 mL of DCE, was added 0.260 g of 3-(4-oxo-cyclohexyl)-1-methyl-1H-indole-5-carbonitrile followed by 0.274 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.080 g of the desired product: mp 243–248° C.; MS (ES) m/z (relative intensity): 485 ($M^++H$, 100).

EXAMPLE 105b

3-{(1,4-trans)-4-[4-(5-chloro-8-quinolinyl)-1-piperazinyl]-cyclohexyl}-1-methyl-1H-indole-5-'carbonitrile The trans isomer was isolated at the same time as the cis isomer as an off white solid (0.034 g).mp 192–196° C. MS (ES) m/z (relative intensity): 485 ($M^++H$, 100).

EXAMPLE 106a

8-{(1,4-cis)-4-[4-(5-Fluoro-1-methyl-1H-indol-3-yl)-cyclohexyl]-piperazin-1-yl}-5-chloro-quinoline To a solution of 0.250 g of 5-Chloro, 8-piperazino-quinoline in 10 mL of DCE, was added 0.224 g of 4-(5-fluoro-1-methyl-3-indolyl)-cyclohexanone followed by 0.274 g of sodium triacetoxyborohydride and 0.1 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.053 g of the desired product: mp 196° C.; MS (ES) m/z (relative intensity): 478 ($M^++H$, 100).

EXAMPLE 106b

8-{(1,4-trans)-4-[4-(5-Fluoro-1-methyl-1H-indol-3-yl)-cyclohexyl]-piperazin-1-yl}-5-chloro-quinoline The trans isomer was isolated at the same time as the cis isomer as an off white solid (0.025 g).mp 196° C. MS (ES) m/z (relative intensity): 478 ($M^++H$, 100).

EXAMPLE 107a

8-{(1,4-cis)-4-[4-(6-Fluoro-1-methyl-1H-indol-3-yl)-cyclohexyl]-piperazin-1-yl}-5-chloro-quinoline To a solution of 0.250 g of 5-Chloro, 8-piperazino-quinoline in 10 mL of DCE, was added 0.250 g of 4-(6-fluoro-1-methyl-3-indolyl)-cyclohexanone followed by 0.274 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.030 g of the desired product: mp 107–110° C.; MS (ES) m/z (relative intensity): 478 ($M^++H$, 100).

EXAMPLE 107b

8-{(1,4-trans)-4-[4-(6-Fluoro-1-methyl-1H-indol-3-yl)-cyclohexyl]-piperazin-1-yl}-5-chloro-quinoline The trans isomer was isolated at the same time as the cis isomer as an off white solid (0.014 g).mp 228° C. MS (ES) m/z (relative intensity): 478 ($M^++H$, 100).

EXAMPLE 108a

8-{(1,4-cis)-4-[4-(5-benzyloxy-1-methyl-1H-indol-3-yl)-cyclohexyl]-piperazin-1-yl}-6-methoxy-quinoline To a solution of 0.650 g of 6-Methoxy, 8-piperazino-quinoline in 15 mL of DCE, was added 0.959 g of 4-(5-benzyloxy-1-methyl-3-indolyl)-cyclohexanone followed by 0.790 g of sodium triacetoxyborohydride and 0.5 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.175 g of the desired product: mp 168° C.; MS (ES) m/z (relative intensity): 561 ($M^++H$, 100).

EXAMPLE 108b

8-{(1,4-trans)-4-[4-(5-benzyloxy-1-methyl-1H-indol-3-yl)-cyclohexyl]-piperazin-1-yl}-6-methoxy-quinoline The trans isomer was isolated at the same time as the cis isomer as an off white solid (0.055 g).mp 228° C. MS (ES) m/z (relative intensity): 561 ($M^++H$, 100).

EXAMPLE 109a

8-{(1,4-cis)-4-[4-(6-fluoro-1-methyl-1H-indol-3-yl)-cyclohexyl]-piperazin-1-yl}-5-fluoro-quinoline To a solution of 0.231 g of 5-Fluoro, 8-piperazino-quinoline in 10 mL of DCE, was added 0.245 g of 4-(6-fluoro-1-methyl-3-indolyl)-cyclohexanone followed by 0.274 g of sodium triacetoxyborohydride and 0.1 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.030 g of the desired product: mp 112–115° C.; MS (ES) m/z (relative intensity): 461 (M$^+$+H, 100).

EXAMPLE 109b

8-{(1,4-trans)-4-[4-(6-fluoro -1-methyl-1H-indol-3-yl)-cyclohexyl]-piperazin-1-yl}-5-fluoro-quinoline The trans isomer was isolated at the same time as the cis isomer as an off white solid (0.010 g). MS (ES) m/z (relative intensity): 461 (M$^+$+H, 100).

EXAMPLE 110

3-{(1,4-cis)-4-[4-(6-methoxy-8-quinolinyl)-1-piperazinyl]-cyclohexyl}-1-methyl-1H-indol-5-ol A solution of 0.120 g of 8-{(1,4-cis)-4-[4-(5-benzyloxy-1-methyl-1H-indol-3-yl)-cyclohexyl]-piperazin-1-yl}-6-methoxy-quinoline in 10 ml THF is added to a suspension of 0.100 g 10% Pd/C in MeOH and hydrogenated for 1 hour. Filtered and the solvent was evaporated to give 0.036 g of the desired product. mp 250° C. MS (ES) m/z (relative intensity): 471 (M$^+$+H, 100).

EXAMPLE 111a

8-{(1,4-cis)-4-[4-(5-fluoro -1-methyl-1H-indol-3-yl)-cyclohexyl]-piperazin-1-yl}-5-fluoro-quinoline To a solution of 0.200 g of 5-Fluoro, 8-piperazino-quinoline in 10 mL of DCE, was added 0.245 g of 4-(5-fluoro-1-methyl-3-indolyl)-cyclohexanone followed by 0.274 g of sodium triacetoxyborohydride and 0.1 mL acetic acid. The reaction was stirred at room temperature overnight. It was quenched with 1N NaOH, and the product was extracted with CH$_3$Cl$_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.040 g of the desired product: mp 199–202° C.; MS (ES) m/z (relative intensity): 461 (M$^+$+H, 100).

EXAMPLE 111b

8-{(1,4-trans)-4-[4-(5-fluoro-1-methyl-1H-indol-3-yl)-cyclohexyl]-piperazin-1-yl}-5-fluoro-quinoline The trans isomer was isolated at the same time as the cis isomer as an off white solid (0.021 g). mp 197° C.; MS (ES) m/z (relative intensity): 461 (M$^+$+H, 100).

EXAMPLE 112a

8-Chloro-7-{(1,4-cis)-4-[4-(5-fluoro-1-methyl-1H-indol-3-yl)-cyclohexyl]-1-'piperazinyl}quinoline To a solution of 0.247 g of 8-Chloro, 7-piperazino-quinoline in 10 mL of DCE, was added 0.245 g of 4-(5-fluoro-1-methyl-3-indolyl)-cyclohexanone followed by 0.274 g of sodium triacetoxyborohydride and 0.2 mL acetic acid. The reaction was stirred at room temperature overnight. It was quenched with 1N NaOH, and the product was extracted with CH$_2$Cl$_2$. The organic phase was washed with water and dried over magnesium sulfate. The product was filtered through 100 mL of silica gel using 50% ethyl acetate/hexanes, 75% ethyl acetate/hexanes, and finally 100% ethyl acetate to give 0.085 g of the desired product: mp 182–184° C.; MS (ES) m/z (relative intensity): 478 (M$^+$+H, 100).

EXAMIPLE 112b

8-Chloro-7-{(1,4-trans)-4-[4-(5-fluoro-1-methyl-1H-indol-3-yl)cyclohexyl]-1-'piperazinyl}quinoline The trans isomer was isolated at the same time as the cis isomer as an off white solid (0.025 g). mp 181–182° C.; MS (ES) m/z (relative intensity): 478 (M$^+$+H, 100).

EXAMPLE 113a

3-{(1,4-cis)4-[4-(8-chloro-7-quinolinyl)-1-piperazinyl]-cyclohexyl}-1-methyl-1H-indole-5-'carbonitrile To a solution of 0.247 g of 8-Chloro, 7-piperazino-quinoline in 10 mL of DCE, was added 0.252 g of 4-(5-fluoro-1-methyl-1-H-3-indolyl)-cyclohexanone followed by 0.274 g of sodium triacetoxyborohydride and 0.2 mL acetic acid. The reaction was stirred at room temperature overnight. It was quenched with 1N NaOH, and the product was extracted with CH$_2$Cl$_2$. The organic phase was washed with water and dried over magnesium sulfate. The product was filtered through 100 mL of silica gel using 50% ethyl acetatelhexanes, 75% ethyl acetate/hexanes, and finally 100% ethyl acetate to give 0.075 g of the desired product: mp 240–242° C.; MS (ES) m/z (relative intensity): 485 (M$^+$+H, 100).

EXAMPLE 113b

3-{(1,4-trans)-4-[4-(8-chloro-7-quinolinyl)-1-piperazinyl]-cyclohexyl}-1-methyl-1H-indole-5-'carbonitrile The trans isomer was isolated at the same time as the cis isomer as an off white solid (0.015 g). mp 233–237° C.; MS (ES) m/z (relative intensity): 485 (M$^+$+H, 100).

EXAMPLE 114a

3-{(1,4-cis)-4-[4-(4-fluoro-quinolin-8-yl)-piperazin-1-yl]-cyclohexyl}-1H-indole-5-carbonitrile To a solution of 0.310 g (1.34 mmol) of 4-fluoro-8-piperazino-quinoline in 50 mL of CH$_2$Cl$_2$ was added 0.319 g (1.34 mmol) of 3-(4-oxo-cyclohexyl)-1H-indole-5-carbonitrile followed by 0.402 g (1.5 eq) of sodium triacetoxyborohydride and 0.076 mL acetic acid. The reaction was stirred at room temperature overnight. It was quenched with 1 N NaOH, and the product was extracted with ether. The organic phase was washed with water and dried. The product was filtered through 75 mL of silica gel using 25% ethyl acetate/hexanes, 75% ethyl acetate/hexanes, to give 0.185 g of the cis product: mp 152–160° C.; MS (ES) m/z (relative intensity): 454.3 (M$^+$+H, 100).

EXAMPLE 114b

3-{(1,4-trans)-4-[4-(4-fluoro-quinolin-8-yl)-piperazin-1-y]-cyclohexyl}-1H-indole-5-carbonitrile The trans isomer (0.065 g) was isolated at the same time as the cis compound, as an off-white solid: mp 144–152° C. MS (ES) m/z (relative intensity): 454.4 (M$^+$+H, 100).

The activity of the present compounds is demonstrated by the following standard pharmacological test procedures.

The PCR cloning of the human 5-HT$_{1A}$ receptor subtype from a human genomic library has been described previously Chanda et al., Mol. Pharmacol., 43:516 (1993). A stable Chinese hamster ovary cell line expressing the human 5-HT$_{1A}$ receptor subtype (5-HT$_{1A}$.CHO cells) was employed throughout this study. Cells were maintained in DMEM supplemented with 10% foetal calf serum, non-essential amino acids and penicillin/streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at –80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 μL of buffer. Competition experiments were performed by using 7 concentrations of unlabelled drug and a final ligand concentration of 1.5 nM. Non-specific binding was determined in the presence of 10 μM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md.) through a GF/B filter presoaked for 30 minutes in 0.5% polyethyleneimine.

A protocol similar to that used by Cheetham et al., Neuropharmacol., 32:737 (1993) was used to determine the affinity of compounds for the serotonin transporter. Briefly, frontal cortical membranes prepared from male Sprague-Dawley rats were incubated with $^3$H-paroxetine (0.1 nM) for 60 minutes at 25° C. All tubes also contained either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method of Cheng and Prusoff, Biochem. Pharmacol., 22:3099 (1973); Ki=IC50/((Radioligand conc.)/(1+KD)).

The [$^{35}$S]-GTPγS binding assay was similar to that used by Lazareno and Birdsall, Br. J. Pharmacol. 109:1120 (1993). Briefly, 5-HTFA cloned receptor membrane fragments (as used for 5-T IA receptor binding assays) were stored at –70° C. until needed. When needed, membranes were rapidly thawed, centrifuged at 40,000×g for 10 minutes and resuspended at 4° C. for 10 minutes in assay buffer (25 mM HEPES, 3 mM MgCl$_2$, 100 mM NaCl, 1 mM EDTA, 10 uM GDP, 500 mM DTT, pH 8.0). These membranes were then incubated for 30 minutes at 30° C. with [$^{35}$S]GTPgS (1 nM) in the presence of vehicle, test compound (one to eight concentrations), or excess 8-OH-DPAT to define maximum agonist response. All reactions are terminated by the addition of ice cold Tris buffer followed by rapid filtration using a Tom Tech® filtration device to separate bound from free [$^{35}$S]GTPgS. Agonists produce an increase in the amount of [$^{35}$S]GTPgS bound whereas antagonists produce no increase in binding. Bound radioactivity was counted and analyzed as above.

The following assays were performed by incubating the cells with DMEM containing 25 mM HEPES, 5 mM theophylline and 10 μM pargyline for a period of 20 minutes at 37° C. Functional activity was assessed by treating the cells with forskolin (1 uM final concentration) followed immediately by test compound (6 concentrations) for an additional 10 minutes at 37° C. In separate experiments, 6 concentrations of antagonist were preincubated for 20 minutes prior to the addition of 10 nM 8-OH-DPAT and forskolin. The reaction was terminated by removal of the media and addition of 0.5 ml ice cold assay buffer. Plates were stored at –20° C. prior to assessment of cAMP formation by a cAMP SPA assay (Amersham).

The compounds tested correspond to those prepared in Examples 1–13 above.

The results of the procedures are set forth in Table 1.

| Example No. | 5-HT$_{1A}$ (Ki, nM) | ST (K$_i$, nM,) | GTPγS ED50 (% EMax) | cAMP ED50 (EMax) |
|---|---|---|---|---|
| 1a | 32.0 | 38.0 | 327 (0%) | 631 (0%) |
| 1b | 5.29 | 155 | 176 (32%) | 17 (77%) |
| 2a | 117.3 | 27% | | |
| 2b | 22.3 | 0% | | |
| 3a | 36.7 | 5.4 | 650 (10%) | 400 (0%) |
| 3b | 4.62 | 10.07 | 42.6 (51%) | 155 (0%) |
| 4a | 33.5 | 12.7 | 278 (0%) | 580 (0%) |
| 4b | 5.45 | 35% | | 85 (7.5%) |
| 5a | 0% | 34% | | |
| 5b | 78.7% | 14% | | |
| 6a | 325.7 | 28 | 84.6 (53%) | 4.72 (80%) |
| 6b | 58.3 | 20% | | |
| 7a | 69.6 | 1.62 | 539 (0%) | 87 (0%) |
| 7b | 3.51 | 4.19 | | 8.9 (83%) |
| 8a | 60.3 | 25% | 0% | 357 (0%) |
| 8b | 2.87 | 0% | 38.6 (32%) | 8.9 (77%) |
| 9a | 87.1 | 4% | | |
| 9b | 13.0 | 12% | | |
| 10a | 15.81 | 18% | 0% | 209 (0%) |
| 10b | 7.78 | 0% | 16.3 (14%) | 3.9 (79%) |
| 11 | 0% | 40 | | |
| 12a | 234 | 0.76 | | |
| 12b | 53.2 | 35% | | |
| 13a | 563.5 | 8.9 | | |
| 13b | 827 | 40 | | |
| 14a | 819.9 | 17 | | |
| 14b | 0% | 40 | | |
| 15a | 694.2 | 28 | | |
| 15b | 0% | 16% | | |
| 16a | 0% | 29.0 | | |
| 16b | 0% #100 nM | 25% 100 nM | | |
| 17 | 0% | 2.5 | | |
| 18 | 129.4 | 1.36 | | |
| 19a | 264.4 | 5.72 | | |
| 19b | 26.2 | 24% | 418 (74%) | 14.9 (92%) |
| 20a | 631.2 | 29% | | |
| 20b | 14.9 | 0% | 35.5 (33%) | 3.05 (75.5%) |
| 21 | 110.4 | 11% | | |
| 22a | 80.7 | 4.96 | 0% | 101.3 (0%) |
| 22b | 11.6 | 36.5 | 4.5% | 357 (0%) |
| 23a | 103.2 | 22% | | |
| 23b | 14.9 | 32% | | |
| 24a | 65.7 | 6.90 | 15.4% | 52.1 (81%) |
| 24b | 11.3 | 36.0 | 73% | |
| 25A | 67.7 | 63.0 | 9% | 16.0 (0%) |
| 25b | 9.66 | 58.0 | 24 (46%) | |
| 26a | 59.1 | 4.1 | 3960 (18%) | 59.6 (0%) |
| 26b | 8.5 | 23.0 | 15 (39%) | |
| 27a | 69.7 | 8.6 | 139 (20%) | 212 (0%) |
| 27b | 6.54 | 28.0 | 26 (66%) | |
| 28 | 25.1 | 2.02 | 25 (0%) | 95 (0%) |
| 29a | 43.9 | 2.25 | 23% | 9.05 (0%) |
| 29b | 2.91 | 46.0% | 34 (70%) | |
| 30 | 24.5 | 1.25 | | 29.5 (95%) |
| 31a | 142.2 | 13 | | |
| 31b | 32.4 | 17% | | |
| 32a | 245.6 | 14 | | |

-continued

The results of the procedures are set forth in Table 1.

| Example No. | 5-HT$_{1A}$ (Ki, nM) | ST (K$_i$, nM,) | GTPγS ED50 (% EMax) | cAMP ED50 (EMax) |
|---|---|---|---|---|
| 32b | 49.1 | 22% | | |
| 33a | 98.9 | 1.9 | | |
| 33b | 19.2 | 45.0 | | |
| 33c | 431.0 | 7.1 | | |
| 34a | 185.4 | 1.49 | | |
| 34b | 8.37 | 17.0 | | |
| 35 | 70.1 | 91 | | |
| 36 | 12.34 | 28 | 84.6 (53%) | 4.72 (80%) |
| 38 | 124 | 7.22 | | |
| 44c | 21.0 | 1.5 | 556 (0%) | 521 (0%) |

As demonstrated by the results set forth above, the compounds of the present invention are active towards 5HT1A receptors and generally elevate serotonin levels by inhibiting 5-HT transport. Accordingly, the present compounds should be useful in treating disorders related to defects in serotonin concentration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously.

Compositions for oral administration may be either liquid or solid composition form.

Preferably, the pharmaceutical compositions containing the compounds of this invention are in unit dosage form, e.g., tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula:

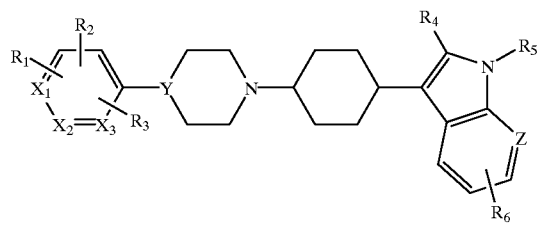

wherein:

$R_1$, $R_2$ and $R_3$ are each, independently, hydrogen, halogen, $CF_3$, alkyl, alkoxy, $MeSO_2$, or any two of $R_1$, $R_2$ and $R_3$ taken together with the ortho and meta carbon atoms of the ring to which they are attached can form a 5–7 membered carbocyclic or a 5–6 membered heterocyclic ring which includes up to two non-carbon ring atoms each of which independently is either N or O;

$R_4$ is hydrogen, halogen, or alkyl;

$R_5$ is hydrogen, alkyl, alkylaryl, or aryl; and $R_6$ is hydrogen, halogen, $CF_3$, CN, carbamido, or alkoxy;

$X_1$, $X_2$ and $X_3$ are each carbon or one of $X_1$, or $X_2$ may be nitrogen;

Y is nitrogen; and

Z is carbon or nitrogen;

with the proviso that if one of $X_1$ or $X_2$ is N then at least one of $R_1$, $R_2$ and $R_3$ is not H; or pharmaceutically acceptable salts thereof.

2. A compound of claim 1 which is 3-[cis-4-[4-(1H-Indol-4-yl)-1-piperazinyl]cyclohexyl]-1H-indole.

3. A compound of claim 1 which is 3-[trans-4-[4-(1H-indol-4-yl)-1-piperazinyl]cyclohexyl]-1H-indole.

4. A compound of claim 1 which is 4-Fluoro-3-[cis-4-[4-(1H-indol-4-yl)-1-piperazinyl]cyclohexyl]-1H-indole.

5. A compound of claim 1 which is 4-Fluoro-3-[trans-4-[4-(1H-indol-4-yl)-1-piperazinyl]cyclohexyl]-1H-indole;.

6. A compound of claim 1 which is 5-Fluoro-3-[cis-4-[4-(1H-indol-4-yl)-1-piperazinyl]cyclohexyl]-1H-indole.

7. A compound of claim 1 which is 5-Fluoro-3-[trans-4-[4-(1H-indol-4-yl)-1-piperazinyl]cyclohexyl]-l1H-indole.

8. A compound of claim 1 which is 6-Fluoro-3-[cis-4-[4-(1H-indol-4-yl)-1-piperazinyl]cyclohexyl]-1H-indole.

9. A compound of claim 1 which is 6-Fluoro-3-[trans-4-[4-(1H-indol-4-yl)-1-piperazinyl]cyclohexyl]-1H-indole.

10. A compound of claim 1 which is 5-Bromo-3-[cis-4-[4-(1H-indol-4-yl)-1-piperazinyl]cyclohexyl]-1H-indole.

11. A compound of claim 1 which is 5-Bromo-3-[trans-4-[4-(1H-indol-4-yl)-1-piperazinyl]cyclohexyl]-1H-indole.

12. A compound of claim 1 which is 5-Chloro-3-[cis-4-[4-(1H-indol-4-yl)-1-piperazinyl]cyclohexyl]-1H-indole.

13. A compound of claim 1 which is 5-Chloro-3-[trans-4-[4-(1H-indol-4-yl)-1-piperazinyl]cyclohexyl]-1H-indole.

14. A compound of claim 1 which is 3-{4-[(1,4-cis)-4-(1H-indol-4-yl)-piperazinyl-1-yl]cyclohexyl}-1H-indole-5-carbonitrile.

15. A compound of claim 1 which is 3-{4-[(1,4-trans)-4-(1H-indol-4-yl)-piperazinyl-1-yl]cyclohexyl}-1H-indole-5-carbonitrile.

16. A compound of claim 1 which is 5-Methoxy-3-[cis-4-[4-(1H-indol-4-yl)-1-piperazinyl]cyclohexyl]-1H-indole.

17. A compound of claim 1 which is 5-Methoxy-3-[trans-4-[4-(1H-indol-4-yl)-1-piperazinyl]cyclohexyl]-1H-indole.

18. A compound of claim 1 which is 3-[cis-4-[4-(1H-Indol-4-yl)-1-piperazinyl]cyclohexyl]-2-methyl-1H-indole.

19. A compound of claim 1 which is 3-[trans-4-[4-(1H-Indol-4-yl)-1-piperazinyl]cyclohexyl]-2-methyl-1H-indole.

20. A compound of claim 1 which is 3-{(1,4-cis)-4-[4-1H-Indole-4-yl)-piperazin-1-yl]-cyclohexyl}-1H-pyrrolo[2,3-b]pyridine.

21. A compound of claim 1 which is 3-{(1,4-trans)-4-[4-(1H-Indol-4-yl)-piperazin-1-yl]-cyclohexyl}-1H-pyrrolo[2,3-b]pyridine.

22. A compound of claim 1 which is 6-Fluoro-1-methyl-3-{cis-4-[4-(1-methyl-1H-indol-4-yl)-1-piperazinyl]cyclohexyl}-1H-indole.

23. A compound of claim 1 which is 3-{(1,4-cis)-4-[4-(1H-indol-4-yl)-piperazin-1-yl]cyclohexyl}-1-methyl-1H-indole-5-carbonitrile.

24. A compound of claim 1 which is 3-{(1,4-trans)-4-[4-(1H-indol-4-yl)-piperazin-1-yl]cyclohexyl}-1-methyl-1H-indole-5-carbonitrile.

25. A compound of claim 1 which is 1-Ethyl-3-{(1,4-cis)-4-[4-(1H-indole-4-yl)-piperazin-1-yl]-cyclohexyl}-1H-indole-5-carbonitrile.

26. A compound of claim 1 which is 3-{(1,4-cis)-4-[4-(1H-indol-4-yl)-piperazin-1-yl]-cyclohexyl}-1-propyl-1H-indole-5-carbonitrile.

27. A compound of claim 1 which is 3-{(1,4-trans)-4-[4-(1H-indol-4-yl)-piperazin-4-yl]-cyclohexyl}-1-propyl-1H-indole-5-carbonitrile.

28. A compound of claim 1 which is 3-{(1,4-cis)-4-[4-(1H-indol-4-yl)-piperazin-1-yl]-cyclohexyl}-1-isopropyl-1H-indole-5-carbonitrile.

29. A compound of claim 1 which is 3-{(1,4-trans)-4-[4-(1H-indol-4-yl)-piperazin-1-yl]cyclohexyl}-1-isopropyl-1H-indole-5-carbonitrile.

30. A compound of claim 1 which is 1-Benzyl-3-{(1,4-cis)-4-[4-(1H-indol-4-yl)-piperazin-1-yl]-cyclohexyl}-1H-indole-5-carbonitrile.

31. A compound of claim 1 which is 1-Benzyl-3-{(1,4-trans)-4-[4-(1H-indole-4-yl)-piperazin-1-yl]cyclohexyl}-1H-indole-5-5-carbonitrile.

32. A compound of claim 1 which is 1-Methyl-3-{(1,4-cis)-4-[4-(1-methyl-1H-indol-4-yl)-piperazine-1-yl]-cyclohexyl}-1H-indole-5-carbonitrile.

33. A compound of claim 1 which is 5-Fluoro-3-{(cis)-4-[4-(2-methoxy-phenyl)-piperazin-1-yl]-cyclohexyl}-1H-indole.

34. A compound of claim 1 which is 5-methoxy-3-{(1,4-cis)-4-[4-(2-methoxy-phenyl)-piperazin-1-yl]-cyclohexyl}-1H-indole.

35. A compound of claim 1 which is 5-Methoxy-3-{(1,4-trans)-4-[4-(2-methoxy-phenyl)-piperazin-1-yl]-cyclohexyl}-1H-indole.

36. A compound of claim 1 which is 3-{(1,4-cis)-4-[4-(2-methoxy-phenyl)-piperazin-1-yl]-cyclohexyl}-1H-pyrrolo[2,3-b]piperidine.

37. A compound of claim 1 which is 5-Fluoro-3-{(cis)-4-[4-(5-fluoro-2-methoxy-phenyl)-piperazin-1-yl]-cyclohexyl}-1H-indole.

38. A compound of claim 1 which is 5-Fluoro-3-{(trans)-4-[4-(5-fluoro-2-methoxy-phenyl)-piperazin-1-yl]-cyclohexyl}-1H-indole.

39. A compound of claim 1 which is 3-{(1,4-cis)-4-[4[(2,3-Dihydro-benzo[1,4]dioxin-5-yl)-piperazin-1-yl]-cyclohexyl}-4-fluoro-1H-indole.

40. A compound of claim 1 which is 3-{(1,4-cis)-4-[4-(2,3-Dihydro-benzo[1,4]dioxin-5-yl)-piperazin-1-yl]-cyclohexyl}-4-fluoro-1H-indole.

41. A compound of claim 1 which is 3-{(1,4-trans)-4-[4-(2,3-Dihydro-benzo[1,4]dioxin-5-yl)-piperazin-1-yl]-cyclohexyl}-5-fluoro-1H-indole.

42. A compound of claim 1 which is 3-{(1,4-trans)-4-[4-(2,3-Dihydro-benzo[1,4]dioxin-5-yl)-piperazin-1-yl]-cyclohexyl}-5-fluoro-1H-indole.

43. A compound of claim 1 which is 3-{(1,4-cis)-4-[4-(2,3-Dihydro-benzo[1,4]dioxin-5-yl)-piperazin-1-yl]-cyclohexyl}-6-fluoro-1H-indole.

44. A compound of claim 1 which is 3-{(1,4-trans)-4-[4-(2,3-Dihydro-benzo[1,4]dioxin-5-yl)-piperazin-1-yl]-cyclohexyl}-6-fluoro-1H-indole.

45. A compound of claim 1 which is 3-{(1,4-cis)-4-[4-(2,3-Dihydro-benzo[1,4]dioxin-5-yl]piperazin-cyclohexyl}-1H-indole-5-carbonitrile.

46. A compound of claim 1 which is 3-{(1,4-cis)-4-[4-(2,3-Dihydro-benzo[1,4]dioxin-5-yl)-piperazin-1-yl]-cyclohexyl}-1H-indole-5-carbonitrile.

47. A compound of claim 1 which is 3-{(1,4-trans)-4-(4-(2,3-Dihydro-benzo[1,4]dioxin-5-yl)-piperazin-1-yl]-cyclohexyl}-1H-indole-5-carbonitrile.

48. A compound of claim 1 which is 8-{4-[(1,4-cis)-4-(5-Fluoro-1H-indol-3-yl)-cyclohexyl]-piperazin-1-yl}quinoline.

49. A compound of claim 1 which is 8-{4-[(1,4-trans)-4-(5-Fluoro-1H-indol-3-yl)-cyclohexyl]-piperazin-1-yl}-quinoline.

50. A compound of claim 1 which is 8-{4-(1,4-cis)-4-[4-(5-Fluoro-1-methyl-1H-indol-3-yl)-cyclohexyl]-piperazin-1-yl}-quinoline.

51. A compound of claim 1 which is 3-[(1,4-cis)-4-(4-Quinolin-8-yl-piperazin-1-yl)-cyclohexyl]-1H-indole-5-carbonitrile.

52. A compound of claim 1 which is 3-[(1,4-trans)-4-(4-Quinolin-8-yl-piperazin-1-yl)-cyclohexyl]-1H-indole-5-carbonitrile.

53. A compound of claim 1 which is 1-Methyl-3-[(1,4-cis)-4-(4-quinolin-8-yl-piperazin-1-yl)-cyclohexyl]-1H-indole-5-carbonitrile.

54. A compound of claim 1 which is 5-Fluoro-3-{(1,4-cis)-4-[4-(6-fluoro-chroman-8-yl)-piperazin-1-yl]-cyclohexyl}-1H-indole.

55. A compound of claim 1 which is 5-Fluoro-3-{(1,4-trans)-4-[4-(6-fluoro-chroman-8-yl)-piperazin-1-yl]-cyclohexyl}-1H-indole.

56. A compound of claim 1 which is 5-Fluoro-3-{(1,4-cis)-4-[4-(5-fluoro-2,3-dihydro-benzofuran-7-yl)-piperazin-1-yl]-cyclohexyl}-1H-indole.

57. A compound of claim 1 which is 5-Fluoro-3-{(1,4-trans)-4-[4-(5-fluoro-2,3-dihydro-benzofuran-7-yl)-piperazin-1-yl]-cyclohexyl}-1H-indole.

58. A compound of claim 1 which is 3-{(1,4-cis)-4-[4-(5-Fluoro-2,3-dihydro-benzofuran-7-yl)-piperazin-1-yl]-cyclohexyl}-1H-indole-5-carbonitrile.

59. A compound of claim 1 which is 3-{(1,4-trans)-4-[4-(5-Fluoro-2,3-dihydro-benzofuran-7-yl)-piperazin-1-yl]-cyclohexyl}-1H-indole-5-carbonitrile.

60. A compound of claim 1 which is 3-{(1,4-trans)-4-[4-(5-Fluoro-2,3-dihydro-benzofuran-7-yl)-piperazin-1yl]-cyclohexyl}-1-methyl-1H-indole-5-carbonitrile.

61. A compound of claim 1 which is 3-[(1,4-cis)-4-[4-(Benzofuran-7-yl-piperazin-1-yl)-cyclohexyl]-1H-indole-5-carbonitrile.

62. A compound of claim 1 which is 3-[(1,4-trans)-4-[4-(Benzofuran-7-yl-piperazin-1-yl)-cyclohexyl]-1H-indole-5-carbonitrile.

63. A compound of claim 1 which is 5-Fluoro-3-{4-[4-(2-methoxy-phenyl)-piperazin-1-yl]cyclohex-1-enyl}-1H-indole.

64. A compound of claim 1 which is 3-{4-[4-(1H-Indol-4-yl)-piperazin-1-yl]-cyclohex-1-enyl}-1H-indole-5-carbonitrile.

65. A compound of claim 1 which is 5-Fluoro-3-{cis-4-[4-(1H-indol-4-yl)piperazinyl]-cyclohexyl}-1-methyl-1H-indole.

66. A compound of claim 1 which is 3-{(1,4-cis)-4-[4-(6-Methoxy-quinolin-8-yl)-piperazin-1-yl]-cyclohexyl}-1H-indole-5-carbonitrile.

67. A pharmaceutical composition comprising a compound of the formula:

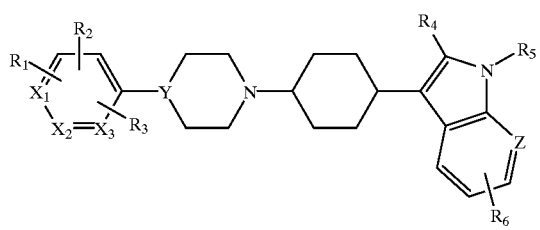

wherein:

$R_1$, $R_2$ and $R_3$ are each, independently, hydrogen, halogen, $CF_3$, alkyl, alkoxy, $MeSO_2$, or any two of $R_1$, $R_2$ and $R_3$ taken together with the ortho and meta carbon atoms of the ring to which they are attached can form a 5–7 membered carbocyclic or a 5–6 membered heterocyclic ring which includes up to two non-carbon ring atoms each of which independently is either N or O;

$R_4$ is hydrogen, halogen, or alkyl;

$R_5$ is hydrogen, alkyl, alkylaryl, or aryl; and $R_6$ is hydrogen, halogen, $CF_3$, CN, carbamido, or alkoxy;

$X_1$, $X_2$ and $X_3$ are each carbon or one of $X_1$, or $X_2$ may be nitrogen;

Y is nitrogen; and

Z is carbon or nitrogen;

with the proviso that if one of $X_1$ or $X_2$ is N then at least one of $R_1$, $R_2$ and $R_3$ is not H; or pharmaceutically acceptable salts thereof.

68. A method for treating depression in a patient in need thereof comprising administering to said patient an antidepressant effective amount of a compound of the formula:

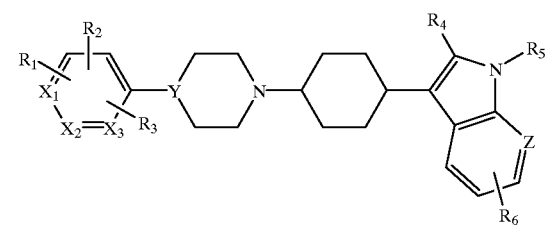

wherein:

$R_1$, $R_2$ and $R_3$ are each, independently, hydrogen, halogen, $CF_3$, alkyl, alkoxy, $MeSO_2$, or any two of $R_1$, $R_2$ and $R_3$ taken together with the ortho and meta carbon atoms of the ring to which they are attached can form a 5–7 membered carbocyclic or a 5–6 membered heterocyclic ring which includes up to two non-carbon ring atoms each of which independently is either N or O, $R_4$ is hydrogen, halogen, or alkyl;

$R_5$ is hydrogen, alkyl, alkylaryl, or aryl; and $R_6$ is hydrogen, halogen, $CF_3$, CN, carbamido, or alkoxy;

$X_1$, $X_2$ and $X_3$ are each carbon or one of $X_1$, or $X_2$ may be nitrogen;

Y is nitrogen; and

Z is carbon or nitrogen;

with the proviso that if one of $X_1$ or $X_2$ is N then at least one of $R_1$, $R_2$ and $R_3$ is not H; or pharmaceutically acceptable salts thereof.

* * * * *